(12) United States Patent
John et al.

(10) Patent No.: US 12,102,818 B2
(45) Date of Patent: Oct. 1, 2024

(54) WEARABLE NEUROSTIMULATION SYSTEM WITH CURATED THERAPY

(71) Applicant: EBT MEDICAL, INC., Toronto (CA)

(72) Inventors: Michael Sasha John, Larchmont, NY (US); Mike Labbe, Twinsburg, OH (US); Keith R. Carlton, Holliston, MA (US); Paul B. Yoo, Toronto (CA); Suranjan Roychowdhury, Minneapolis, MN (US); Tamara Baynham, Cazenovia, NY (US); Ken W. Mariash, Los Angeles, CA (US); David Lubensky, San Francisco, CA (US); John Lai, San Bruno, CA (US); Brian Hoffer, San Francisco, CA (US); Rachel Lichte, Durham, NC (US); Jon Lawson, Cottage Grove, MN (US)

(73) Assignee: EBT Medical, Inc., Toronto (CA)

( * ) Notice: Subject to any disclaimer, the term of this patent is extended or adjusted under 35 U.S.C. 154(b) by 508 days.

(21) Appl. No.: 17/305,792

(22) Filed: Jul. 14, 2021

(65) Prior Publication Data
US 2022/0016413 A1    Jan. 20, 2022

Related U.S. Application Data

(60) Provisional application No. 63/052,192, filed on Jul. 15, 2020.

(51) Int. Cl.
  *A61N 1/04*    (2006.01)
  *A61N 1/36*    (2006.01)

(52) U.S. Cl.
  CPC ......... *A61N 1/0456* (2013.01); *A61N 1/0492* (2013.01); *A61N 1/36034* (2017.08)

(58) Field of Classification Search
  CPC . A61N 1/0456; A61N 1/0492; A61N 1/36034
  See application file for complete search history.

(56) References Cited

U.S. PATENT DOCUMENTS

2019/0175915 A1*  6/2019  Brill ................... A61N 1/37247

* cited by examiner

*Primary Examiner* — Alyssa M Alter
(74) *Attorney, Agent, or Firm* — Rosenberg, Klein & Lee

(57) ABSTRACT

Systems and methods for providing curated neurostimulation are disclosed such that users are enabled to provide improved therapy in a home environment. Stimulation protocols can be assessed to provide improved targeted stimulation of a nerve and less unwanted side effects. Sets of stimulation montages and associated weights are defined and are selected or adjusted in pre-defined using pre-defined operations that simplify adjustment of characteristics of the stimulation field such as the geometry and location of the provided stimulation. Stimulation matrix pads are arranged and activated to provide advantages. Strategies for adjusting the intensity of the stimulation field incorporate weighting values in non-primary channels and are disclosed. Curated neurostimulation can also include providing defined schedules for events and activities related to the therapy such as providing schedules for stimulation treatment, surveying a user, providing education and remote user support. Features related to decreasing and managing risk of skin events are included as part of the therapy. Both wearable and implanted embodiments are disclosed.

22 Claims, 16 Drawing Sheets

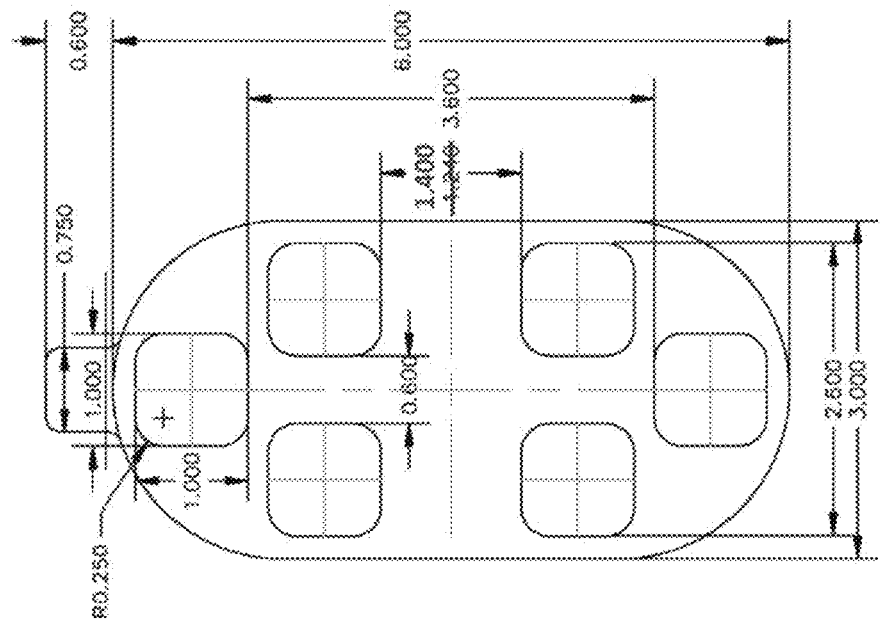
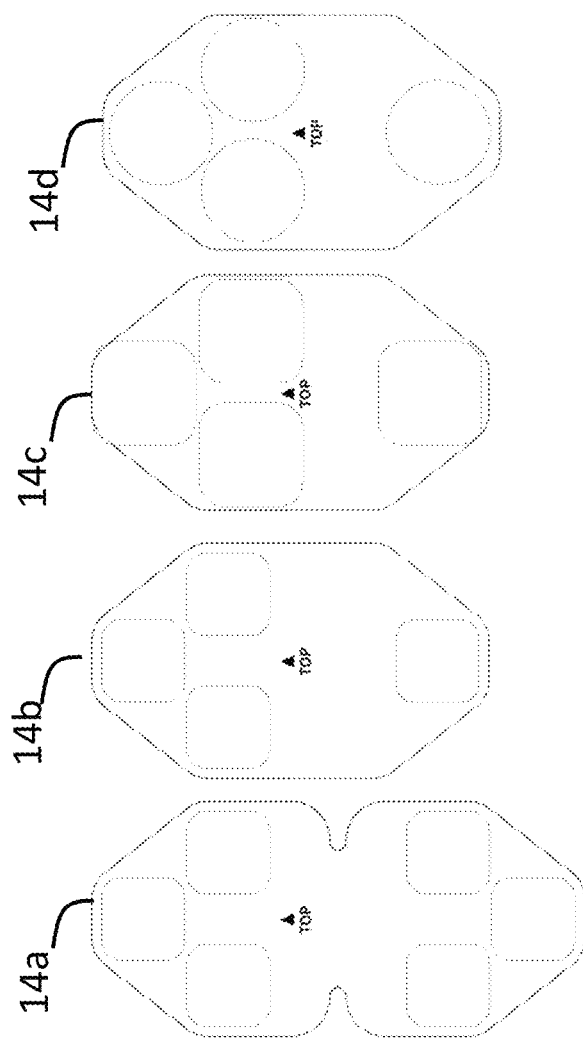
FIG. 4a  FIG. 4b  FIG. 4c  FIG. 4d

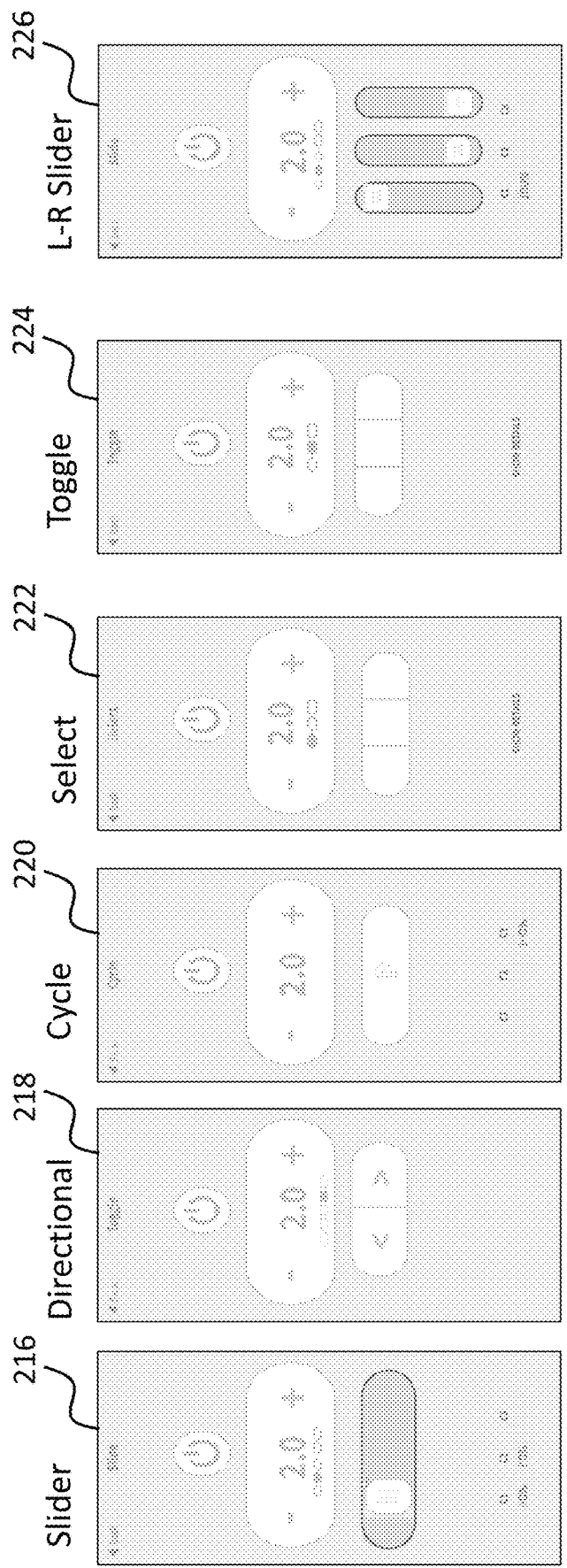

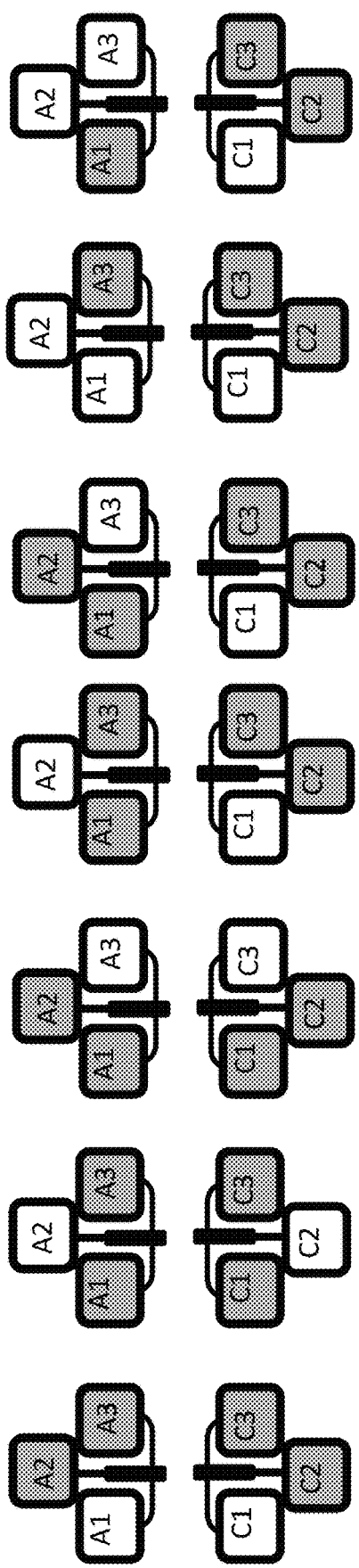
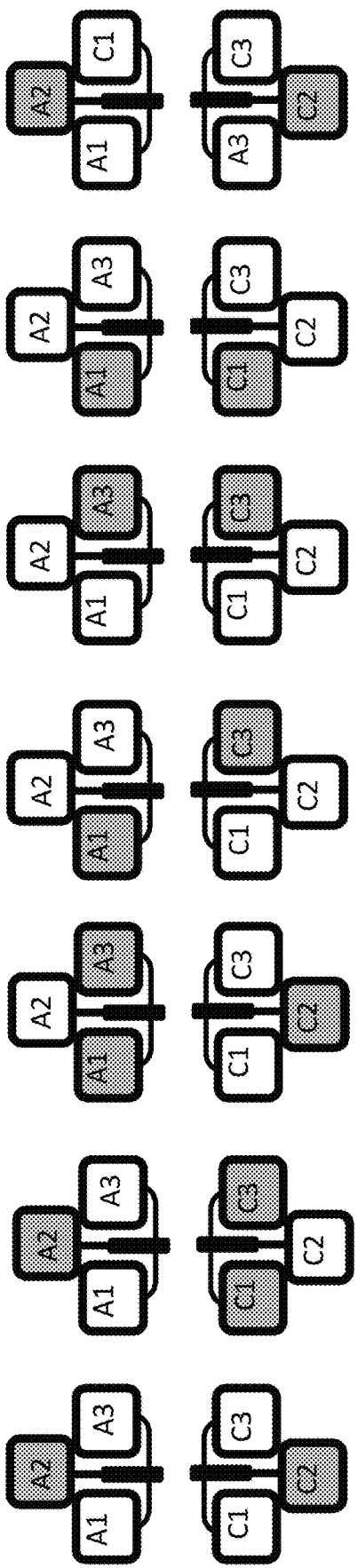

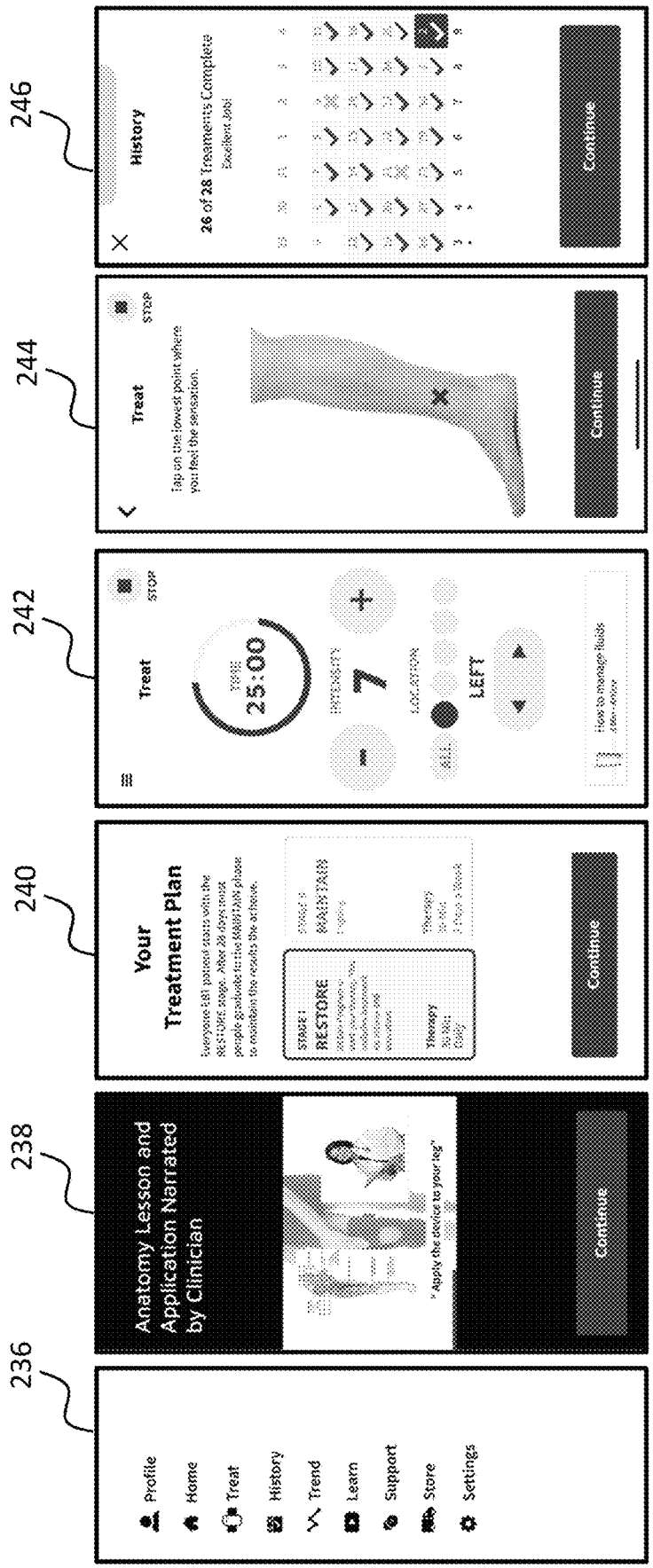

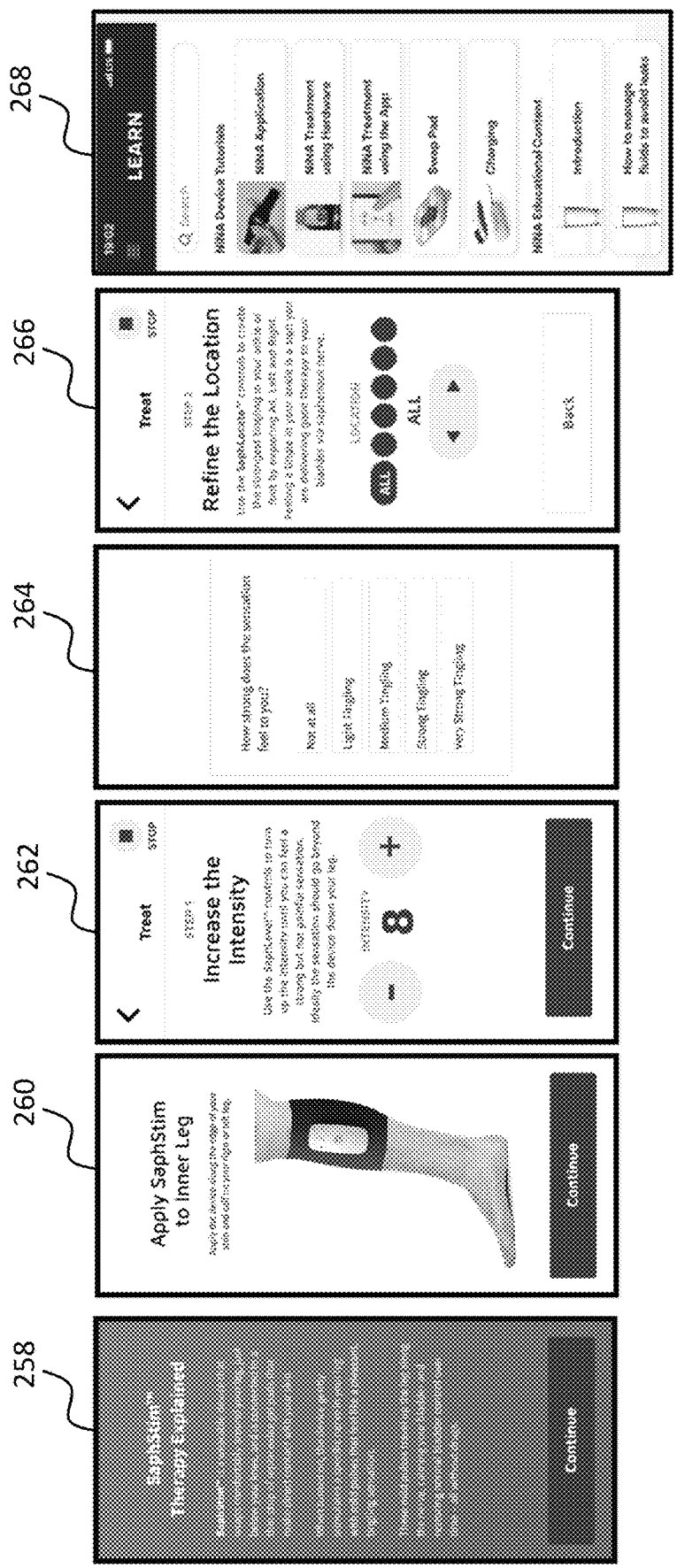

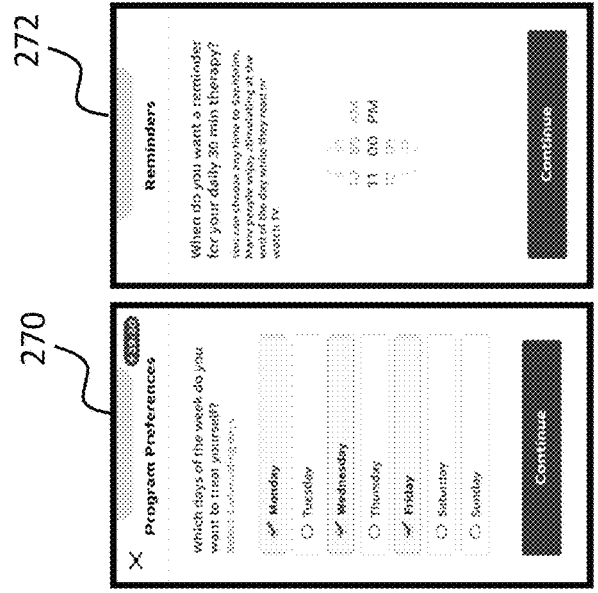
FIG. 10g
FIG. 10h
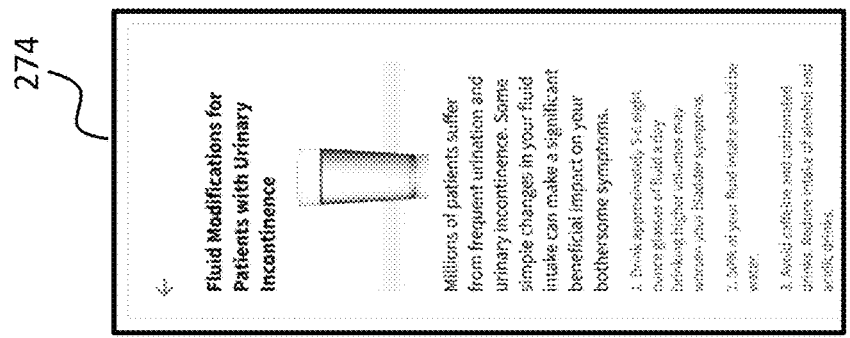
FIG. 10i
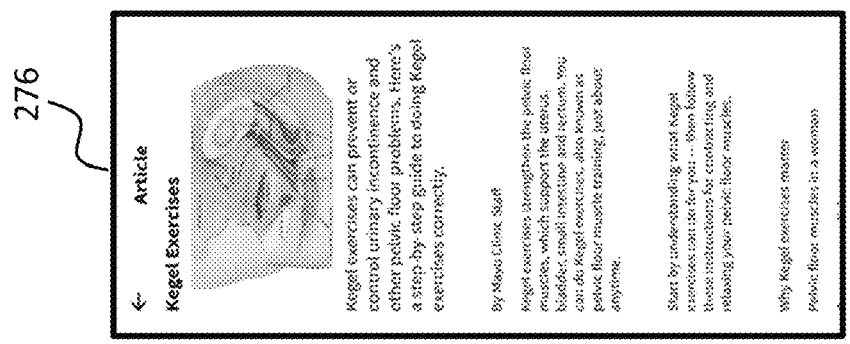
FIG. 10j
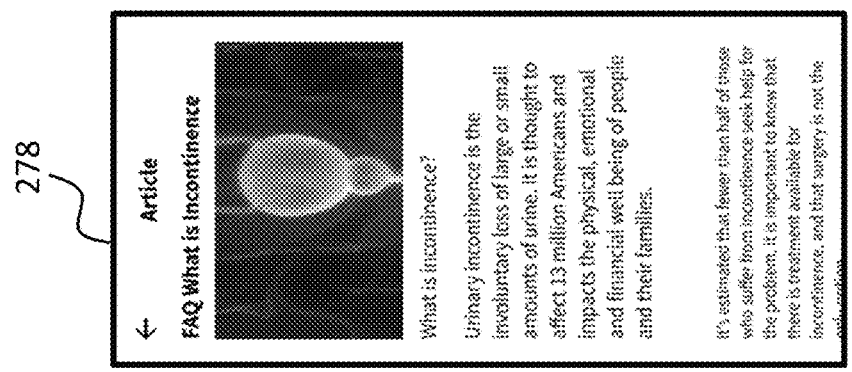
FIG. 10k

| Outcome | 180 Day | | 360 Day | |
|---|---|---|---|---|
| | >21 Day induction | ≤21 Day induction | >21 Day induction | ≤21 Day induction |
| % UUI Responder | 77% | 35% | 77% | 35% |
| HRQL ≥10 | 83% | 67% | 83% | 70% |

WEARABLE NEUROSTIMULATION SYSTEM WITH CURATED THERAPY

REFERENCE TO RELATED APPLICATIONS

This application is based upon Provisional Application Ser. No. 63/052,192 filed on Jul. 15, 2020.

INCORPORATION BY REFERENCE

This application incorporates by reference Provisional Application Ser. No. 63/052,192 filed at the United States Patent & Trademark Office on Jul. 15, 2020.

FIELD OF THE INVENTION

The invention relates to the field of stimulating biological tissue to improve the health or wellness of a user.

BACKGROUND

Stimulation of biological tissue can be used to improve health and wellness. Stimulation of peripheral tissue may cause changes at both peripheral and central sites in the treatment of disease or for the promotion of wellness by modulating the function of organs. Stimulation of the vagus nerve(s) is a good example of stimulation at a peripheral site in the neck that modulates brain and heart activity and produce systemic changes in immune and metabolic activity. Stimulation of cranial nerves can provide relatively non-invasive treatment options for conditions such as headache or migraine rather than requiring direct stimulation of brain tissue. Bioelectronic medicine is progressively drawing increased focus as a non-pharmaceutical treatment option for various diseases.

Stimulation of peripheral sites to treat unwanted symptoms, medical disorders, and conditions, or to promote health or create desired results in the brain or body, is attractive since this can provide benefit without the risks and invasiveness of direct stimulation of organs such as the brain or heart. Target stimulation sites in limb areas such as the arms, hands, legs and feet have been shown to provide benefit in treating, or improving symptoms of, a wide array of disorders. Candidate sites can be stimulated, and stimulation parameters and treatment schedules can be assessed for medical benefit in an individual or population of individuals who have been diagnosed (or "self-diagnosed") with a medical condition. Unwanted symptoms or states related to, for example, the following: pelvic floor disorders; hypertension; digestive disorders; pain; immunological or metabolic disorders or states, obesity; attentional, psychiatric or cognitive disorders; appetite; and other disorders, symptoms, or states which may be typically treated with medication can be treated with electrical stimulation which provides less risks of side-effects or drug interactions. Stimulation of nerves of the leg, arm, or neck may offer sites for a wide treatment of common disorders including cardiovascular disorders such as hypertension.

Stimulation of nerves in the lower leg offer opportunities to treat disorders such as pelvic floor disorders that include urinary and fecal incontinence which may manifest with pathology related to urge (e.g., overactive bladder or "OAB"). The inventors have shown that saphenous nerve (SAFN) stimulation for treatment of OAB symptoms has many benefits compared to other candidate peripheral neuromodulation targets (e.g., preferred sensation of stimulation, less affected by edema, stronger treatment response and less risks). When stimulating nerves in the leg using wearable non-invasive neurostimulators advantages are obtained when the target nerves are successfully stimulated while decreasing risk of, or avoiding, stimulation of non-target nerves and/or tissue such as calf muscle.

Systems and methods which allow easy control of stimulation field characteristics (e.g., shape, strength, orientation, location, perceived intensity, and vector summation) should improve nerve modulation treatment and resulting therapy outcomes. Systems and methods are needed for allowing easy adjustability and confirmation of the correct settings of stimulation field characteristics. Operations related to selecting, adjusting, and assessing stimulation field characteristics can be carried out by a patient following instructions and providing feedback, a medical professional in the setting of a medical clinic, at home by a user or caregiver, or a combination (e.g., remote telemedicine).

Novel hardware and software controls and components; algorithms and logic flows; curated provision and adjustment of the therapy regimen features such as selection or assessment of stimulation field characteristics, curated treatment support and scheduled treatment events provided by a digital ecosystem would provide benefits over existing therapies. Additionally, an easy onboarding process; instructional exercises and content; patient education about the treatment on the disease, and on treatments and behaviors that can improve symptoms; compliance prompts and trackers; and, other novel features of the invention will now be disclosed.

SUMMARY OF INVENTION

An object of the invention is to provide for improved peripheral nerve recruitment of target nerves using curated field steering realized by systems and methods incorporating novel software and hardware solutions.

An object of the invention is to provide sets of weighting values used to adjust the amplitude of stimulation provided for sets of stimulation channels to provide smooth transitions between sets of stimulation channels.

An object of the invention is to provide software-based artificial intelligence/machine learning program for obtaining user responses and operating upon these to establish improved stimulation protocol characteristics.

An object of the invention is to provide systems and methods that permit adjustment of the location, geometry, depth of electrical field penetration or other stimulation field characteristics without the subject experiencing unwanted jumps in sensation of stimulation intensity which hinder a user's ability to make comparisons across a set of candidate settings.

An object of the invention is to realize strategies which incorporate: a) neural targeting in which the risk or amount of undesired stimulation of collateral nerves or adjacent muscle is reduced; b) use of weighting factors to allow adjustment of the stimulation field without producing sharp transitions in the strength or perception of stimulation; c) the provision of sensory masking stimuli that permits a preferred sensory experience and/or decreases discomfort.

An object of the invention is to provide guided adjustment of a set of stimulation field parameters to provide for improved nerve targeting and avoid stimulating non-desirable tissue, such as calf muscle, shin bone or cutaneous nerves and branches which can cause discomfort and even be dangerous for some users (e.g., ambulatory users, since this may cause strain, tearing, or loss of control of muscles).

An object of the invention is to configure stimulation parameters to provide stimulation with cutaneous nerve fiber types or receptor types (mechanoreceptors, thermoreceptors) and processing of modalities such as touch, pressure, vibration, and temperature to serve as a sensory mask.

An object of the invention is to configure stimulation parameters to decrease unwanted stimulation of cutaneous nerve fibers and receptors (e.g., nociceptors for nociception pain) through targeted nerve stimulation.

Another object of the invention is to provide an adjustable level of tuning for a stimulation field controller which includes at least 2 levels of specificity for adjustment such as "Coarse" and "Fine" that may be selected by a user.

Another object of the invention is to provide at least one modality of stimulation that provides an adjunct stimulation signal (which may also be termed a "distractor" or "mask" signal) before or during the treatment stimulation, wherein the mask signal serves to improve the subjective experience of the stimulation and may decrease the sensation of pain and/or increase stimulation tolerance and which may allow a larger stimulation signal to be supplied without the user experiencing pain or discomfort.

Another object of the invention is to provide at least one modality of stimulation that provides a stimulation mask simultaneously with the treatment stimulation signal, wherein the stimulation mask is provided by adjacent electrodes at an intensity level that is lower than that provided by primary channels of stimulation.

Another object is to provide systems and methods that permit selection of an improved stimulation montage for stimulating a target nerve.

An object of the invention is to provide for the incorporation of "guarded" or 'blocked" stimulation montages and user controls that allow users to adjust stimulation using gestures on a touch sensitive display to focus or restrict the stimulation field or avoid stimulation of an area.

Another object is to provide combinations of anode and cathode assignments to stimulation pads to shape a stimulation field to increase the depth of the stimulation from the skin surface.

Another object is to provide combinations of anode and cathode assignments to stimulation pads to selectively modulate target tissue while avoiding tissue areas which cause unwanted side effects (e.g., other nerves, calf muscle, neck muscle, or a muscle in the arm when stimulating a nerve target in the arm to modulate cardiac characteristics such as blood pressure).

Another object of the invention is to provide a curated "Restore" neurostimulation treatment induction program that guides a user with a scheduled treatment program across a predefined interval.

Another object of the invention is to provide a curated "Maintain" neurostimulation treatment maintenance program that guides a user with a scheduled treatment program.

Another object is to provide remote or software-based coaching (e.g., behavioral therapy and nutritional education), and presentation of educational and survey items that are tailored to educating, surveying, assessing, tracking, and adjusting therapy of an individual based, and further adjusting these based upon user behavior and input (e.g., changes in symptom scores compared to a baseline score).

Another object is to combine stimulation therapy with behavioral therapy (e.g., guides and prompts related to, for example, times for eating/drinking, exercise, etc.), nutritional information, and other guidance and information to improve the overall therapy benefit.

Another object is to provide treatment of a medical disorder which is configured for at-home guided treatment of a user with little, if any, management by a medical professional or, alternatively, with scheduled telemedicine management provided by medical professionals.

These and other objects of the invention are disclosed in the remainder of this application.

BRIEF DESCRIPTION OF THE DRAWINGS

FIGS. 4a to 4e show embodiments of various stimulation matrix designs.

FIGS. 5a to 5j show embodiments of user interface screens for allowing curated user adjustment of stimulation field characteristics of the stimulation matrix.

FIGS. 6a to 6n shows embodiments of different activation montages provided by the stimulation matrix, with anodes ("A"), cathodes ("C") which are activate (non-shaded) or inactive (shaded).

FIGS. 9a to 9k show example user interface screens of a digital ecosystem that guide, inform, and obtain user input as part of a curated treatment program of a disorder such as a pelvic floor disorder and more specifically OAB.

FIGS. 10a to 10k show additional examples of user interface screens of a curated treatment program of digital ecosystem that permit user control of stimulation and screens related to behavioral coaching and education.

DESCRIPTION OF THE PREFERRED EMBODIMENTS

Figure 1C:
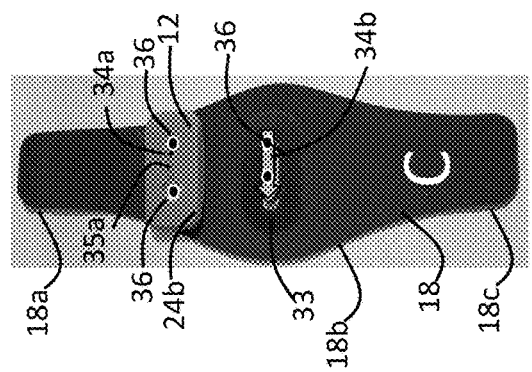
FIG. 1c shows a wrap having an interface guide with a directionally keyed aperture, a neurostimulator (view of bottom surface), and directionally keyed connectors of a stimulation matrix and a neurostimulator.

While specific embodiments may deviate, the following terms generally mean the following:

Subject, patient, or user are used interchangeably. A user provides stimulation to himself/herself in an at-home setting or is a medical technician controlling the neurostimulator in a clinic setting, a caregiver, a medical professional controlling the neurostimulator remotely using the internet or a wireless communication channel (e.g., WIFI or cellular network): the user may not be the person receiving treatment. Subject may refer to a participant in a research study.

Anode and cathode are designations for the initial phase of a biphasic pulse. While use of biphasic stimulation signals may cause the anode-cathode designation to switch during the provision of stimulation signals, the designation represents a stimulation circuit that is supplied by at least two channels of a stimulus generator.

Stimulation pad is a conductive substrate that is applied to the patient's skin and is used to provide an electrical stimulation signal (also termed "conductive pad" or "electrode")

Stimulation channel is an electrical pathway terminating in a stimulation pad and for purposes of this disclosure may also be considered to be part of at least one active stimulation pad serving as cathode or anode or an inactive pad. When stimulation is provided by other modalities, then individual transducers for magnetic, sonic, vibration or other type of energy then can each be considered a stimulation channel.

Stimulation circuit is at least one cathode and anode; Primary stimulation circuit/channel refers to the channels providing the highest amplitude signals; Stimulation matrix (or "matrix") is a set of 3 or more conductive stimulation pads that serve as an "electrode array" for providing transcutaneous electrical stimulation.

Stimulation signal "strength", "amplitude", and "intensity" may generally be used interchangeably, provided however, it is understood that perceived intensity may also be increased in other manners such as making the pulse duration longer which increases total charge delivered.

Horizontal "x-axis" or "Left-Right" axis of the stimulation matrix generally spans across the limb, while the proximal-distal axis (i.e. "vertical" or "y-axis") aligns with the axis of a user's limb. If secured to the left leg, then "left" is closer to the shin and right is closer to the calf-muscle. The opposite occurs on the right leg. The horizontal and vertical adjustments are typically orthogonal. When there is both horizontal and vertical offset between channels then these are "diagonal".

Rows and columns of the stimulation matrix refer to stimulation circuits defined and distributed with an approximately horizontal or vertical orientation.

Stimulation matrix geometry refers to the arrangement of, and spaces between, the activated pads on a stimulation matrix, and may also refer to the shapes and sizes of individual pads.

Stimulation protocol defines the stimulation montage and the stimulation signals sent to each channel of the stimulation matrix which result in the stimulation field characteristics produced by the stimulation matrix. This also refers to characteristics of scheduled stimulation sessions (e.g., timing and duration of scheduled treatment sessions).

Stimulation montage includes the designation of each stimulation pad of a matrix (e.g., anode, cathode, inactive), and the weights used at each channel (typically to scale amplitude, but also able to affect other waveform parameters such as pulse width). The stimulation montage is part of the stimulation parameters that define the signals supplied from the matrix (active geometry+stimulation signals). The stimulation montage provides a profile of activated pads of the stimulation matrix.

Stimulation field geometry is the shape of the vector electrical field induced in the user's body.

"Recruiting" and "modulating" a nerve indicates influence of the electrical field on neural activity, and typically indicates influencing the activity of the nerve by initiating action potentials.

Skin stimulation threshold is stimulation that is sufficient to cause stimulation to be perceived at the cutaneous area under one or more stimulation pads.

Target nerve threshold is stimulation that is sufficient to cause recruitment of a target nerve as evidenced by the perception of paresthesia moving away from the stimulation pads or at an area distinct from the stimulation pads, or evidenced by stimulation evoked sensory or motor responses.

A therapy regimen includes the stimulation protocol and all treatment operations and events that are defined to be provided as part of therapy.

The Non-invasive Neuromodulation Assistant (NiNA) system refers to the combination of hardware and software, and the features realized by the digital ecosystem, that work together to provide the neurostimulation treatment and advantages of the disclosed invention.

Wearable Neurostimulation System

Figure 1B:
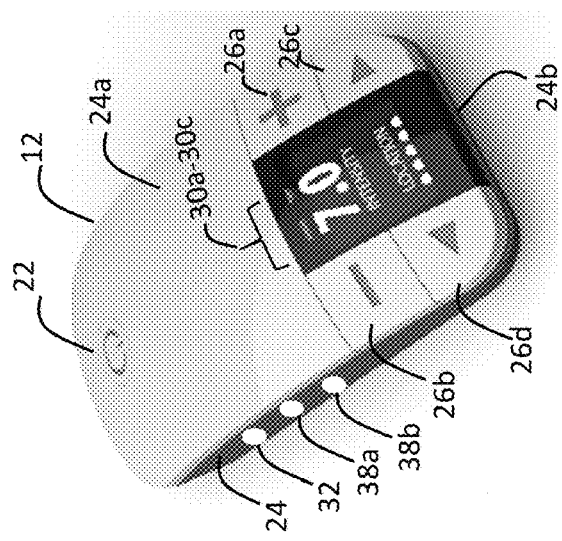
FIG. 1b shows a neurostimulator with controls, a display and ports.
Figure 1A:
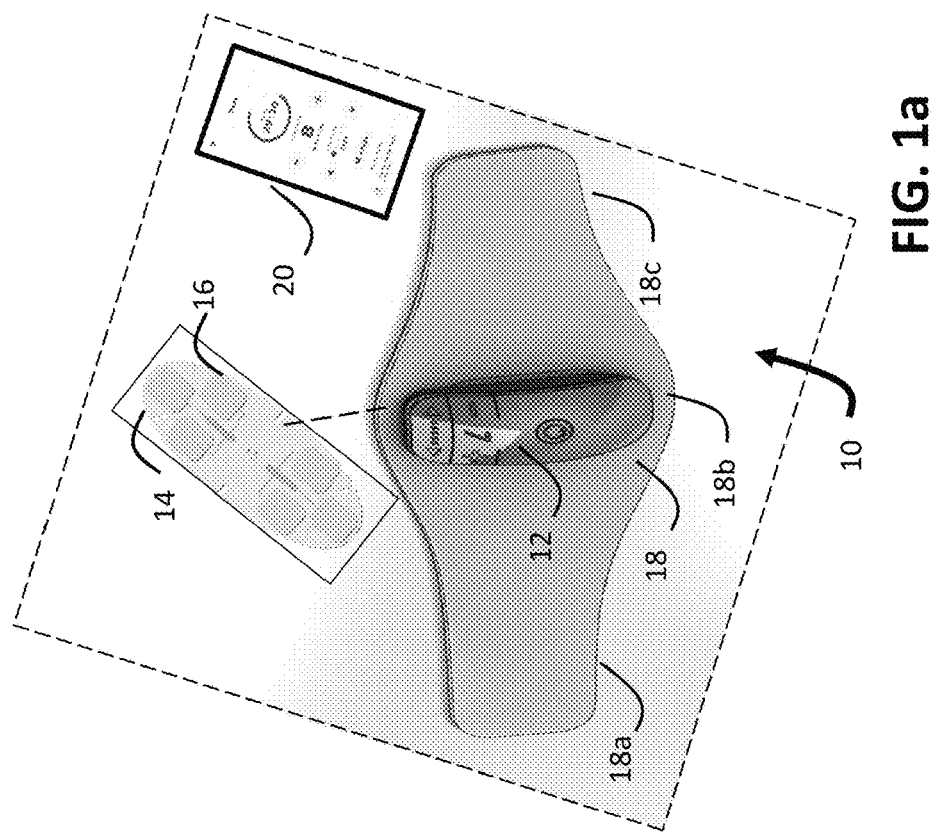
FIG. 1a shows a neurostimulator system including neurostimulator, stimulation matrix of stimulation pads, wearable wrap, and a user device with a user interface screen that controls stimulation parameters.

FIG. 1a shows an embodiment of a neurostimulation system 10 including a neurostimulation device 12 that connects electrically and physically to a stimulation matrix 14 with stimulation pads 16 that are removably attached to, and deliver electrical stimulation signals through, a user's skin. The device 12 and matrix 14 can be secured to a location on a user's limb (e.g., lower leg) using a garment such as a wrap 18. The wrap 18 is designed with a long arm 18a, a short arm 18c, and a base region 18b therebetween which is configured to engage with the device 12. A user device 20 is realized as a smartphone running Android or iOS and operating a mobile app 21 which allows a user to communicate with and control the neurostimulator 12. The control of selected treatment parameters may be constrained according to permissions allowed by a curated therapy regimen which may be adjustable or be predefined restrictions. Stimulus generation electronics of a stimulation module of the device 12 provides stimulation under control of the device's control module to provide stimulation signals to the stimulation matrix 14 during treatment. In an embodiment, the stimulation circuitry of the device 12 provides independent, current controlled stimulation channels, so that each stimulation pad 16 of the stimulation matrix 14 serves as cathode, anode, passive ground return. Each Pad has its own power source allowing for precise control at each pad so that what is specified is the actual stimulation field that is provided and maintained.

In an embodiment of the neurostimulation system 10, there is provided a stimulation module 42 having an electrical stimulus generator therein which transmits electrical signals through a plurality of electrical generator channels. A control module 40 is electrically coupled to the electrical stimulus generator for activating or deactivating each of the electrical channels in accordance with a predetermined protocol having a set of at least two stimulation montages with a weighting value defined for each of a set of activated pads (seen in FIGS. 6a-6n). A stimulation matrix 14 is provided defining a plurality of pairs of electrical stimulation pads 16 which are positioned in a fixed and predefined arrangement on a user's skin. Each of the pairs of electrical stimulation pads 16 has an anodic and a cathodic pad electrically coupled to a respective cathodic and anodic electrical generator channel. Each of the electrical stimulation pads 16 are either in an active state when a respective electrical generator channel is activated or in an inactive state when a respective electrical generator channel is deactivated.

A first stimulation montage (any one of the stimulation matrices 14 shown in FIGS. 6a-6n) is defined for the stimulation pads 16 of the stimulation matrix 14 where each of the electrical stimulation pads 16 is in an active or inactive state. At least one second stimulation montage is defined for the electrical stimulation pads 16 of the stimulation matrix 14 where at least one of the electrical stimulation pads 16 is in an inactive state when at least one stimulation pad 16 is in an active state in the first stimulation montage. A user interface device 20 permits the user to cause transitioning the stimulation matrix from the first stimulation montage to the second stimulation montage.

While an object of the invention is selective targeting of the saphenous nerve (SAFN) for treatment of overactive bladder (OAB), in alternative embodiments any nerve (or combination of nerves) in the leg, especially the lower leg at or below the level of the knee, (e.g., the saphenous nerve, sural nerve, posterior tibial nerve, tibial nerve, peroneal nerve) may be stimulated to treat a wide array of symptoms and disorders. The invention may also be used to stimulate other limbs or body parts, such as at least one arm of a user.

FIG. 1b shows an embodiment of a neurostimulator device 12 having a housing formed as a durable plastic enclosure containing electronics and power. The top housing portion 24a has a power button 22 and stimulation field controls that allow user adjustment of the stimulation amplitude 26a,26b and location 26c,26d, a display such as a touch sensitive display 30 that provides information relating to stimulation field amplitude 30a (or "intensity") and location 30b, and other information 30c (e.g., treatment session elapsed time/time remaining; battery power level; number of remaining stimulation sessions or days before the matrix 14 must be replaced). The housing 24 also has at least one port 32 allowing for exchange of data/power signals. This can be configured to receive a connector having a set of electrical channels/contacts (e.g., USB, lightning cable connector, or pogo pins with magnetic retention), and have a corresponding set of electrical channels/contacts which route signals to modules of the device 12 (e.g., power, communication, or control modules), and can allow for wired control of, or data/power communication with, the device 12.

The device controls allow the user to start, stop, and pause stimulation by causing corresponding operations to occur in a control module. For example, after a therapy session has started pressing the power button 22 for ~1 second pauses or restarts the stimulation, while holding the button 22 for longer (e.g., 2 seconds) causes shut-down operations to occur (e.g., updates device memory and then turns it off or sets it into a lower power standby mode as per step 132 of FIG. 8b), or pressing buttons 26a,26b to increase or decrease the amplitude of stimulation pulses, or perform "field control" 26c,26d that can change characteristics of the stimulation field such as location. Field control improves capture of a target nerve (e.g., the SAFN) while minimizing stimulation of surrounding nerve and muscle tissue (i.e., nerve targeting increases selective activation). Field controls provides advantages such as obviating a trial-and-error method of stopping stimulation, relocating stimulation pads, and re-starting the stimulation. The touch sensitive display 30 indicates stimulation field characteristics using either graphical or text-based information, and may also provide a simple user interface. The characteristics include information about, for example, stimulation intensity 30a, location/geometry of the stimulation montage 30b, and other information 30c (e.g., stimulation status Off/On/Paused, Time left). The neurostimulator device 12 can also operate additional input/output accessories (I/O components, sensors, or transducers) such as a camera 38a that allows the neurostimulator device 12 to scan and track relevant information about other system components (e.g., barcode information of a disposable stimulation matrix) or take pictures of a potential skin problem. Another I/O component is a speaker 38b that can provide auditory cues related to treatment operations (e.g., provide a tone if the stimulation matrix is not attached correctly).

FIG. 1c shows an embodiment with a garment such as a leg wrap 18 realized as a flexible/fabric wrap that secures the neurostimulator 12 and stimulation matrix to a user's upper calf area during treatment. The bottom housing 24b of a neurostimulator 12 is configured with a shaped (or "keyed") device connector 34a to engage with (physically and electrically) a shaped matrix connector 34b provided on the top side of a stimulation matrix to secure both connectors to each other and through the wrap 18 with an intended or orientation. The neurostimulator 12 includes a stimulation module having signal generation circuitry for delivering electrical stimulation pulses to the pads of the stimulation matrix through electrical channels/contacts 35a,35b (not shown) of the connectors 34a,34b to provide a plurality of independently controlled stimulation channels. Each channel of the set of channels/contacts 35a of the shaped connector 34a of the neurostimulator 12 connect to, or may be dynamically routed to, 1 or more channels of signal generation circuitry of at least one pulse generator of the neurostimulator. Accordingly, the stimulation pads of the matrix may be independently controlled to provide selected stimulation signals and to be active (e.g., anode, cathode) or inactive.

In embodiments, the connectors 34a,34b are shaped asymmetrically to only permit engagement with a predetermined physical orientation. The keyed connection between device 12 and matrix 14 is established through a keyed aperture in the interface guide 33, and can use magnets 36 to form a magnetic connection between the matrix and neurostimulator device. Magnets 36 provided for the two halves 34a,34b of the connector assembly allow these to "snap" together when properly aligned provide a secure connection between the corresponding electrically conductive channels 35a,35b. The keyed connectors have an arrow shape so that the UP direction is intuitive to the user (e.g., arrow points UP when worn on the leg). As such, the "female/lock" portion of the connector 34a forms an "arrow" outline which matches corresponding "male/key" shaped connector 34b of the matrix, and corresponding shaped opening in the wrap. The connector 34a on the bottom of the neurostimulator 12 housing, connector 34b on the top of the array, and the aperture of the interface guide 33 of the wrap 18 are all keyed to cause proper application of these three system components during therapy.

In embodiments, the shaped connector 34a and electrical channels/contacts 35a are configured to also connect with a custom adaptor (not shown) to provide for communication of power/data signals with a user device 20 connected to a cable. Some of the electrical channels/contacts 35a are configured to route signals to a power or communication module of the neurostimulator device. In other words, the connector 34a that is connectable to a stimulation matrix, may also have contacts that allow it to serve as a system interface for charging or communication purposes.

Figure 2:
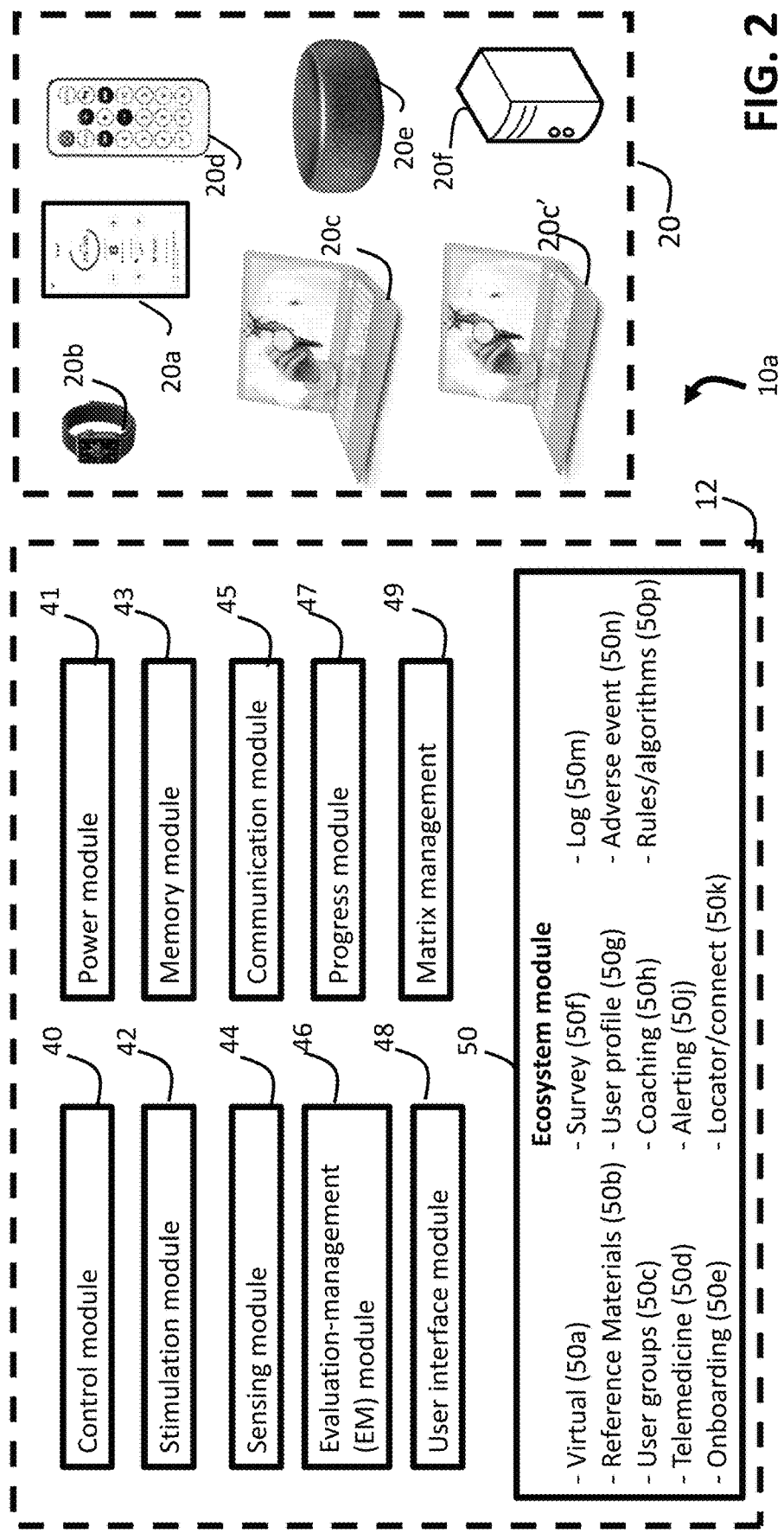
FIG. 2 shows modules of a neurostimulation system realized in the neurostimulator, and user devices including remote server computers of a telemedicine service or doctor clinic.
Figure 3B:
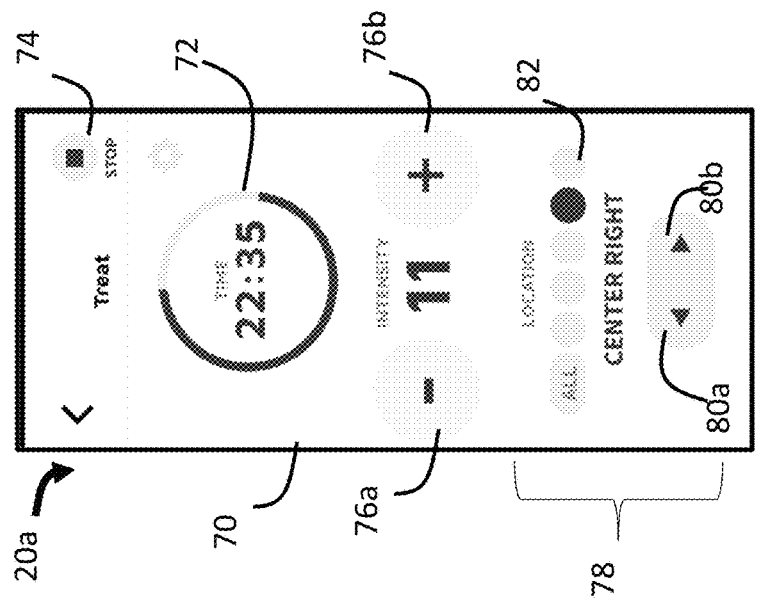
FIGS. 3b to 3f show exemplary user interface screens for controlling stimulation montages provided with the stimulation matrix.
Figure 3A:
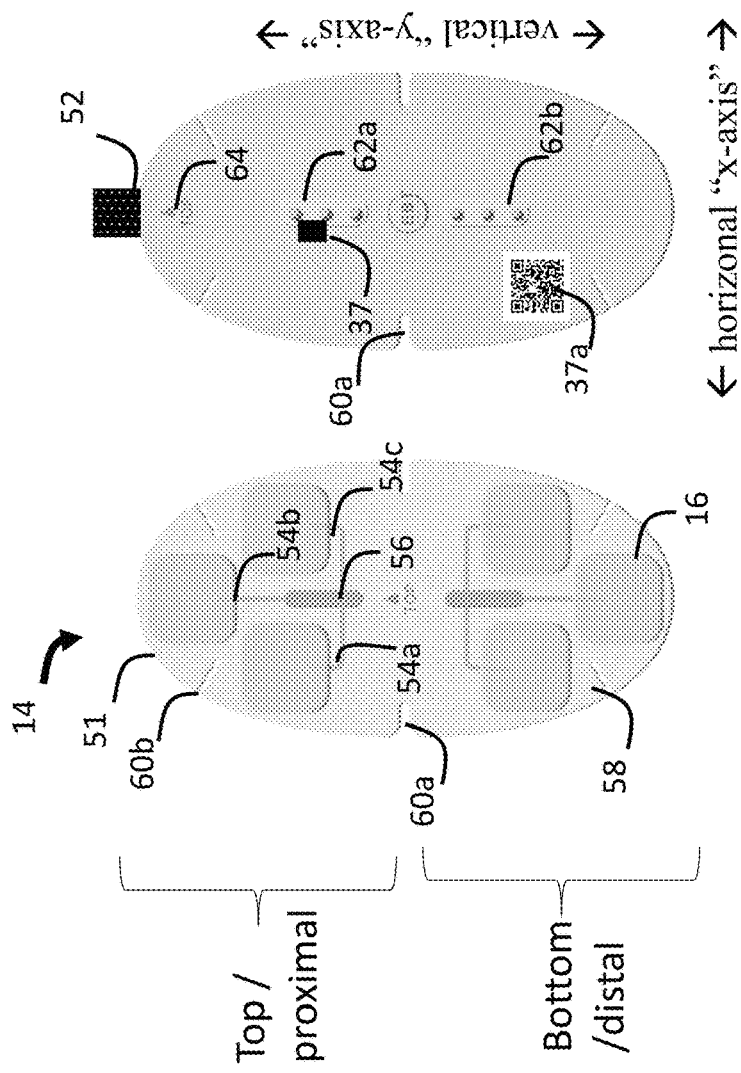
FIG. 3a shows an embodiment of the stimulation matrix.

In embodiments, the shaped connector 34b of the matrix has electronics for providing functionality such as a readable unique ID 37 (see FIG. 3a). A unique ID 37 may be realized using a microchip or RFID chip integrated into the connector 34b that uniquely identifies each stimulation matrix (e.g., with a serial number) to a neurostimulator device using wired (e.g., through connector 34a) or wireless (e.g., RFID) means. Alternatively, a matrix may have a unique ID 37 displayed as a bar or QR code 37A (see FIG. 3a) that is read by an I/O component 38 such as a camera 38a of the neurostimulator (see FIG. 1b) or of user device 20. The ID information can be operated upon by the neurostimulator or can be transmitted from the neurostimulator to a user device where it is processed by a system module (e.g., evaluation-management module 46 of FIG. 2). As will be discussed in FIG. 2, the ID information 37 can be processed by software of a user interface module 48 and operated upon by an evaluation-management module 46 to determine if the matrix meets compliance criteria of a matrix management module 49, such as whether the matrix has been used less than a maximum permitted number of treatment sessions or cumulative stimulation times.

Connective Wrap

In embodiments, the system uses a flexible, stretchable fabric wrap 18 with a base region 18b and two tapered wing regions 18a,18c or "arms". The base region 18b contains an interface guide 33 having a rigid frame containing a shaped aperture allowing shaped connector portions 34a,34b to engage. The wrap, interface guide, and shaped connectors collaborate to promote correct use by: a) correctly positioning and orienting the neurostimulator and matrix (when stimulating the SAFN the matrix should located on the medial aspect of the leg and a tab portion 52, if provided on the matrix, should be located at the top with the neurostimulator display having the intended orientation to display information to a patient); b) securing the matrix and device to the patient's leg during therapy; c) providing adjustable, suitable and comfortable pressure against the skin, and d) providing unobstructed access to device display and user controls.

As shown in FIG. 1a, in one embodiment the wrap is sandwiched between the matrix 14 and the device 12. This is then wrapped around the patient's upper calf area so the matrix is located over a portion of the user's SAFN. Velcro or similar attachment material can be used to secure the arms 18a,18c to each other. Additionally, adjustable straps may be provided on the arms of the wrap to allow the user to adjust the tightness of the wrap 18. The shape of the wrap can be important since the SAFN is a sensory rather than motor nerve that is selectively or primarily stimulated during therapy. Accordingly, patients should be able to engage in ambulatory activity without worrying about unwanted motor movement or muscle injury. In embodiments, the wrap is oriented and biased to be asymmetric on its top and bottom edges to provide improved fit. For example, the bottom is shaped with steeper angles on its bottom edges that engages the calf muscle area, than on its proximal end to better match the shape of the leg and calf muscle. The improved fit around a user's calf region can provides support, and decreases the risk of improper fit or migration if patients are ambulatory during therapy. The wrap 18 can be formed of known biocompatible materials (e.g., mixtures of Polyester, and other breathable fabrics such as Lycra, spandex, elastane, stretchy yarn). In embodiments, the wrap is formed of 1-4 layers of material to produce a net result of stable or moderate stretch (e.g., 0-100% stretch) as may be realized using weaves or other designs that allow for 2-way or 4-way stretch.

In an alternative embodiment the wrap 18 may be realized as a flexible substrate having conductive stimulations pads (e.g., dry or reusable electrodes) on its bottom surface which are adapted to be connected to the neurostimulator and apply stimulation to the skin of the user. Rather than a wrap the system may be used with a garment such as a sock form factor with electroconductive regions.

Neurostimulation System Components & Modules

FIG. 2 shows embodiments of components and modules of a neurostimulation system 10a. Modules may be realized within the housing of a neurostimulator 12 and also within other system components such as the matrix 14, the wrap 18, and user devices 20. The modules contain the software (computer code), algorithms and rules, hardware/electronic circuitry, user interface components (e.g., transducers and transceivers), and other resources required to provide the features ascribed to the module which enable the system 10a to function. Modules can be realized, and resources shared, in a distributed manner across two or more components of the system 10a. For example, the user interface module 48 of the neurostimulator device 12 or of the user device 20 can accept user input, operate upon this input, and communicate the output of the operation to the other device so that both devices of the system 10a operate collaboratively to provide the intended therapy. Rather than having electronics (e.g., stimulus generating, control, and/or routing circuitry) realized within the neurostimulator housing, an electronic assembly can be attached to the top of the stimulation matrix, connected with the housing of the neurostimulator, and controlled by a processor of the control module 40 of the neurostimulator 12. Accordingly, modules disclosed as existing within the neurostimulator housing, can typically be realized in least one user device 20, or other system component.

The control module 40 of the neurostimulator 12 has a processor for implementing computer code instructions related to the provision of therapy and device operation. The control module also has timers, a real time clock, memory, and is understood to incorporate any circuitry typically available in, and well known to exist in, consumer electronics such as smartphones, health tracking wearable devices, and devices commonly used for providing electrical stimulation to a user at home or in a clinic. The control module 40 also contains all the treatment parameters and protocols, schedules, algorithms, and rules that are used to provide one or more curated treatment programs. In embodiments, the control module 40 is configured to implement a plurality of features with a treatment regimen that enable a user-friendly experience when using the system 10a. Features related to a curated onboarding experience, user training, and scheduled treatment, user friendly adjustment of stimulation protocol parameters which provides improved nerve modulation and perception of stimulation, coaching, education and support activities (and other features that will be disclosed) are realized by the digital ecosystem.

The power module 41 has a rechargeable power supply that allows for multiple uses between recharges. It may also have a primary cell or a combination of the two. Recharging may occur using wired recharging provided through a port 32, through connector 35a via an adaptor, or by wireless inductive charging circuitry of the power module 41. The power module also has power management, safety, isolation and monitoring circuitry to provide power related operations.

The stimulation module 42 includes one or more stimulus generators with circuitry to generate one or more channels of stimulation for providing a stimulation signal according to a stimulation protocol. The stimulation module 42 includes circuitry for allowing impedance measurement and adjusting signals in relation to the measurements. The module includes processing circuitry (e.g., analog and digital signal conditioning modules, filters, amplifiers, DA/AD circuitry, memory, clocks and timers, switches, and multiplexors) for production and control of stimulation signals. In embodiments, one or more signal generators are configured to control the stimulation provided to each of the stimulation matrix pads, so each of a plurality of stimulating pads 16 is independently assignable to be active (e.g., anode or cathode) or inactive. The stimulation module is configured to provide stimulation signals according to stimulation parameter protocols to the active stimulation pads.

In embodiments, when the stimulation matrix has 6 stimulation pads, the module allows each of the 6 pads to operate as a programmable, selectable electrode, according to parameters defined in the stimulation protocol. Multiple stimulus generators allow independent control of a plurality of stimulation signals which may be provided on a simultaneous or interleaved basis. The characteristics of multiple channels of stimulation can be controlled to provide field steering functionality. Constant current and constant voltage stimulation circuitry may be used by the stimulus generator. The stimulation circuitry of the stimulation module 42, and the sensing circuitry of the sensing module 44 may be connected to any of stimulation matrix pads through channels 35a of a shaped connector 34a on the bottom surface of the device housing 24b.

The stimulation module 42 provides user-friendly and simple adjustment of stimulation protocol parameters that affect the location and shape of the stimulation field using NiNA's "SaphLocate" features as will be described, which includes some of the following:

a. The stimulation module 42 also contains sets of defined stimulation montages which include channel assignments (anode, cathode, inactive), and channel weighting values (which may be based upon the amplitude of the electrical signals transmitted by the electrical stimulus generator and other parameters such as pulse duration, frequency, etc.) that are used to adjust the stimulation signals that are provided by each stimulation channel (i.e., at each stimulation pad). It may include tables of channel weighting values (also termed "weighting factors" or "weighting values") that are used to adjust the stimulation signals that are provided to a user through each stimulation channel.

b. The stimulation module 42 also contains distinct sets of defined stimulation montages which are selected when a) a user is assessing different stimulation montages during training or assessment that may occur prior to providing treatment stimulation; and, b) a user is providing stimulation therapy during treatment. The module also contains sets of stimulation montages that are defined for either "coarse" or "fine" resolution adjustment.

c. The stimulation module 42 also contains sets of stimulation montages that have been defined to be used in a series when a user adjusts the stimulation field in a defined direction (e.g., a left-right or proximal-distal). The module also contains algorithms or rules for accessing look-up tables that define how a stimulation montage is adjusted or selected according to user input using field steering controls, or circuits that allow similar adjustment. The module is configured to permit adjustment of stimulation montages to occur according to a predefined sequence of stimulation templates. The selection or adjusting of at least one stimulation field characteristic which is defined by the stimulation templates can include, for example: a) the location of the stimulation field, the spread of the field, and the fall-off of the field, as will be disclosed.

In embodiments, the stimulation module 42 signal generators are configured to provide stimulation signals including pulse trains, bursting, sinusoidal waveform (0.1 Hz to >50 kHz), arbitrary waveforms, band limited noise (narrow or wide band), inferential electrical stimulation which is provided using multiple channels of a stimulation montage to provide targeting capability.

The memory module 43 manages storage and retrieval of data created or used by other modules of the system. For example, it can manage or search log data (generated by the log module 50m), store libraries of video content (used by the reference materials module 50a) used to provide educational and behavioral coaching, instructional content, and reference information that is accessed or operated upon by various modules of the ecosystem module 50. The module provides database functionality and manages lookup tables of other modules to store and retrieve values related to stimulation parameters, treatment protocols, and user defined parameter values and input such as responses to survey items or user preferences. The memory module may also manage content that is stored and updated in a web storage resource (i.e., in the "cloud") or on remote computers 20f.

The sensing module 44 includes circuitry for operating the sensors such as accelerometers, electrodes that can sense impedance or physiological measures which can be sent to the evaluation-management module to evaluate measures such as heart rate, evoked nerve potentials (e.g., evoked compound action potentials "ECAP", sensory nerve action potentials "SNAP"), or evoked EMG responses. It may also contain optical sensors (e.g., for measurement of heart rate or blood oxygen levels), and sensors for obtaining data related to moisture, skin temperature, or deriving cardiac measures such as blood pressure, etc.

The communication module 45 provides all circuitry and software algorithms required for the system components to communicate between each other or with other devices. For example, the system components shown in FIG. 2 include a series of user devices 20 which can communicate with the neurostimulator 12 to allow user control of the stimulation therapy. The module contains circuitry and operating instructions to allow system components to "handshake" and communicate securely and wirelessly using Bluetooth, WIFI, and other wireless protocols. In an embodiment, the communication module updates a contact log in the log module 50m based upon inter-device communication.

An evaluation-management (EM) module 46 contains protocols for evaluating sensed data, such as a) deriving evoked potential data (e.g., operating signal processing algorithms to derive measures of averaged SNAP data), b) assessing accelerometry data or EMG data to determine a user state or activity level (e.g., walking, running, sleeping, or lying down). The EM module 46 is also configured to operate the memory module 43 to store a log/history of device operations including durations, intensities, and other parameters used during stimulation, sensed patient activity levels or positions, etc. The module also evaluates impedance sensed by the sensing module 44 and can manage device operation if impedance measurements fail impedance criteria by operating according to "improper impedance" rules. Defined operations can include, for example, setting a flag in the control module 40 to cause it to pause stimulation and/or provide a user alert (by controlling the stimulation module 42 and/or user interface module 48).

The progress module 47 tracks the progress of a user and goal achievement. For example, the module contains algorithms that calculate a first symptom score of the user at baseline (e.g., calculated using data obtained across 3 days before or after the start of therapy) using responses to surveys presented by the digital ecosystem module 50. The user is again surveyed at one or more later dates (e.g., day 14) and the results are used to calculate at least one post-treatment symptom score and at least one difference score comparing a baseline and a post-treatment score. If one or more symptom scores show improvements between the first and subsequent scores that are above a selected threshold, then defined operations occur such as the module may display a message about treatment progress "Congratulations: you have decreased your urinary urge incontinence score by x %". The module calculates and stores scores at different timepoints, calculates changes in scores compared to baseline, and displays these to a user as a history or trendline of the scores at preset times, upon user request, or according to a user achieving symptom improvement for a score that exceeds a minimum threshold.

The progress module 47 serves as a progress tracker that tracks and displays information to a user related to symptom changes or progress related to completing the treatment. A graphical representation of the steps required to be diagnosed and/or treated can show a user a status within the defined course of treatment. For example, a timeline can include initial consultation, completion of a baseline bladder diary or survey, a telemedicine diagnosis and prescription, onboarding, an induction interval, 1 or more timepoints for potential transition to maintenance, scheduled telemedicine or in-clinic visits, and any other defined therapy event.

The user interface module 48 provides subroutines and algorithms for operating, and responding to, the user interfaces (e.g., controls and displays) provided in the housing of the neurostimulator 12 or user device 20. The module manages user navigation through various menus and treatment screens of the user device 20, selection of features provided by the digital ecosystem module 50, and the entering of user input data. The module controls information presented to the user on the display at particular times (e.g., it can alternate between stimulation intensity and a timer value showing time remaining or elapsed time for therapy session. The module also assists in processing, adjusting, updating, and synchronizing operating parameter values in response to user input commands of a user interacting with the neurostimulator 12 or user device 20. The user controls 26 and display 30 of the neurostimulator 12 (shown in FIG. 1*b*) and touch sensitive display of the user device 20 are part of the user interface module 48 and allow user adjustment of the stimulation protocol parameters (e.g., amplitude of stimulation via intensity controls 26*a*,26*b*, field steering controls 26*c*,26*d* which provide spatial adjustment of the stimulation field at least along one axis of the stimulation matrix. Some information presented by the module includes a) session time remaining b) stimulation strength, c) stimulation field location for at least one axis, and d) remaining power. A touch sensitive display also allows for providing user input to control treatment characteristics.

In embodiments, a user interface module 48 provides a user with voice prompts for a set of survey items such as "Did you leak today?" which require simple user responses to be selected on the display of a user device 20, typed in, or spoken and recorded, transcribed, interpreted and perhaps confirmed (i.e., repeated back to a user), and added to a log. User input/feedback provided by a user is used to modify the therapy regimen. User verbal responses may be confined to 1 or 2-word answers such as a number (e.g., 1-10), or simple answers "Yes", "No", "Large", "Medium", "Small".

The matrix management module 49 provides the system with features related to identifying and using a stimulation matrix. It contains the date that the matrix was replaced and the amount of time or number of uses for which a matrix was used. It contains protocols for obtaining and validating the matrix ID information using a validation algorithm which may also utilize lookup tables, or by communication with a remote computer 20*f*.

The digital ecosystem module 50 allows the system to provide additional operations related to surveying of a user, adjusting treatment, promotion and assessment of compliance, remote telemedicine features and patient education, and behavioral training that supplements or enhances the benefits of stimulation therapy and additional features of the following ecosystem modules.

The virtual module 50*a* includes resources to support virtual or augmented reality features of the system such as those that can assist a user to align the wearable device in a similar position for separate treatment sessions. For example, if a user points the video camera of the user device at their leg, the software can superimpose a virtual device on the user's leg according to a prior placement that was known to be correct. The module can also contain modelling software that assists with visualizing a modelled stimulation field which can be presented to a user. For example, modelling software performs calculations on the stimulation signals that are provided by the channels of the stimulation matrix and generating a modelled vector stimulation field which can be graphically shown to a user (e.g., by "heat map" display of current density or other field parameter). In addition to simply illustrating the strength of the stimulation signals at each stimulation pad, the modelling software may also use information about the impedance, active/inactive channels, pad shape, and matrix geometry when calculating the vector field that is displayed to a user. The virtual module 50*a* also includes software that allows a user to select (e.g., tap on an area of a user device display) one or more regions of an anatomical representation of a user's body to indicate, for example, the lowest area where paresthesia is felt (see FIG. 9*h*).

The reference module 50*b* includes reference materials, videos and other content presented to, or accessed by, the user during an interval defined by the treatment regimen. The module also stores information such as photographs taken by the user. For example, if the system is first set-up for a user by a doctor then part of the onboarding process defined in the onboarding module 50*e* to operate a digital camera of a user device to obtain a picture the user wearing the neurostimulator 12. The user can view, or prompted by the user device 12 to view, this reference picture before a therapy session is provided at home to reinforce correct positioning on the leg.

The user groups module 50*c* includes resources that support a user interacting with a user group of individuals who also use the neurostimulation system including, for example, message board and chat access. Progress of other users who started at the same time as a particular user can be provided as a means of gamifying the therapy experience.

The telemedicine module 50*d* includes telemedicine capability including scheduling and connecting to remote medical support for providing videoconferencing or other remote support (e.g., chat). The telemedicine software may link to the user's smartphone calendar to allow them to set dates for events on the treatment regimen including telemedicine dates. In an embodiment, the system contains computer readable software code in the user interface module which operates with the other modules to manage telehealth operations and create a corresponding data log of a user's remote telehealth history. In addition to being scheduled, remote medicine visits can occur in response to a user response input when surveyed about whether they have any questions related to therapy. If a scheduled therapy session is set to occur then a "push notification" can be provided by the App 21, where user is asked if they want to have a remote session or be scheduled for an appointment (via scheduler or phone call). A positive response invokes a scheduling screen where a user can select a date and time for a remote session to occur, including immediately.

The onboarding module 50e operates to guide, train, survey and assist the user during their first use of the system to set up user preferences and establish a user profile. In embodiments the module provides a curated progression through a series of interactive screens that include providing instructions and exercises about proper system use, surveying the user about treatment goals, user information (e.g., age, coping strategies), user symptoms, user preferences, medical history, etc. The onboarding information is then used to create a user profile and to adjust therapy protocol parameters.

The survey module 50f, manages the scheduling and selection of survey items presented to a user during onboarding, induction, and maintenance treatment intervals. The surveying may occur using rules that are, for example, a) event driven (e.g., if a user indicated improvement of a subjective quality of life (QOL) measure then the system may provide further survey questions to obtain more information), b) logical (e.g., if the user indicates nocturia is not a problem the user will not be surveyed further on that topic at future times), or c) scheduled (e.g., a two week timepoint is reached and a post-treatment assessment should occur).

The user profile module 50g provides for storing and management of user profile information.

The coaching module 50h provides patient coaching and allows for the selection of, and adjustment in the schedule of coaching. Coaching includes modifying user behavior, cognition, or other attribute which can assist with providing improved outcome. Coaching includes providing educational content, reminders and "nudges" related to information relevant to a patient's treatment (e.g., neurostimulation and cognitive/behavioral therapy). The coaching module can be designed to prompt the user to take pictures prior to each at-home therapy session to create a visual log that can be reviewed by a medical professional to ensure the user has been placing the device correctly.

The alerting module 50j stores protocols and parameter values used by user notification operations for promoting compliance of stimulation treatment sessions or other treatment events.

The locator/connect module 50k provides features related to locating physicians who are familiar with the SAFN therapy and contains (or accesses remote) information such as physician profiles, distance from patient's location, patient ratings and comments, contact information and functionality for scheduling appointments or remote sessions. Can also filter information based upon a patient's insurance information and preferences (male/female doctor, alternative medicine specialization, primary care vs urologist, etc.).

The log module 50m is configured to create a log of all dates, times, and parameters related to the provision of therapy, device operation, or user input. The log may include timestamped data that allows the user to, for example, interact with the AE module 50n to create and store a photographic log to identify and track a potential skin condition ("skin events") related to use of the device. Algorithmic support for assessing the condition over time can assess features of the image related to the severity of the skin condition. Fields of a contact log can include the time and content of any user messages that users may send to/receive from a remote computer 20f of a remote medical service (e.g., Q&A between a doctor and the user). Additionally, the contact log can store any information related to user provided "event tagging" which may include voice recordings or text messages which are transmitted to a remote computer 20f for review or which are stored on the device for later upload and review by a medical technician. The communication module The adverse event (AE) module 50n is configured to provide users features related to identifying, reporting, logging, tracking and avoiding potential adverse events that may be related to the treatment such as skin reaction events (e.g., redness, soreness, bruising, etc.). For example, if during the onboarding process a user indicates their skin is prone to irritation then the module can set a reminder to occur prior to therapy session and instruct the patient to alternate the leg on which the device is worn, limit the therapy to a selected duration, apply a moisturizing cream after the session, etc.

Rules and algorithms module 50p is accessed by the control module 40 and stores and implements rules and algorithms of the system 10a. Rules define what occurs according to an operating parameter is set to a particular value. For example, if a skin risk score variable is set at defined value then skin risk operations are provided by the treatment program. Rules can implement operations contingently based upon various thresholds being met or exceeded. The algorithms are used to calculate results that guide system operation. The rules can also access operations defined in look-up tables for defined events so that users are provided with appropriate therapy events. When users provide ranked scores, then rules can be used to operate on the scores to select one or more montages for therapy.

FIG. 2 shows a neurostimulator 12 and other components of the system 10a with which it communicates. For example, the neurostimulator 12 can receive input from user devices 20 such as a smartphone 20a (or tablet running Android or iOS, and an "App" 21 that supports all features of digital ecosystem), smartwatch 20b, laptop or tablet computer 20c (of the user or a doctor), a remote laptop or computer of a telemedicine service 20c', a specialized "remote control" 20d device (e.g., only having controls for therapy regimen parameter values to be controlled and communicated to the stimulation device 12, or also having a display of therapy parameters), an virtual assistant AI technology (e.g., Alexa—type) device 20e, a remote computer 20f that provides data storage and other functionality. The remote computer 20f is understood to be a server computer that may operate as part of at least one "server farm" or "data center" that is connected to the internet and enables remote support of the neurostimulator 12. The remote computer 20f resources are programmed to provide the features that are disclosed herein including providing remote resources as is well known in the art.

The device 12, user device 20, or other system component is configured for 2-way communication with remote computer resources 20f of a center that provides automated or human-based review of patient data, telemedicine support for users, and other disclosed ecosystem features.

The neurostimulator 12 can be used alone or in combination with user devices 20a-20f. In an embodiment, the control module 40 of the neurostimulator 12 can be set in a "device-only" or "stand-alone" default mode which is not toggled to a "user-device" mode until a user device 20 establishes communication with the neurostimulator 12. This can occur at the first time use, and a user must confirm on a user device 20a-20f that they wish to routinely operate the neurostimulator in combination with one or more of the user devices 20 during therapy, or can occur thereafter. In an embodiment, the user device 20 is a smartphone 20a operating under control of a software application or "App" 21 that is uploaded to run in the operating system of the user device and enable a wide array of functionality. The App 21 provides a user interface to control the neurostimulator 12, provides user alerts related to scheduled therapy sessions, presents survey items that a user or medical professional completes to customize a therapy regimen, and provides a plurality of additional features of a digital ecosystem as will be disclosed. Alternatively, the user device 20 may be configured with limited functionality such as only displaying a few virtual controls to toggle between a power ON, power OFF, stimulation pause/restart; and to adjust stimulation parameters such as intensity and predefined sets of active channels of a stimulation matrix. In an embodiment, if the user device 20 is realized in a simple embodiment with few controls and features then additional functionality and features (e.g., presenting surveys and permitting user input) is provided through a web portal, or by a user filling out and mailing or e-mailing surveys to a processing entity which enters/scans the information into a remote computer resource 20f of the web portal. The web-based portal hosts a remote computer 20f to allow user creation of an account for completing survey items and interacting with a web interface for personalization and customization of their therapy program. The information entered in the portal can be operated upon and then communicated to the neurostimulator 12 or one or more of the user devices 20 to customize the therapy regimen.

In embodiments, the user device 20 is realized as user's smartphone 20a running an App 21 that is configured to alert the user with the speaker (auditory alert), vibration (vibrotactile alert), or display (visual alert) of the smartphone under control of the user interface module 48 functionality provided by the App 21. The visual notifications may be push notifications presented by the App 21, or can be provided as text messages or e-mails which are provided via the App 21 or which are scheduled to be sent from a remote computer 20f. The App 21 can also be designed to display a dashboard that allows a doctor at a remote service to use a remote computer 20c' to communicate and monitor/control a neurostimulator 12 of a particular user. When the portable computer 20c' is used as a dashboard, its control module 40 communicates with the control module 40 of the neurostimulator 12, and the dashboard is displayed and interacted with under control of the user interface module 48. When a portable computer 20c' is used by a physician to monitor and adjust stimulation parameters of a set of one or more remote patient neurostimulators 12 it can communicate directly with the neurostimulators or can operate in conjunction with a server computer 20f which contains information about at least one set of neurostimulators 12. The user device 20 may also be realized as a custom remote-control device 20d with or without a display with customized function buttons for controlling the stimulation intensity and adjusting location of active channels as well as circuitry for providing alerting and user interaction. The user device may be realized as a voice-based virtual assistant AI technology such as an Alexa device 20e with software modules that can control an entire smart device ecosystem. The Non-invasive Neuromodulation Assistant (NiNA™) module is an Alexa "skill" (i.e. function defined in a library) that can be installed and activated by a user and is programmed to provide functions such as, a) provide reminder alerts, b) allow the user to initiate a treatment session, c) provide commands during a treatment session such as those that control the stimulation waveform (e.g., "Alexa—increase intensity", "Alexa—pause stimulation") d) provide commands which change the location of the stimulation field according to at least one defined series of pre-set stimulation montages (e.g., "Alexa—move stimulation to the left"). A remotely connected server computer 20f that provides a computer resource that in turn can communicate with remote laptops 20c operated by doctors, clinics, medical services, or a manufacturer and which provides, for example: a) data storage for at least one set of one or more neurostimulator devices, managed by a memory module 43 or b) a web-portal accessed by users over the internet via the user interaction module, c) virtual user control and communication with neurostimulators 12 permitting viewing of summary statistics for 1 or more sets of neurostimulators to be displayed on dashboards. In embodiments, the neurostimulators are configured to communicate with a remote computer 20f either directly or by way of the user device 20a according to start-up and shut-down routines of the control module 40 which occur at the beginning and end of each treatment session, or as operations defined when switching between a low-power standby OFF state and an ON state (e.g., to upload log data or obtain permission to provide a therapy session).

Stimulation Matrix.

FIG. 3a shows an embodiment of a stimulation matrix 14 comprising 6 stimulation pads 16 on a flexible backing 51 realized using an electrically non-conductive substrate. In embodiments, the stimulation matrix 14 is realized using a re-usable assembly of electrodes each with conductive hydrogel pad 16 for contacting a patient's skin and delivering electrical stimulation. The stimulation pads 16 have conductive material that provides the stimulation signal to a user's skin and can also be termed "electrodes" or "electro-conductive pads". The skin-side view of the matrix 14 is shown on the left side of the figure with a first set of 3 pads on its top half (properly located more proximally along the limb when the system is oriented correctly) and a second set of 3 pads on its bottom half (property located more distally along the limb). Each set of pads is arranged in a geometric formation having a mathematical triangular envelope defining a triangular configuration with the apex of the two triangles residing at proximal and distal ends of the matrix 14, respectively. When secured to the user's leg below the knee the top half of the matrix 14 is closer to the knee and bottom half is closer to the feet. When a stimulation matrix 14 is secured to a user's limb such as a user's arm for treatment of arm pain or for modulation of arm nerves (e.g., median, ulnar, radial nerves) for treatment of unwanted medical symptoms/conditions, then the top half is closer to the shoulder and bottom half is more distally located and closer to a user's hand. The three stimulation pads 16 of the top half each have an electrical conduit 54a, 54b, 54c that routes stimulation signals to these from a hub 56 which in turn travels through the backing 51 and connects with a stimulation matrix connector 62*a* at the top side of the matrix. Alternatively, signals can be routed to pads individually without the use of a hub, or a single hub can be used for all pads of the matrix 14. In the shown embodiment, the top stimulation matrix connector 62*a* is a proprietary design containing 3 male plugs that route electrical charge and mate with a connector (not shown) having 3 female receptacles that are provided on the bottom housing of the neurostimulator 12. A portion of either connector 62*a* or 62*b* may be magnetized to improve connection to the bottom housing of the device 12. The connectors for the lower half of the matrix (which correspond to those of the upper half) are not labeled as 54*d*, 54*e*, 54*f* to avoid cluttering of the figure and are connected to the bottom half stimulation connector 62*b*. Labeling 64 which may include the words "top" is located opposite to the matrix connector 62*b* to provide the user with a visual marking that guide correct connection/orientation of the stimulation matrix 14 to the device 12. In an alternative embodiment, the top and bottom stimulation matrix connectors 62*a*, 62*b* may be shaped, or oriented, to require that the matrix 14 is correctly oriented when connected to the neurostimulator device 12 (i.e., forming a "keyed" connector as shown in FIG. 1*c*).

In embodiments, the matrix 14 uses stimulation pads 16 created using a conductive hydrogel or metal alloy. Pads can be used with electroconductive gel or can be a "dry electrode" for transcutaneous electrical stimulation. In an embodiment, the matrix is formed with a conductive backing layer having stimulation pads 16 residing on the conductive backing layer which are configured to make skin contact and deliver electrical stimulation from the conductive backing to the skin. The stimulation pads 16 which contact the skin can be made of polymer, plastic, or rubber material with a conducting material typically provided evenly throughout and having a thickness of between 1 mm and 10 mm. The conductive material can be loaded with single wall carbon nanotubes or other conductive substrate.

In an embodiment, the stimulation matrix 14 is a hydrogel electrode array assembly having 6 stimulation pads 16 having a size and shape suitable to be applied on the skin of the medial surface of the leg over the SAFN and supplied with stimulation signals configured to improve the chance for obtaining desired characteristics of the vector stimulation field such as being of physical dimensions that are well suited for a user's leg and: a) are sufficiently narrow, and not wider than necessary, to decrease the risk of unwanted stimulation of calf-muscle or non-saphenous nerves; b) are sufficiently wide to provide a sufficient range across which a field's location may be controlled to successfully obtain nerve recruitment; and, c) are of sufficient length that the pads are separated enough to create a field with an adequate depth to stimulate the subcutaneous target nerve. Additionally, the pads 16 are of sufficient size to provide comfortable and safe current densities and deter the risk of unwanted cutaneous nerve activation and sensation of pain/discomfort. The matrix 14 is realized with each pad comprising silver-electrodes on a flexible PET substrate, covered by an adhesive hydrogel layer that reduces electrode-skin impedance and typically includes adhesive to promote connection to the user's leg. In embodiments, the matrix 14 is realized using stimulation pads 16 arranged in a defined geometric pattern each of which may operate as active, return, or ground and may be independent current sources that permit user control over the stimulation field geometry. In an embodiment, at least 3 pads are used corresponding to at least 3 stimulation channels.

In embodiments, the stimulation matrix 14 is re-usable and permits a limited number of treatment sessions. Sessions can be tracked and limited to a permitted amount by the matrix management module 49 of the neurostimulator 12 one or more user devices 20. A connector 62*a* on the top side of the matrix 14 engages a connector portion 34*a* on the bottom of the stimulator housing and provides an electrical interface with the stimulation channels of the stimulation module 42. As shown in FIG. 3A, the connector 62*a* also includes an electronic ID chip 37 that the system 10*a* uses to: a) confirm that the matrix is an authorized product of the company: b) track the number of times the matrix has been used; and, c) obtain the date of manufacture to ensure the matrix is not too old. The ID chip 37 can contain memory storage and the matrix management module 49 can read and/or write a parameter value associated with the number of stimulation sessions (or days) the matrix has been used. The system can read/write a valid or stale "flag" value in the chip 37 or in other memory structure of the system, depending upon usage criteria. The matrix management module 49 of the device 12 is configured to read and assess the ID chip 37 and disable the device or the matrix 14 if a specified usage criterion is met (number of valid treatment sessions, maximum interval based upon date of first use, etc.), or present a message to a user, or send (or prompt the user to authorize the sending of) a purchase request to a remote computer 20*f* to cause a new matrix to be purchased and shipped to the user. The usage criteria can be assessed based upon data stored in the ID chip, the neurostimulator, the user device, or a remote computer 20*f*.

In embodiments, flexibility of the matrix pad 14 is improved by providing gaps/slits 60*b* along the outside areas of the backing 51 that allow it to bend and conform to the contour of a limb to which it is applied. The backing 51 has alignment slits 60*a* which can be asymmetrically or otherwise shaped or located along the circumference to require correct alignment between the backing 51 and the device bottom housing 24*b*. Only one edge of the stimulation matrix or matrix 14 may have an alignment slit 60*a* that engages a peg of the device housing (not shown) to provide correct orientation of the stimulation matrix 14.

In an embodiment, the predetermined arrangement of the stimulation pads 16 of the stimulation matrix 14 includes defined angles and spacing between 3 or more stimulation pads that define 3 stimulation circuits. In one preferred embodiment the matrix 14 includes an upper set of 3 stimulation pads 16 on its upper half, and a lower set of 3 pads on its lower half. The upper set of pads 16 has horizontal offset between pad edges or centers (but not necessarily be in a triangular arrangement). A lower set of pads can have a similar arrangement, or the two sets of pads may have different inter-pad spacings.

In a further embodiment shown in FIG. 3*a*, the top half of the stimulation matrix 14 is realized using at least two rows of pads 16, with a central pad that is horizontally offset (overlap) such that there is horizontal overlap with the adjacent pads of a lower row. This arrangement is termed an "overlapping triangle" configuration. The center pad of the first row is vertically offset in relation to the adjacent left and right pad that form the base of the triangle. A pad arrangement provides adjacent pads that are diagonally offset from each other to form a triangle (with one pad at the apex and the other 2 pads forming the base) provides advantages of: a) a reduced width stimulation matrix 14 relative to that which results when all 3 pads are aligned horizontally and located along the same row; and, b) the combination of horizontal overlap of adjacent pads and vertical offset that covers a larger area than a single row increases the chance for nerve recruitment compared to that which occurs with 3 pads on the same row. The overlapping and narrowing design may be extended to rows with an additional number of rows or pads (e.g., 3 to 5 pads). While a stimulation matrix design may also incorporate rows having more than 5 pads, this may increase complexity of use and cost of the manufacturing of the matrix 14.

Although many stimulation montages are possible using 6 channels of stimulation (any of which can serve as anode or cathode or inactive at a particular moment in time), an advantageous strategy is to utilize a set of 3 stimulation circuits, each arranged vertically between the top and bottom portions of the stimulation matrix and include the 2 leftmost pads, the 2 center pads, and the 2 rightmost pads.

An extracorporeal stimulation matrix with fixed stimulation pad positions and electrical field steering has not previously been created to the knowledge of the inventors. When field steering is realized in combination with using a stimulation matrix comprising a three pad "triangle" configuration several advantages are realized. First, the size of the matrix pad can be decreased to that realized with identically spaced rows of pads since the top pad of the triangle's apex and the bottom pads of the base row of the triangle are offset so pads of adjacent rows have horizontal overlap. Secondly the triangular configuration allows for adjustment of the location of the stimulation field along both the horizontal and vertical axis of the matrix. For example, the stimulation montage shown in FIG. 6b produces a longer vertical field, than FIG. 6h (white="active"/ grey="inactive"). Further, relative to FIG. 6h, FIGS. 6i and 6j produce fields that vertically extend lower, and higher, respectively. The use of only 6 pads, configured in two sets of 3, each with a triangular geometry, allows for left/right and up/down spatial adjustment of the stimulation field. Diagonal circuits provide additional field geometries to those realized with strictly vertically oriented activation patterns. Diagonal stimulation fields may increase the chance of entraining a nerve travelling up the leg along the axis and that is not directly under any of the activated stimulation pads. Examples of diagonal stimulation circuit are shown in FIGS. 6d and 6e.

The combination of: a) an arrangement of two sets of stimulation pads of a stimulation matrix, with each set having a fixed triangular geometry; b) use of field steering; and, c) proper anatomical placement of the stimulation matrix as guided by detailed instructions provided to a user using both video and text support, provides the stimulation matrix 14 with advantages of: i) a reduced footprint compared to non-overlapping pads; ii) provision of adjacent stimulation circuits that have increased chance of vector overlap by adjacent stimulation fields, and iii) improving the ability of the stimulation matrix to be used with subjects having a larger range of lower leg circumferences (and lengths) while providing an improved chance of reliably delivering therapy to a target nerve.

The stable geometry of the stimulation pads of the stimulation matrix can provide improved control of vector stimulation to that which would be achieved with a set of conventional stimulation pads connect by wires and manually arranged by a user. The fixed matrix may provide better targeting of beat or other vector fields at a target nerve due to a stable, repeatable geometry of stimulation being applied at the skin surface.

The inventors also evaluated a non-overlapping linear arrangement of pads, where the middle pad was not offset, and 3 pads formed a single row. Not to be limited by theory, the triangular overlap arrangement appears to have the following advantages: a) was preferred by subjects, b) may decrease the risk that a nerve will lie between the stimulation fields created by pads arranged with "horizontal" gaps between the pads, c) increases the vertical range of the stimulation field which increases the chance that the field will intersect a branch of the target nerve, relative to using a single row of pads that may be below a portion of the target nerve, and d) decreases the width of the matrix. A wider matrix 14 will extend further around the leg circumference and provide disadvantages because it may: a) increase the risk of recruiting muscle, b) target other nerves in the leg in addition to the SAFN which may limit tolerable amplitude or cause foot motor activity, and c) provide a worse fit for people with thinner/smaller legs. When a single top and bottom row was tested on a group of subjects disadvantages were observed such as less reports of robust nerve recruitment and increased reports of self-reported calf-muscle activation, discomfort, and spasm. Some other arrangement such as a single row, or two rows of pads linearly arranged on each of the upper and lower matrix portions offer some type of advantage for field steering or shaping (e.g., an array of many smaller sized pads to provide a more granular control of a stimulation field). However, when using sets of 3 stimulations pads 14 on the top and bottom, an overlapping design appears to hold advantages.

In an embodiment of the matrix 14 shown in FIG. 3a, the top set of pads is realized using 3 pads each of which has about 1.0 to 1.5 square inches of electroconductive surface, realized as a rounded rectangular, square or somewhat circular contour. In an embodiment, the matrix pad 14 is realized as a disposable component of the system. The flexible backing is made of Polyethylene terephthalate (PET) or Polyimide substrates, printed silver, dielectric insulation and the pads made of foam, non-conductive and/or conductive hydrogels, Hydrogel and scrim assemblies which can be constructed as hydrogel formed dots or pads configured on a scrim of finely woven, nonconductive mesh of polyester, nylon, polyamide or similar material.

In an embodiment, the matrix 14 is realized as an upper and lower half which are formed separately, and independently connect to the neurostimulator 12 so that each half can be independently replaced to reduce the cost of replacing the entire matrix 14.

Figure 7D:
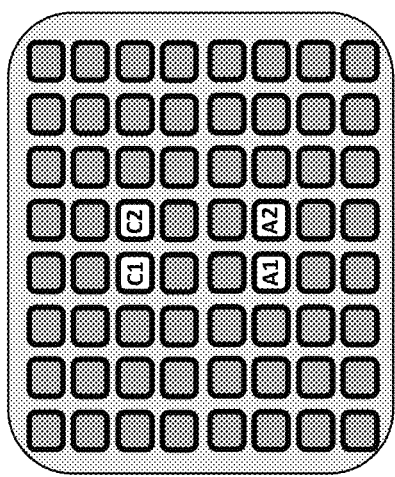
FIGS. 7d to 7e show stimulation matrix grid arrays having 8 rows of pads.

While not being limited by theory, although the stimulation matrix may have many more stimulation pads (e.g., 10, 50, or 100), a peripheral stimulation wearable device which is configured for the arm or leg realizes many of the benefits and therapeutic efficacy disclosed herein while preferably using a first stimulation array that is not more than 3 pads and a second stimulation array that is not more than 3 pads. In the stimulation of the SAFN, this suggests that stimulation matrix designs that are cost-effective and not overly complicated to use are preferably realized using 6 (i.e., 2 sets of 3), 7 (see FIG. 7c) or 8 (see FIG. 7b) pads, and not more than and 18 (i.e., 2 sets of 9) stimulation pads. The cost and complexity stimulation matrix designs using a larger set of pads may be merited when sensing or other features are incorporated.

FIGS. 4a-4d show 4 patterns for the stimulation pads 14a-14d which were assessed in a group of subjects. One part of the assessment entailed determining if the movement of the field location from the left to the right side of the pad surpassed the subject's just noticeable difference (JND) threshold for detecting the change. Another part of the assessment included asking about the comfort of the perceived stimulation and ability for subjects to detect SAFN recruitment. The first pattern shown in FIG. 4a was assessed as preferable since it allowed subjects to more easily feel the movement of the location of the stimulation field related to 3 different zones (left, center, and right) and also allowed them to provide a clearer confirmation of nerve recruitment. FIG. 4b shows an alternative embodiment with the top and bottom halves of the stimulation matrix 14b having a different number of stimulation pads (i.e., only 1 stimulation pad on the bottom half and 3 pads on the top half). Stimulation with this configuration may be realized with the bottom pad serving as one anode channel which completes a circuit with one or more of 3 cathodes, or vice versa. This more minimal design also allowed for field steering, but had the disadvantage that the movement of the field was not as evident to some subjects and the SAFN recruitment did not occur as reliably according to their subjective reports. Further, when the single pad was used as an anode, this suffered the disadvantage that it produced anode dominated stimulation and the stimulation was mostly felt under that pad, likely due in part to the larger current density at the anode. Accordingly, this matrix design might necessitate the need for increasing (e.g., triple) the size of the anode surface area to prevent "anode domination" (i.e., the subjective sensation being dominated by the sensation near the anode) and would result in coarser field steering than that obtained using the design of FIG. 4a.

FIG. 4c shows an embodiment where the stimulation pads of the stimulation matrix 14c are larger and closer together than in FIG. 4b. This design, with decreased space between electrodes, also appeared to have the disadvantage of diminishing the user's ability to perceive changes in the location of the stimulation field when the bottom electrode paired with any of the upper 3 stimulation pads. Compared to FIG. 4a and FIG. 4b, there is more overlap between the fields created between the circuits which included bottom pad and any of the 3 pads at the top of the matrix. Lastly circular pads were also assessed using the design shown in FIG. 4d, since these could potentially allow for a more compact stimulation matrix 14d design. This did not appear to offer an improvement in subjects' ability to confirm the movement of the stimulation field (assessed by verbal report) of the electrical field, when compared to a geometric arrangement consisting of the rounded square pads (FIG. 4c). An advantage of the invention is to use stimulation parameters and matrix characteristics (e.g., the horizontal offset of adjacent pads, space between the pads) that permit a majority of users to perceive a change in stimulation field's location when adjacent circuits are selected. It is likely that pads located on adjacent rows should have less than 50% overlap to allow users to distinguish horizontal movement of the field.

The stimulation matrix design may be influenced by several potential tradeoffs between increasing the compactness (e.g., overlap of pads) or complexity (e.g., using many pads) of the arrangement of pads on a matrix and increasing "reliability" for at least: a) the ability of a user to discriminate between different field steering settings; and, b) successful or robust recruitment of the SAFN. A design that is too compact may also increase the risk of electrical shorting between pads as the edge-to-edge distance of adjacent pads is decreased. Not to be limited by theory, to avoid shorting the smallest edge-to-edge distance may range between 0.1 and 1.0 inches, and preferably about 0.1 to 0.3 inches, but should typically not be less than about 0.1 inch. When applied to the lower leg, the stimulation matrix pad width is about 3-inches, and the height (cephalocaudal axis) is about 6-inches. In an embodiment, three different sized matrix pads are used to accommodate a large proportion of the population, and are 75% and 125% of the height and/or width dimensions shown for the pad in FIG. 4e. The stimulation matrix 14 may be provided as a single portion or as two halves which are independently secured to the bottom of a housing of the neurostimulator device 12.

While the examples shown in FIGS. 4a-4e used 4 or more stimulation pads, in embodiments, field steering may be accomplished using a set of only 3 stimulation pads. While this design could be used with the features of the invention, it was not tested. However, it would likely be preferred less by subjects similar to the reasons already discussed. A minimum set of pads that will enable field steering can comprise 3 stimulation pads which are realized, for example, as 2 cathodes which are horizontally displaced with respect to the axis of the limb, and positioned proximally to 1 anode. In this example, field steering may occur by selectively and fractionally activating a combination of the 3 pads, where the amplitude of the signal between cathode 1 and anode 1 for a 100 mA signal is set to 90% (90 mA) and the signal between cathode 1 and anode 2 is set at 10% (10 mA). When two pads are referenced to a common stimulation return pad then the two stimulation source pads can each be driven by outputs of a stimulus generator while the common stimulation pad is connected to the return side of both stimulus generators, and the tissue between each channel serves as the two loads of the electrical circuits. In an embodiment, using the weights defined by a look-up table will assign a greater weight value for the first cathode or the second cathode to determine if the stimulation field is located more on the right or left side of the stimulation matrix.

Neurostimulation Protocols and Programs

FIG. 3a shows a stimulation matrix 14 which has 6 stimulation pads which may be assigned to serve as a cathode, anode or inactive channel. When restricting the provided stimulation to the top 3 pads the number of possible permutations of different channel combinations is manageable (e.g., left pad is anode and right pad is cathode; left=anode and center=cathode; left=anode and center and right pad=cathode, etc.) and may be under twenty. However, if the different channels can use different amplitude weighting values (e.g., left pad=100 mA (Anode), center pad=70 mA (Cathode) and right pad=30 mA (Cathode)) then the number of possible combinations becomes very large, even when restricting to a few different sets of weights. Further, if the set of lower 3 pads is added to permitted stimulation protocols then the number of combinations grows to be unmanageable. Adjustment of stimulation parameters by a patient (or even a doctor) can become too complicated and time consuming to be practical. Providing unconstrained freedom in adjusting the stimulation protocol cause many problems.

The SaphLocate feature of the invention uses a limited number of selected stimulation montages that are adjusted or selected by controls and methods to enable users to assess different candidate stimulation montages in a simple, user-friendly, and time-efficient manner.

SaphLocate permits the location and shape of the stimulation field to be easily and intuitively adjusted by a user and for a limited number of combinations of active channels to be assessed. In embodiments, one SaphLocate program will only permit the location of the stimulation field to be adjusted along the horizontal axis of the stimulation pad. SaphLocate can also provide the user with a limited number of candidate montages related to adjusting the depth of stimulation.

In embodiments, the SaphLocate feature also provide adjustments to the stimulation field according to settings which are designed so that user adjustment to field location meets a sensory criterion such as a) being perceived by the user or b) being devoid of large perceptual jumps in intensity. For example, the montages associated with providing different field locations are set to be above the just noticeable difference of at least 50% of a group of subjects.

The SaphLocate features enables users to compare candidate stimulation montages and select a preferred montage for treatment. The preferred montage can provide at least one advantage such as improved nerve recruitment, improved comfort, or decreased risk of unwanted stimulation of non-target tissue such as muscle. SaphLocate enables improved selection of stimulation protocol used during treatment. When used for non-SAFN targets, this may be termed "NiNALocate"

Additionally, the NiNA system provides SaphLevel features which enable advantages for users when adjusting and selecting an amplitude level and waveforms to be used during stimulation treatment. SaphLevel features provide users with advantages such as a better sensory experience of the stimulation, improved nerve recruitment, and enabling higher intensity stimuli to be tolerated by a user.

Accordingly, SaphLocate and SaphLevel features provide advantages of, for example: a) a limited set of stimulation montages, b) stimulation montages that provide improved sensory experiences to users, c) stimulation montages that provide improved targeting of a nerve, d) a defined series of stimulation montages that define a how the current stimulation montage is followed by a subsequent montage, e) a defined series of montages with weighting values set to permit a smooth perceptual transition of the a characteristic of the stimulation field such as shape or location.

The SaphLevel™ features of the invention provide advantages with respect to adjusting the intensity level of a stimulus and its corresponding subjective experience and ability to modulate a target nerve. The SaphLocate™ features provide advantage with respect to adjusting the location or geometry of the stimulation field. SaphLevel and SaphLocate features may use similar weighting values and strategies, but for achieving different advantages.

The SaphLocate and SaphLevel features of the system may both rely, at least in part, on technologies that allow the field geometry, location, and intensity settings to provide improved therapy or improved patient experience in relation to: a) providing limited and targeted adjustment of the stimulation field location and geometry during initial assessment and selection of candidate stimulation fields which can be subsequently used during provision of therapy; b) enabling easy user assessment of different stimulation fields during this initial adjustment; and c) providing advantages for the stimulation field used during the treatment session related to improved comfort and nerve recruitment.

In an embodiment the limited set of stimulation montages includes defining a set of 3 pairs of active channels defined as left, center, and right, and assigning weights to each of the three circuits that permit the stimulation field to transition in a distinguishable and smooth manner with respect to the perceived strength of the stimulation field, from the left to the right region of the stimulation matrix.

When the stimulation is largest at the center pair of channels then those are considered to define the "primary channel" and the Left and Right channels are non-primary. In general, the primary channels are those with the largest amplitude (i.e., highest weights) and the "non-primary" circuits or channels are assigned lower weights or are inactive. One of the SaphLevel features is to provide lower weights at non-primary channels to produce at least one advantage over what would occur if the non-primary channels were simply deactivated.

In embodiments, SaphLocate controls only permit the location of the stimulation field to be adjustable along a left/right axis of the matrix. In an embodiment, the adjustment along the left/right axis is provided using a limited series of stimulation montages that have been shown to enable recruitment of a target nerve such as the SAFN in group of subjects or that have been shown to enable smooth and discernible transitions between montages. Additionally, the series of montages can also have a set of predefined allowable transitions between adjacent stimulation montages (i.e., the user cannot "skip" a pre-defined stimulation montage—and corresponding set of channel weight values—as is defined in a series of at least 3 adjacent montages defined in a lookup table). In an alternative embodiment, two "diagonal" montages are also provided in the limited set of stimulation montages which use two stimulation channels selected from different columns of the matrix. In an embodiment, SaphLocate does not include montages with stimulation circuits that are approximately horizontally oriented fields which are separated by less than a selected distance since these will have corresponding field paths that are typically shallower.

In embodiments, the stimulation signals are adjusted using the SaphLocate features of the system that improve a user's ability to compare and select stimulation protocol settings related to geometry of the stimulation field provided by the matrix 14 through the user's skin. SaphLocate features include: a) adjusting the shape of the stimulation field by changing the geometry of active stimulation channels provided by a limited number of arrangements of stimulation pads during therapy, b) steering the stimulation field by changing the geometry/and or the amplitude and/or designation (anode/cathode/inactive) status of a pre-determined set of montages for the stimulation pads, and c) providing stimulation intensity settings that are "weighted" for each geometry of a set of stimulation geometries so that transitions between different combinations of active stimulation pads, and corresponding movement of the stimulation field, occurs smoothly without unwanted jumps in actual intensity or perceived intensity.

In embodiments, the treatment uses stimulation settings with various SaphLevel features that provide advantages when determining settings related to stimulus intensity and nerve recruitment. SaphLevel features include a) guiding a user to select stimulation intensity levels that sufficiently recruit the target nerve but are below a level which is painful to a user, b) reminding the user to re-adjust the intensity part way through the treatment session to compensate for any adaptation that may have occurred and which can allow the stimulation to be set higher, c) providing stimulation intensity settings that are "weighted" for a selected matrix geometry so that the sensory experience of the stimulation is "richer" and potentially less painful (as may be predicted by gate control theory) and, d) additional features as will be disclosed. A "richer" perception of the stimulation as was described by users as less sharp, "prickly", and point specific than occurs with two channel stimulation was provided without activation of non-primary channels and was experienced as less "piercing" with a more rounded stimulation-induced pressure sensation. The SaphLevel features can also include guiding or surveying the user to ensure that suitable stimulation strength and stimulation channels are used. For example, questions are presented to a user to confirm the intensity of the stimulus is sufficient to modulate the target nerve, to decrease unwanted muscle stimulation, or to improve perception of the stimulation.

Ambulatory Therapy Facilitation by SaphLocate/SaphLevel.

The SAFN is a sensory nerve and targeted stimulation will evoke a sensory response devoid of a motor response that characterizes, for example, PTN stimulation. If SAFN stimulation selectively modulates the SAFN with little or no co-activation of calf muscle or nearby motor nerve recruitment, then the user should be able to be ambulatory during stimulation treatment. This may be true even if the stimulation protocol produces moderate or strong paresthesia. When the risk of unintended motor/muscle response is low, this also decreases associated risks such as muscle tear, unwanted foot activity (i.e., contraction), uncomfortable muscle twitching, or trouble with ambulation. Similarly, the risk of losing control when using the foot to operate a gas or brake pedal of a car is decreased. Accordingly, targeted SAFN in which the field is constrained (e.g., by field steering or by selecting an appropriate stimulation montage) to avoid/minimize coactivation of unwanted tissue or nerve targets, can allow users to engage in activity even while stimulation treatment is provided. Since SaphLocate and SaphLevel can help to decrease risk of unwanted muscle stimulation by allowing a better selection of the stimulation parameter, these can increase the ability of users to provide therapy while ambulatory.

Additionally, the evaluation of sensed data (e.g., accelerometer or EMG data) can be used to adjust stimulation parameters (e.g., decrease stimulation amplitude) by the SaphLevel algorithm if these data indicate the user is engaging in activity above a selected threshold. For example, while slow walking is allowed, walking above a selected speed causes stimulation to halt, decrease stimulation amplitude, or pause for a defined interval or until accelerometer data again shows the user is less active. Improved targeting of the SAFN which allows stimulation of the SAFN with less unwanted co-activation of other nerves or muscles in the leg can be achieved by at least one of: a) field steering; b) selecting a location that does not stimulate another nerve in the leg; c) selecting a location in the leg that does not stimulate the calf muscle; d) using two or more stimulation pads of a matrix located on the medial aspect of the leg at locations that do stimulate the SAFN but not directly stimulate the sural nerve, posterior tibial nerve, tibial nerve, peroneal nerve, or any of the plantar nerves; and, e) providing stimulation using two or more stimulation pads that create a current path that is aligned with the axis of the limb (i.e., vertically offset so that one pad is more proximal and the second pad is more distal), and the stimulation protocol is adjusted to provide targeted stimulation of the SAFN.

FIG. 3b shows a touch sensitive graphical user interface (GUI) display 70 of a user device 20a that has a default therapy session screen displayed during treatment. In the illustrated embodiment a timer 72 shows the time remaining in a treatment session using both a numerical value and a graphical representation of a proportion of the total 30-minute treatment session time that has elapsed. While a 30-minute therapy session is shown, session duration may be, for example, a duration between 15 and 90 minutes. In embodiments, several sessions (e.g., 1 to 3) may be scheduled in a single per day.

Virtual controls allow user control of stimulation signal characteristics including a "Stop" control 74 that pauses the stimulation treatment (e.g., the intensity is set to zero and the timer stops incrementing), two intensity controls 76a,76b include a plus "+" and minus "−" symbol that increase and decrease the stimulation intensity, respectively. Additionally, a field steering manager interface 78 provides SaphLocate features such as a left and right control 80a,80b that moves the stimulation field from the left to right side of the matrix using a predefined series of stimulation montages. Using proper amplitude weights for the stimulation montage can allow adjustment of the geometry or location of the field to occur in a smooth manner that permits user to perceive the movement of the field's location. A field location display 82 of five circles are highlighted as the field moves from left to right. When worn around the upper calf this may move the field from an anterior region near the tibia to a posterior region of the leg, or vice versa, depending up on the leg on which the matrix is worn. In embodiments, a SaphLocate features provide a field location display 82 on the display screen of the neurostimulator 12 and/or user device 20a to reinforce the user's perception of the adjustment of the stimulation field.

In embodiments, as will be disclosed, the field steering manager interface 78 can be selected (i.e., double tapped) to expand to include additional "advanced" controls for adjusting characteristics of the stimulation field such as the horizontal or vertical center of the field, adjusting the number of montages that are used to move the field from a first to a second location (e.g., from left to right) or allowing the user to adjust if a set of one or more stimulation pads serves as anode, cathode, or is inactive. As disclosed, control of individual channels may typically be too complicated for most users. However, in some instances turning off a single stimulation channel may be useful, such as making the lower right or left stimulation pad inactive to attenuate unwanted calf-muscle activation. In the case where a stimulation channel is deactivated, the SaphLocate algorithm can adjust the remaining active channels so that the anode/cathode charge delivered from the matrix remains balanced.

In the shown embodiment, SaphLocate is realized with left and right controls permit selection of a stimulation montage from a set of 5 discrete field montages defined along the left-right axis of the stimulation matrix. Each of the 5 defined "zones" has an associated location label such as: Left, Center-left, Center, Center-right, and Right. Additionally, an "All" setting causes the stimulation field to be provided approximately with the same amplitude across all zones. In this example, the matrix of FIG. 3a will be used although other arrangements of stimulation pads could alternatively be used. If the stimulation pads of the matrix 14 are conceptually arranged as rows and columns, then three columns of electrodes exist, and the On(1)/Off(0) status for each column created for these 5 stimulation montage and the "All" montage may be defined in a simple embodiment as: [1 0 0], [1 1 0], [0 1 0], [0 1 1], [0 0 1], [1 1 1], respectively. In FIG. 3b, the user has selected the Center-right zone which causes the stimulation signal to be provided by 2 pads at the center (apex) and 2 pads on the right side of the triangle arrangements of the stimulation matrix shown in FIG. 3a. As will be discussed, instead of 3 columns, each with two vertically offset channels, the stimulation pattern may be defined for pairs of diagonally offset channels (i.e., a circuit is made from channels selected from different columns).

Accordingly, the field steering manager interface 78 provides the user independent adjustment of both the strength 76a,76b and the location 80a,80b of the stimulation field produced by summation of stimulation signals provided by the stimulation matrix 14. In the shown embodiment, the location of the field is adjusted along the left-right axis of the matrix 14 (i.e., perpendicular to the axis of the stimulated limb) using only two controls. Alternatively, the field location display of circles which light up corresponding to the left-right position of the field can also be selectively activated if a user slides a finger across the circles, or by double tapping a circle so that the stimulation field is adjusted to the field settings associate with the respective circle.

In embodiments, instead of 5 zones and the "All" setting, the user device 20 may be designed to provide a user with a coarser stimulation field control (e.g., only 3 zones may be selected and only the left, center, or right columns of stimulation is activated). Alternatively, a finer resolution of adjustments (e.g., 7-10 or up to about 15-20 zones) is defined using discrete steps with weight values for each column defined in a lookup table. When providing more stimulation zones than the number of stimulation columns available in the stimulation matrix, instead of simple On(1)/Off(0) status used in the above example, the columns are allocated weight values which represent "percentage of the total stimulation amplitude" (e.g., current) that results due to a weighting operation. The weighting values are used to adjust amplitude of each column. For example, the 'Left' setting can be realized as [100 0 0] and 'Center' can be [0 100 0], and a gradual shift from Left to Center can be realized using a series of montages with corresponding weights (e.g. [90 10 0], [80 20 0], etc.).

In embodiments users can toggle between a "coarse" field control (e.g., 5 zones) and a "fine" field control (e.g., 15-20 zones) as a matter of user preference. Alternatively, a user can simply select the number of zones from an allowed range (e.g., from 3 to 20). When a greater number of zones (e.g., 15) are used instead of fewer (e.g., 5), the change in the weighting values as the stimulation field moves from left, to center, to right, of the stimulation matrix is more gradual. For example, when using 7 zones then as the field moves from left to center, the weighting values of a circuit may change by 15% between each adjacent zone so that the left channel weighting transitions as 100, 85, 65, 50, 35, 20, and 5, while the weighting values for the center channels are inversely increasing, as 5, 20, 35, 50, 65, 85 and 100. However, while the transition may be smoother, increasing the number of zones can require a user to spend more time trying to discern differences between montages. Not to be limited by theory, during pilot work while some users preferred finer field steering control, this appeared to frustrate/confuse users who had difficulty distinguishing between the zones and who did not seem to benefit from finer control. The number of zones and differences between zones should be sufficient that a majority of users, or the user who is operating the neurostimulator, can feel movement of the location of the field (i.e., at or above their JND), without finding the number of adjustments to be tedious.

In embodiments, rather than using zero for any weight, the SaphLevel rules implemented by the system 10a require weights to always be set above a level such as 30%. Setting weights of non-primary channels to non-zero values can have advantages during treatment stimulation such as: a) providing stimulation at non-primary channels can cause the stimulation to feel richer, b) providing stimulation at non-primary channels can cause improved recruitment of the nerve due to increased energy of the vector field at the target nerve, c) supra or subthreshold stimulation at an area of the nerve provided by stimulation of the non-primary channels may increase the chance that stimulation from the primary channel will result in nerve modulation, d) the amplitude of the primary channel needed to recruit the nerve may be lower when energy from non-primary channels is also provided which may lead to increased patient comfort, and e) a higher amplitude at the primary channel may be used due to factors such as sensory masking. Additionally, the weights used at non-primary channels can change as a function of the amplitude that is provided at the primary channel. For example, the fall-off in weights can be larger when the amplitude of the primary channel stimulation signals is well above nerve recruitment threshold. In relation to SaphLocate, use of non-zero channel weights can also be useful when the stimulation signal location is adjusted, for example, from the left to the center-left channel. For example, increasing the weight of the center left channel from 0% to 50%, is larger than increasing the value from 40% to 60% and the transition can be perceived as smoother. Additionally, setting the weight at 40% rather than zero increases the chance that the stimulation is already above threshold, so that the increase to 60% is causes a smaller change in neural activity, and perceived intensity, than occurs when transitioning from 0% to 50%.

Individualized Adjustment of SaphLocate Parameters

In embodiments, the number of zones (and the associated number of stimulation montages and corresponding weight values) are selected due to the results of an assessment procedure that occurs during onboarding of the user. For example, an assessment of a user's sensitivity to finer changes is assessed by asking a user to press a button if they feel a change in the stimulation field location when the location is alternated between two settings, as may occur with a forced-choice threshold test where the threshold defines the difference between the two settings. For example, the system may automatically move the field using a coarse setting and then increase the number of zones and determine if the user is sufficiently sensitive to detect the movement between zones as confirmed by a button press. Once the JND of a user is established for distinguishing between locations, this can be used to set the SaphLocate zones parameters.

In embodiments, a SaphLocate feature adjusts the stimulation protocol so that a) the number of montages provided to a user and b) the corresponding weight values are both selected so the user can typically: a) perceive the movement of the field when selecting different montages and, b) movement of the field does not occur with large changes in the perceived intensity of the stimulation.

An advantage of the invention is to provide an adjustable level of tuning for the stimulation field controller which includes at least 2 levels of specificity or coarseness that may be selected by a user.

In an embodiment, the coarseness of zones may be set by selecting a "Settings Gear" control (see menu control of FIG. 9a). This will present the user with options that related to therapy including control of stimulation adjustments using a "fine" or "coarse" stimulation resolution. When clicked, a "Location Resolution" option display pushed is displaying the "Coarse" and "Fine" device control options (See FIG. 3e).

Figure 3F:
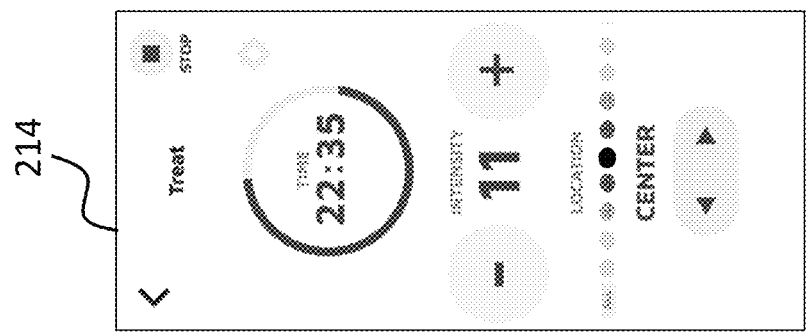
Figure 3E:
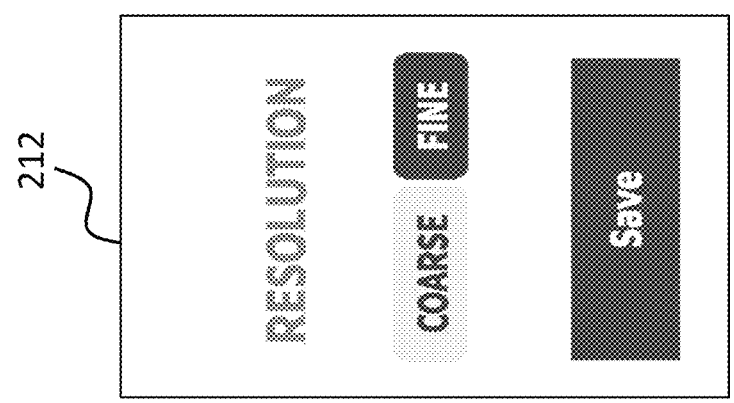
Figure 3D:
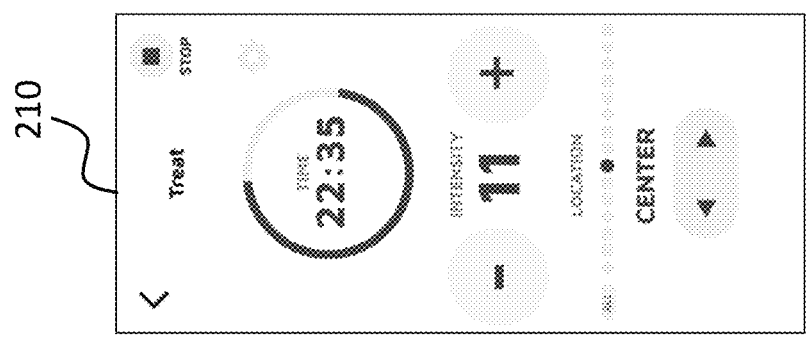
Figure 3C:
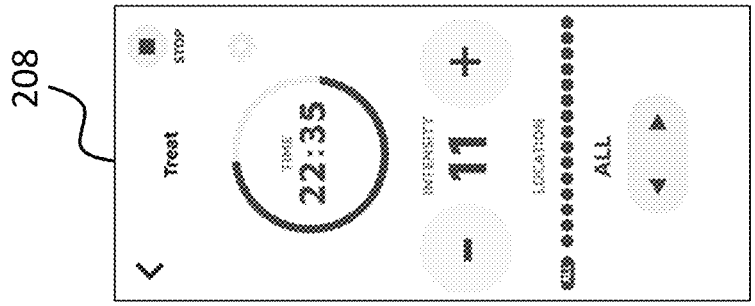

FIG. 3c shows a treatment screen 208 with the number of zones set to 15 using a Fine resolution scheme. This can be realized using 15 different weighting functions for 3 (or more) pairs of channels which are stored in a lookup table. In this example, when the field steering protocol is set to "ALL" then this includes 3 independent columns of constant current stimulation where all the channels of the matrix have equal weights. The "ALL" setting is an important option since during a study having stimulation montages limited to 3 vertical circuits (each comprising a pair of pads having a single anode and cathode), some users preferred stimulation using "All" (more than any of the 15 montages that moved the field from left to right of the matrix) since this provided better nerve recruitment than using montages where some channels had lower weightings, as evidenced by robust stimulation-induced paresthesia reported in their lower leg or foot with little or no muscle stimulation.

FIG. 3d shows a treatment screen 210 with the field steering protocol set to center, and again there are 15 zones. In an embodiment, "center" may cause the 2 pads of the center column of the stimulation matrix to have a weighting value of 100% while the adjacent pads of the Left and Right columns are weighted as zero (i.e., set as inactive).

FIG. 3e shows a Location Resolution screen 212 displayed by the device 20, having a menu for choosing a Coarse (e.g. 5-7 zones) or Fine adjustment (>7) resolution by a user. When used by a medical professional the resolution screen can allow for a more detailed control such as permitting the user to select any number of zones between 5 and 20 zones (and associated weightings) related to defining stimulation zones along at least one axis of the stimulation matrix. Additionally, when the stimulation field is adjustable along more than one axis, the resolution can be set differently for the x-axis (vertical) and y-axis (horizontal) of the stimulation field. If a graphical display or joystick is used by a user to move a stimulation field along the x-axis, or y-axis, or both simultaneously, then the coarseness can also be defined for such adjustment.

In embodiments, a "coarse" controller scheme utilizes between 3 and 9 steps between the extreme leftmost and rightmost field settings, with a preferred embodiment of about 5 and a "fine" controller scheme utilizes between 10 and 20 steps between the leftmost and rightmost stimulation field montages, with a preferred embodiment of about 15. These can be set differently for each axis.

FIG. 3f shows an alternative screen 214 embodiment, when more than 3 columns of electrodes are provided in the stimulation matrix. In this example, a user may select a "narrow" or "broad" spread for the stimulation, which causes, for example, 2-3 columns (e.g., [0 0 0 90 100 90 0 0 0]), or 7-9 columns (e.g. [0 0 80 90 100 90 80 0 0]) of stimulation pads of a 9-column matrix to be active. In this embodiment, the narrow or broad set of weighting factors for a set of pads moves from left to right. In the figure the weightings are displayed graphically so that the higher amplitude weights are shown with a darker circle, and the shading is lighter as the weighting decreases. The adjacent pads may be weighted using non-zero levels (e.g., columns directly adjacent to a primary set of channels are set at 50%) or a level of spread found to produce an advantage in the sensation experienced by a user.

Additional Stimulation Signal Characteristics

Without being limited by theory, in an embodiment, three aspects may serve as main determinants of the stimulation protocol that is selected for treatment of a target nerve such as the SAFN. The stimulation signal should: A) be at an intensity level that causes modulation of the nerve but which is still low enough to be comfortable/tolerable to a user during treatment; B) should be provided by a matrix of stimulation pads and stimulation montage configured to steer/shape the stimulation field so that it is focused on/near the target nerve for improved targeting of the nerve; C) have pulse characteristics that provide robust nerve modulation.

In addition to SaphLevel and SaphLocate aspects of the stimulation protocol, the stimulation signal itself can be modified by the program to improve nerve recruitment. For example, pulse duration may be adjusted to improve target nerve entrainment. While a pulse width of 200 uSec may often be used for a modulation rate in the 20 Hz range in the case of saphenous (or other) nerve stimulation, increasing the pulse width to between 400 uSec and 20,000 uSec, or using a duty cycle of up to approximately 50% may produce a deeper stimulation path and greater entrainment. The longer pulse width is also better at recruiting smaller diameter fibers including unmyelinated c-fibers. Accordingly, a control for adjusting pulse width may also be provided on the control screen or montages associated with deeper stimulation paths may be combined with longer pulse widths as a SaphLevel feature.

User Adjustment of Stimulation Field Location and Geometry.

In embodiments, a SaphLocate feature allows different stimulation montage settings to be assessed and compared to enable selection one or more montages which provided improved nerve recruitment to be selected and used by the treatment protocol. In the case of SAFN recruitment, a protocol that provides improved nerve recruitment may be defined, for example, as a protocol for which one of the following occurs: the strongest perception of nerve recruitment is obtained; an evoked paresthesia changes from being a gentle tingling to a stronger sensation (e.g., vibration or thumping sensation); an evoked paresthesia is felt at the most distal location (i.e., down into the foot and to the toes is more distal than evoking sensation only near the stimulation pads); robust nerve stimulation occurs in the absence of unwanted collateral co-stimulation, such as of adjacent muscle or other nerves; robust nerve stimulation occurs in the absence of foot movement; the difference stimulation energy required to evoke skin sensation (skin sensation threshold) and nerve recruitment (nerve recruitment threshold) is the smallest; or, the largest amount of nerve recruitment is reported by the individual in the absence of the feeling of pain or discomfort. While any of these criteria may be used, often the patient will simply be asked to choose a stimulation montage that produces a clear sensation of paresthesia which extends as far as possible towards the ankle and/or into the foot, while minimizing effects due to stimulation of non-target tissue. FIGS. 5a-5i show embodiments of screens provided by the user interface module 48 that permit adjustment of the stimulation field provided by a stimulation matrix 14 operating in conjunction with the stimulation module.

FIG. 5a shows an embodiment of a "Slider" field steering management console 216 in which the slider control is adjusted ("slid") from a leftmost position to a rightmost position. The user slides the bar control by swiping a touch display of user device 20 with a finger. The location of the bar is then set in a position during therapy that was most preferred by the user (e.g., produced the nerve recruitment). The movement of the virtual control on a display screen of a user device 20 is accompanied by visual signaling of changes in the position of the stimulation field. For example, one or more subsets of a set of colored circles may show the selected region of activation in relation to full range of the left-right axis of the matrix. Further the "c1", "c2", "c3" labels at the bottom of the screen can show the percentage of amplitude applied to each of three columns of the stimulation matrix (e.g., those shown by FIGS. 6a, 6b. and 6c). The bar control can also be realized as a physical control on the housing of the device 12 or of a user device 20 such as a remote-control device.

In an embodiment, as the control is slid from the left to the right position it travels through a series of intermediate positions and each position is mapped to a stimulation montage in a set of stimulation montages such that movement of the control corresponds to sequential selection of a series of stimulation montages. The set of stimulation montages is configured to cause a change in the location and/or shape of the stimulation field in an intended manner. For example, sliding the control can be mapped to cause the stimulation field to move along at least one axis of the stimulation matrix, such as from left to right, such that the movement of the field occurs without causing transient jumps in the perceived intensity of the stimulation field.

FIG. 5b shows a "Directional" field steering management console 218 with a set of controllers realized as left and right arrows which the user operates to directionally adjust the left-right displacement of the stimulation field. This control has several advantages. It is easier for users lacking fine motor control as may be needed to adjust the slider control. Users press the left or right control to incrementally shift the location of the stimulation field to the left or to the right. It has been found by the inventors that subjects tended to prefer a set of about 5 stimulation montages when spanning from left to right with the stimulation matrix design that was tested. Using an increased number of settings took longer for subjects to assess, did not as consistently provide perceptible changes in field location by users, increased the difficulty of selecting a preferred stimulation montage, etc. In an embodiment for stimulating the SAFN the directional control may preferably use between 5 and 10 montages, and more preferably 5. An "All" montage may also be provided.

In an embodiment, at least one directional control is provided which when pressed causes a defined movement of the stimulation field such as from the left to the right position. Typically, two directional controls are provided to allow user control in a first direction or a second direction that is opposite the first direction. Pressing a directional control causes the incremental selection of a stimulation montage from a set of stimulation montages such that operating the controls corresponds to sequential selection of a montage from a series of stimulation montages (with a montage characteristic such as an amplitude weighting value defined in a lookup table or realized through adjustment of settings in electronics). The set of stimulation montages is configured to cause a change in the location and/or shape of the stimulation field in an intended manner in response to user input to the control. For example, pressing the left and right directional control causes the stimulation field to move along in a first or second direction along at least one axis of the stimulation matrix, such as from left to right.

FIG. 5c shows another SaphLocate feature 220 of the system. In an embodiment of the "Cycle" field steering management screen, pressing the "P" button causes the stimulation module 42 sequentially adjust the stimulation field in steps through a set of stimulation montages that transition in a determined manner. For example, the transition is from a leftmost position to a rightmost position in relation to the stimulation matrix. The set of stimulation montages may include only vertically oriented circuits (i.e., columns of the stimulation matrix) or may also include one or two diagonal circuits). If a position is preferred, then a user can confirm this, such as by pressing the input button labeled "P", or the user can provide a verbal indication "use that setting" if the user interaction module 48 is configured to receive voice commands. The cycle may occur 2 or 3 times and the user may be required to select the same stimulation montage consistently for it to be selected for use in treatment. The system can then use the user preferred stimulation montage during the provision of treatment. In an embodiment, the sequential left-right adjustment, or other adjustment of field montages, is selected using sets of weightings for each stimulation channel as defined in a lookup table.

In the embodiment shown in FIG. 5c, the screen does not provide a visual indicator of field location comprising the highlighted circles (although the percentage amplitude being used at each of the three "columns" of the matrix is shown on the bottom of the screen). When this signaling was removed, subjects were not as confident in reporting where the field was located. Providing a real-time visual indication of the stimulation field characteristics in addition to the stimulation evoked sensation perceived at the skin can a) reinforce and facilitate subjective discrimination of field location and movement and b) allow users to become familiar with what location setting works best for them.

FIG. 5d shows a "select" device management screen 222 with a set of buttons provided to correspond to the left-right adjustment of a stimulation field. For example, 3 buttons can move the field from Left to Center to Right, and this position can be indicated visually by the 3 virtual oval indicators. The Select control only allowed a first subset of the pads of the stimulation matrix (e.g., 1 of the columns of the stimulation matrix) to be selected while restricting the stimulation to other subsets of pads on the matrix (e.g., the activated subset of pads was restricted to 1 of the columns of the matrix at a particular time). In an embodiment, a set of user controls are defined with each control associated with a particular stimulation montage and the controls are mutually exclusive such that only one control can activate a selected montage and associated set of stimulation pads.

FIG. 5e shows a "Toggle" device management screen 224 for which a user can toggle the stimulation field of each column of the stimulation matrix by selecting one of the controls to toggle each electrode pair of a column independently between at least ON and OFF states. Toggle can also be implemented to provide a series of steps between OFF and several amplitude weights (e.g., [off, 10%, 40%, 70%, 100%]). In embodiment, the "Toggle" control is programmed to be different than the "Select" control with the former only allowing one column to be selected at a given time and the latter defined to allow two or more columns of stimulation matrix to be adjusted. If toggle allows for multiple weights to be used, the brightness of the circles used on the display to indicate On/Off state, can also be shown as larger or brighter when the weighting factor is larger.

In an embodiment, a set of at least one toggle user control is defined so that the control adjusts the on/off state of a selected set of stimulation pads. In an alternative embodiment, the toggle user controls adjusts both the state (On/Off) and also the amplitude weighting of a selected set of stimulation pads. In an embodiment, the set of toggle user controls includes at least two user controls and the control adjusts the state (On/Off) or characteristic (e.g., amplitude weight) of at least a first and second set of stimulation pads, and toggling the at least two user controls is not restricted to be mutually exclusive.

FIG. 5f shows a "L-R Slider" device management screen 226 realized as three 3 slider controls, each of which controls a characteristic such as the amplitude if a set of stimulation pads such as a column of the stimulation matrix. These may be slid by a user to adjust the characteristic value to be set at a value within a defined range (e.g., between 0 to 100) to cause the stimulation field to be adjusted such as for the stimulation to occur on the left, center, or right region of the stimulation matrix. In embodiments, if the stimulation matrix has more than 3 stimulation columns defined for the stimulation matrix then use of sliders for each column becomes cumbersome. Additionally, this embodiment can be difficult since, like Toggle and Select screens a user can provide stimulation on the left and right matrix regions but not the center. This produces two discrete areas of stimulation and increases the complexity of selecting a field compared to the Directional screen.

"Toggle" was preferred by some users because it permits toggling the state of multiple columns to occur simultaneously, gave users more control than "Select", and provided a preferable sensory experience (ostensibly since multiple columns could be simultaneously activated). However, "Toggle" as discussed, introduced a user interface challenge due to multiple combinations of the 3 On/OFF buttons that was further increased when the buttons allow toggling between OFF a few intensity levels. Even using ON/OFF for 3 sets of channels could frustrate subjects. Select" forced the user to choose from only one column of the matrix (radio style). Users liked it because it was simple to implement, but did not provide the best sensation and may not have recruited the nerve as well. These considerations supported using the Directional user interface having ease-of-use associated with "Select" with the ability to use 5 stimulation montages that weighted more than one column and allowed adjustment of the stimulation field simply by pressing the two Directional controls.

In an embodiment, 5 zones define the steps for moving along the left-right axis of the matrix. The corresponding labels are (or indicate) Left, Center-left, Center, Center-right, and Right. An ALL setting is also provided where all 3 circuits are set equally, such as at 75%-80%, or at 100% (although 100% can result in an uncomfortable stimulation intensity that is too strong when transitioning from 1 or 2 circuits, since all 3 circuits provide energy). Alternatively, the center pad circuit is set at 100% and the pads of the left and right columns are set slightly lower (e.g., above 80%). Or only the left or right column has a lower weight value, for example, to avoid stimulation of muscle. If instead of Left and Right, the terms "Towards shin" and "Towards calf" are used in the software of the App 21, then this is switched depending upon which leg the user has indicated is being used to provide treatment.

When operating the system according to the above field-steering methods, the stimulus intensity can be initially set by a user in a location setting (e.g., Left) using intensity control buttons to select a strong stimulation level that is below a user's pain threshold. After SaphLocate has been used to assess the different field steering settings and select the stimulation montage that will be used during treatment, the user may then adjust the intensity setting to be higher or lower to provide comfortable stimulation levels during therapy.

Figures 5G, 5H, 5I, 5J:
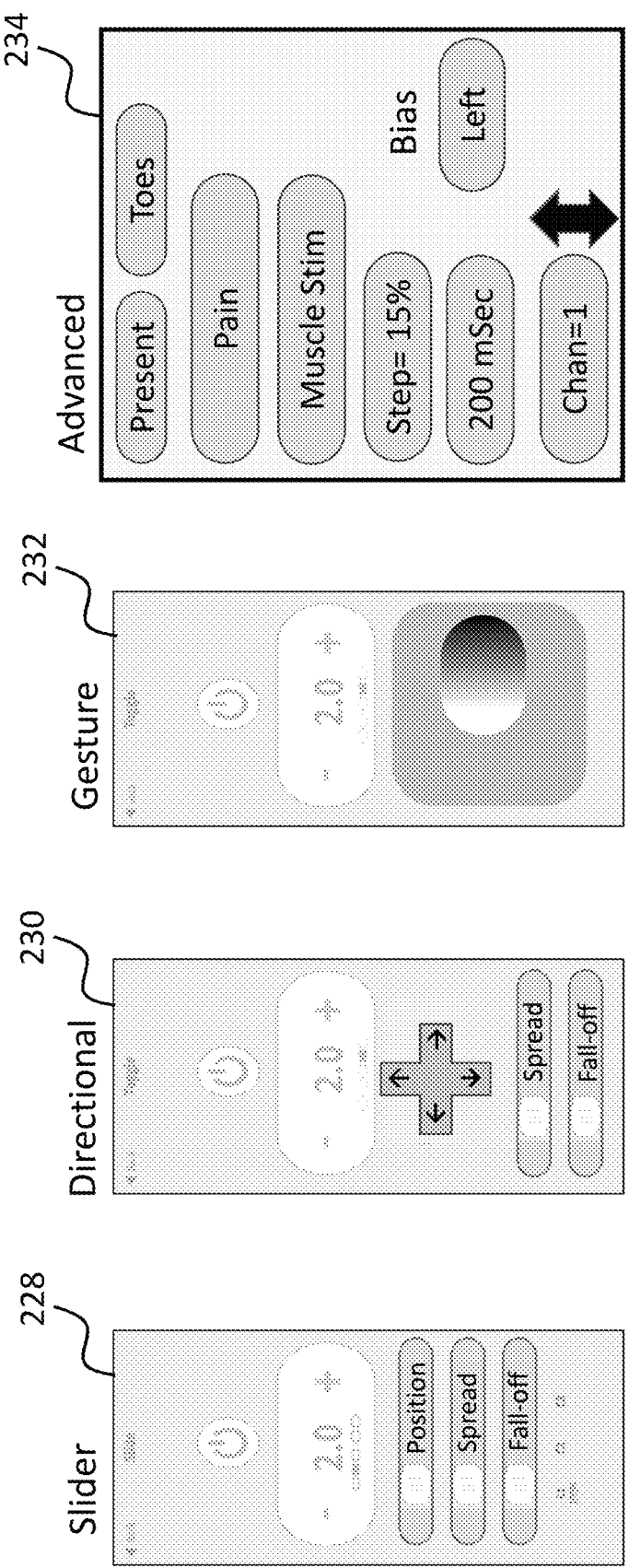

While the field steering controls just described provide advantages that are most evident when using a stimulation matrix having 3-5 columns, other controls may offer advantages when a greater number of stimulation pads are used in the matrix or if more complicated stimulation montage templates are used. FIG. 5g shows an alternative embodiment of a "Slider" management screen 228 having 3 different slider controls. The "Position" control adjusts the position of the amplitude maximum and may be set to control the field in the left-right axis of the stimulation pad, the "Spread" control adjusts the number of adjacent pads that are activated, and the "Fall-off" control adjusts how sharp the fall-off of weights are from the position of maximum amplitude. When used in combination with a stimulation matrix such as that shown in FIG. 7d, the Position control may adjust the column or columns (e.g., 4 and 5) where the stimulation circuit having the maximum stimulation occurs, the Spread control adjusts the number of adjacent columns which also provide active stimulation channels (e.g., 2-3 and 6-7), and Fall-off control increases the fall-off of the amplitude weights across channels as they become more distant from the maximum channels (e.g., 2 (85%) and 3 (60%)).

Figure 7E:
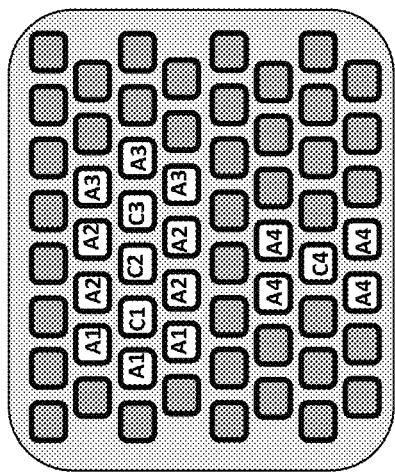
Figure 7C:
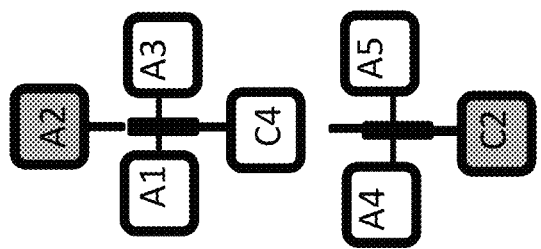
FIGS. 7a to 7c show stimulation matrix embodiments including sets of 4-sided stimulation pads.

FIG. 5h shows an alternative embodiment of a "Directional" device management screen 230 having a directional "joystick" controller, as well as Spread and Fall-off controls. As shown in FIG. 7e, a defined stimulation montage in the upper side of the matrix provides anode guarded stimulation using 3 cathode channels (C1, C2, C3) distributed across 3 stimulation pads surrounded by 10 anode channels. The joystick controller can adjust the location of the arrangement of active channels within the stimulation matrix. The Spread control adjusts the number of active channels in the left-right axis of the matrix (e.g., using 1 to 3 columns of cathodes), and the Fall-off control adjusts how discrete the stimulation field is by setting the fall-off of the magnitude of the weightings away from the primary stimulation channel(s). In an example, where the joystick set the primary channel near the center of the matrix (left-right axis) then "C2" and "A2" would have relatively higher weightings than the anodes and cathodes that flank it to the left and right as the Fall-Off parameter was decreased. In addition to pads that are directly adjacent to the cathodes, anodes may also be provided at non-adjacent pads that are separated from the cathodes by at least one intervening pad. In further embodiments, the user may be able to select several stimulation montages of various preset shapes and the joystick the permits these to be moved to different locations within the stimulation matrix. In the stimulation montage in the lower half of the matrix, the spread parameter has been decreased so that the stimulation field has less spread (along the left-right axis). In embodiments, the Spread and Fall-off controls can be provided to adjust the field along more than one axis.

FIG. 5i shows an alternative embodiment of a stimulation montage field controller screen 232 which includes a touch-pad controller that allows a user to adjust the characteristics of the stimulation field using gestures such as "dragging" a shape with a finger in a direction to adjust the location of the field within the stimulation matrix. Other gestures such as pinching the shape will decrease the spread of the stimulation field, or spreading two figures away from each other will widen the stimulation field. The gestures are tied to algorithms that make corresponding adjustments to the stimulation field by activating additional stimulation channels, deactivating stimulation channels, adjusting the weights of activated channels, moving the location of a set of active channels to a different position on the matrix, or selecting a montage from a defined series of montages that corresponds to the adjustment.

In embodiments, virtual stimulation maps provided by the virtual module 50a of the digital ecosystem module 50 permit users to control the stimulation module to spatially steer the stimulation field in 2D or 3D space. For example, users may adjust the location and shape of an image of the stimulation field which is presented on a grid or on a model of a leg. The user may "drag" the centroid of the field to a desired location and may "squeeze" or "push" the field away from a particular area. The device can adjust the stimulation in real-time according to the user's gestures, which are translated to corresponding stimulation parameters. For example, having a user drag the centroid of a stimulation field to the right on the display of a smartphone will lead to a corresponding shift of stimulation energy to the pads on the right side of the matrix. If a user squeezes a field or pushes a virtual button that corresponds to increased depth, then this may be accomplished using "guarding" or by activating electrodes with larger inter-electrode distances (which can increase field depth).

The SaphLocate features of the disclosed invention provide an advantage of allowing users to adjust the stimulation field characteristics in intuitive, user friendly manners that utilize pre-defined sets of stimulation montages, and series of stimulation montages, that may be selected or adjusted in a limited number of manners. This is preferred to requiring users to attempt to adjust stimulation parameters independently for each channel or for many possible stimulation circuits.

Lastly, FIG. 5j shows an "advanced" screen 234 that may be provided by the user interface module 48 to users with selected permissions, such as a doctor. It may only be provided on certain user devices such as a doctor computer 20c. In embodiments, controls are provided to enable users to select "paresthesia absent" or "paresthesia present" as well as where it occurred "toes" and these inputs are stored with the montage profile information in the log data. While the figure shows "paresthesia present", the button is a drop-down menu that includes other options, in this case "absent". Users can also indicate problems that occurs with a selected stimulation montage such as "muscle stimulation", "pain", "discomfort", or other side effects. The log information for a series of montages can be displayed in a table and information can be reviewed by a doctor to assess results. The screen also allows control of the step size of the changes applied to montages. For example, weight adjustment used to change a field location can be set (e.g., steps of 10% or 20%). The size of the changes in amplitude can also be set (e.g., amps). In embodiments, the montage may define stimulation signal pulse duration (e.g., 2000 uSec) of the primary channel to be different than (e.g., longer) than those provided at non-primary channels. That may increase the chance for the nerve under the primary channel to receive relatively more stimulation than occurs for sideband channels, and decrease risk for stimulation of adjacent muscle or nerve tissue. For interferometry, montages can be set different channels with different pulse rates or patterns. In embodiments, in addition to moving the location of the field, a button control with a drop-down menu is used to bias the field direction to the "left" or "right", at a minimum, but may also control biasing in a "proximal" or "distal" direction or to increase depth. The virtual field provided by the montage can be calculated by the virtual module 50a and displayed to a user. In embodiments, if a user deactivates a channel, such as to avoid muscle stimulation, then the stimulation module 42 will distribute the associated cathodic or anodic charge across the remaining active pads.

Automatic Adjustment of Stimulation Field Location and Geometry.

The system permits user selection of a stimulation montage to be used with selected stimulation matrix such as that shown in FIG. 3a. In embodiments, the system 10a also supports curated procedures for assisting with this selection. In an embodiment, a SaphLocate assessment protocol includes one or more of the following steps if a user selects a program button "P" as shown in the field control screen of FIG. 5c:

A) Ramp stimulation amplitude on two or more active channels. Obtain user input (e.g., button press) that flags at least of the following subjective measures for the user: skin sensation threshold, nerve recruitment threshold, level of strong but tolerable sensation, level of discomfort (e.g., a level believed to be unbearable for 10-30 minutes of stimulation), level of painful onset (e.g., a level that would be painful even for several seconds). At the end of the ramp, where strength of the stimulation signal is largest and where a user indicates it is painful, the stimulation intensity is reset to zero or the channel is turned off. Rather than, or in addition to, subjective measures, an objective measure such as SNAP can identify nerve recruitment threshold.

B) The ramp protocol is done for channel set #1 (e.g., C1 to A1, of FIG. 6a; active channels are unshaded) and then for each of the sets of channels defined for the remaining columns of the matrix moving from left to right or in random order (e.g., stimulation channel set #2 (C2 to A2 of FIG. 6b); and channel set #3 (e.g., C3-A3 of FIG. 6c).

C) The ramp protocol is done for each stimulation montage (and corresponding weights) for a set (e.g., 5) of candidate stimulation montages moving from left to right or in random order.

D) The ramp protocol is done for "All", which includes all columns of the matrix.

E) The ramp protocol is done for two diagonal stimulation montages such as C1-A3 of FIG. 6e or C3-A1.

F) This ramp protocol is done for each individual circuit (e.g., C2 to A1, then C2-A2, then C2-A3) of a stimulation montage which may be used during stimulation (e.g., the full montage is one cathode used in conjunction with 3 anode contacts (the combination of C2 to A1, and A2 and A3).

G) This ramp protocol is done for independent circuits of a stimulation montage (e.g., C1 to A2, and C2 to A3 of FIG. 6k) at the same time or sequentially.

Since all 6 of the stimulation pads of the matrix can operationally be set as an anode or cathode, the set of potential "channels" combinations that are assessed should be done in a limited manner due to the large number of possible permutations. The "programming" process should be done "intelligently" to provide a practical algorithm that only assesses permutations that are related to a limited set of selected stimulation montages. In a preferred embodiment, steps C and D occur and the stimulus montage that had the lowest nerve recruitment threshold is selected for treatment.

The results of this ramp assessment can be stored in a lookup table and displayed to a user (as a table or heat map for any of the sensation measures obtained in step "A") such as the patient or medical professional. In embodiments, the stimulation pad montage that produces the highest score for a desired characteristic can be selected. For example, the stimulation montage which corresponds to the lowest threshold of nerve recruitment, or the largest difference between nerve recruitment and level at which pain is experienced, can be selected by a user or by the SaphLevel algorithm. When various pairs of stimulation pads are activated as channels, such as a pair of 2 pads from a set of 6 or more pads, tables or heat maps may be used to present data to a user about which intensity levels were related to different sensation measures.

In an embodiment, a field adjustment algorithm uses channel weighting values that allow movement from the left-to-right or from right-to-left when a user presses the control buttons labeled "P" in FIG. 5c so that different stimulation of series a using activated selectively are zones be to configured be may This montages. perceived as moving from left to center to right regions of the stimulation matrix without sharp jumps in perception of cutaneous stimulation strength in the areas below the stimulation pads occurring with transitions between zones: i.e., similar perceived strength of stimulation is preferred. This enables the user to accurately assess and compare the different montages to select a preferred montage (e.g., strongest recruitment of the target nerve while minimizing unwanted effects of stimulation) to subsequently use during the provision of therapy. While weight values are adjusted to be non-zero in channels outside of the primary circuit (where stimulation amplitude is highest) during the assessment of different stimulation montages, these non-primary stimulation channels may then be set at zero when actual treatment stimulation is provided (i.e., if the central two stimulation pads (e.g., C2,C3 of FIG. 7e) are primary then the left and right circuits are zeroed). When a matrix such as that used in FIG. 7e is used, then the algorithm may move a pre-selected stimulation montage shape to different regions of the stimulation matrix.

Hardware Field Steering.

FIGS. 6a, 6b, and 6c show embodiments of stimulation montages realized as a left-sided, centered, and right-sided stimulation field, respectively. Each column of the stimulation matrix comprises one proximal anode (e.g., A1, A2, or A3) and one distal cathode (e.g., C1, C2, or C3). Alternatively, the top electrodes may be designated as cathodes and the lower set of electrodes serves as anode. A first circuit includes the leftmost pair of pads as shown in FIG. 6a (active=unshaded), while the central pair and rightmost pair are inactive. The user may also activate the central pair of pads as shown in FIG. 6b or the right most pair of pads as shown in FIG. 6c, while the other two pairs of channels are disconnected. This allows for movement of the field from left to center to right.

Instead of adjusting the amplitude weight values using a sequence that is defined for each of 3 columns of a matrix, the Slider control can provide stimulation using alternative sequence that moves the field from left to right by using a circuit defined with channels from two or more columns of the matrix. For example, the sequence which transitions from Left to Center can include the stimulation montages defined by FIGS. 6a, 6d, 6f, 6l, and then 6b. In other words, the stimulation montage sequence does not have to incrementally change from using 1 circuit (1 anode and 1 cathode) to 2 circuits (2 anodes and 2 cathodes), when adjusting the field from left to right. Additionally, while FIGS. 6a-6n show the anodes on top, the cathodes can be on the top of the pad.

With respect to generation of stimulation signals that contribute to shaping of the stimulation field, the stimulation module 42 may utilize circuit designs which use ganged arrangements of the stimulation channels, independent stimulation channels, or mixed arrangements.

Independent Channels. In embodiments, the system is typically configured to provide independently controlled stimulation signals to each stimulation pad. When using a triangular arrangement of 6 stimulation pads distributed across the top and bottom of the stimulation matrix 14, these can be realized as 6 independent channels of stimulation. This requires the stimulation module 42 to be capable of generating multiple stimulation channels as may be done using multiple stimulus generators, by multiplexing circuitry that can drive N channels through sufficiently quick switching, or by other means known to those skilled in the art.

Ganged embodiments. Ganged embodiments are realized when a signal from a single stimulation channel is provided through two or more stimulation pads (two or more stimulation pads are electrically combined).

In an embodiment, the stimulation module 42 is configured to provide or switch between independent stimulation channels or ganged channel arrangements, or a combination (e.g., a circuit of one anode and one cathode maybe provided, and then the user can activate another channel which is electrically connected to either the anode or cathode as configurable through electronic switch circuits).

While hundreds of embodiments are realizable by the system using permutations of independent, ganged, or mixed circuits, the following examples will be illustrated using 2, 4, or 6 independent stimulation channels. When stimulating a nerve that travels along a limb, using a limited number of defined channels provides easier adjustment of a preferred stimulation field by the user. Accordingly, the system may only use the channels defined in FIGS. 6a, 6b, and 6c (although the anode and cathodes may be switched so that cathodes are on the top of the matrix). Even if all 14 montages shown in FIGS. 6a-6n were included in a candidate set of montages, this is still preferred over independent control over each channel.

Because any combination of the 6 pads can serve as cathodes and anodes and further these can each utilize weighting values, a very large set of possible current steering settings are possible. To simply, in an embodiment, sets of predefined pairs of stimulation channels (e.g., C1-A1, C2-A2, C3-A3) serve as a candidate set of stimulation montages that may be assessed and/or used during treatment.

The following examples shows that the triangle pad arrangement allows for fields that move from left to right, are oriented vertically or horizontally or diagonally. While these are intended to be used with independent channels, ganging or mixed montages (having both independent and ganged channels) are possible variations.

In an embodiment, both the center and left columns of the matrix are "activated" to provide stimulation signals that constitute a center-left stimulation montage as shown in FIG. 6l, or the center and right stimulation pad pairs are used to provide a center-right stimulation montage as shown in FIG. 6m. Sequentially providing stimulation montages selected from a series of stimulation montages shown in FIGS. 6a, 6l, 6b,6m, and 6c allows users adjust the stimulation field location across 5 horizontally displaced zones defined from the leftmost to rightmost side of the stimulation matrix. The user can then select a zone from the group including: Left, Center-left, Center, Center-right, and Right.

FIGS. 6d and 6e show embodiments where the field crosses diagonally between the left and right side of the matrix. A narrower field may increase the chance that a nerve will be recruited, while using less electrodes than in embodiments such as in FIG. 6k. If the current supplied using 2 pads versus 4 pads is kept constant, then fewer channels will increase the current density since less area is used to provide stimulation when only 2 pads are used. FIGS. 6d and 6e can also provide increased current density (anodic) compared to that shown FIGS. 6f and 6g. A narrower diagonal field may also reduce risk of evoking collateral muscle activation. In an embodiment, as shown in FIG. 6f, C1 (cathode) and A1/A2 (both serving as anode) form a circuit that is slightly proximal on the leg to that of FIG. 6l.

In an embodiment, if a subject indicates good recruitment but also indicates calf muscle activation, then an additional set of stimulation montages may be provided that enables the user to adjust the field location in a new manner, such as allowing location adjustment to be more proximal and away from the calf. For example, if a subject prefers stimulation from the center column (e.g., C2-A2), but reports calf muscle activation, then instead of asking a user to move the entire stimulation matrix higher on the leg, the stimulation program can attempt to shift the field more proximal. For example, in an alternative embodiment which is not shown in the figures, the leftmost (C1) or rightmost (C3) electrode can serve as cathode and all the pads on the top half of the matrix (A1, A2, A3) serve as anode to form a circuit that allows stimulation to occur slightly proximal to that which occurs when C2 is used. This proximal shift in the location of the stimulation field on the leg may allow stimulation to be provided without stimulating muscle such as calf muscle. Alternative stimulation montages such as 6d, 6h or 6j can be attempted since these both involve stimulation of the center zone without involving the distally located stimulation pad of C2. Alternatively, both anode and cathode can be assigned to the top triangle as shown in FIG. 6n and further only the top of the triangle is activated. Accordingly, in an embodiment, in addition to montages which move the field along the left/right axis, there is a set of stimulation montages associated with a "shift up" or "shift down" option which will adjust a field to be more proximal or more distal compared to the current stimulation montage.

Further, the montage shown in FIGS. 6i and 6j allow the field adjustment downward and upward to that shown in FIG. 6h. Accordingly, while the field steering managers shown in FIGS. 5a to 5e illustrate controls for moving the left-right bias of the stimulation field, the stimulation matrix using 3-pad triangular sets of as disclosed herein also permits users to adjust the field proximally and distally along the axis of the limb when an Up/Down control is provided to allow users to toggle that parameter.

In the embodiment shown in FIG. 6e, channels C1 and A3 form a diagonal circuit that extends from the bottom left to the top right regions of the stimulation matrix. This stimulation montage may offer an advantage over a strictly vertical field (e.g., C1-A3) due to at least one of: a) shape/orientation of the field, especially in the cathodic region, may have a higher chance of intersecting a nerve travelling along the axis of a user's limb but is not directly under the cathode; and, b) the anode electrode may have a reduced hyperpolarizing effect on a different area of the modulated neve (to interfere with potentials travelling proximal or distal to the stimulation site). A diagonal montage may offer an advantage when attempting the record SNAPs above or below the stimulation electrodes.

In an embodiment, more than one stimulation montage may be selected during the provision of stimulation, or different channels of a stimulation montage may provide different stimulation signals. For example, an "effective" stimulation frequency such as 20 Hz is supplied by the combination of a first diagonal channel C1-A3 providing a 10 Hz pulse train signal, and a second diagonal channel C3-A1 providing a second 10 Hz pulse train signal. The two signals are offset by half a cycle and combine to produce a 20 Hz signal in the tissue that commonly receives stimulation from both channels. Without being limited by theory, one advantage of this stimulation protocol is that a nerve target is stimulated using two different stimulation vectors and one of these may be more optimally aligned to recruit the nerve. Also, lower current density at each electrode location may minimize cutaneous nerve stimulation. Additionally, both 10 and 20 Hz have been shown to produce strong therapeutic effects which stimulating the saphenous nerve in animal bladder-fill models (see Yoo and John, U.S. Pat. No. 9,610,442). Accordingly, even if only 1 channel is successful in recruiting the nerve, benefit should still be obtained.

In an embodiment, the stimulation protocol may select a stimulation montage from a set of 2 or more stimulation montages to be used at different moments in time. This may be useful in decreasing the risk of skin irritation compared to using a single circuit for the entire therapy session. Additionally, if a user indicates that they "like" 2 different stimulation montages, then switching between these during treatment stimulation may provide improvement if one of the montages provides better nerve modulation of the SAFN, although this is not perceived by the subject.

Turning now to FIGS. 6h to 6j, it should also be noted that the stimulation matrix permits not only vertical displacement (6h is more proximal), but FIG. 6h also creates a more vertically compact and broad stimulation field that may also be shallower than that provided by that shown in FIG. 6b. In embodiments, stimulation montages which have deeper field paths may be selected in response to a user who toggles a control for adjusting the stimulation field "deeper".

Lastly, FIG. 6n shows an embodiment where both the top set and bottom set of stimulation pads of the top half and bottom halves of the matrix 14 includes both anode and cathode assignments. A stimulation circuit can be defined and established solely within the top or bottom set of stimulation pads. While the resulting stimulation field may not extend as deep below the skin surface as occurs with larger inter-pad distance, it may be sufficient. This compact stimulation montage is more likely for target nerves in the arm or leg that are sufficiently shallow to the skin surface. Additionally, when stimulation signals are provided during a post-treatment stimulation interval, and designed to prevent skin bruising by increasing blood flow to the region under the pads, a more shallow stimulation field may offer advantages such as stimulation localized to the skin/pad interface area.

Rather than selected channels being active and others being deactivated, 3 pairs of pads (C1-A1,C2-A2, and C3-A3) can all be active and form 3 separate circuits, and the amplitude weights are set so that one of the 3 pairs of pads has higher amplitude ("primary") and the other channels have lower amplitudes ("non-primary"). Human testing was carried out on a small group of 13 subjects and results indicated that almost all subjects confirmed they could discern when the stimulation field transitioned between the 5 zones when these were provided using 5 sets of amplitude weights values for the 3 columns of the matrix. Accordingly, as will be disclosed, rather than being active or inactive, in embodiments of the SaphLocate feature, all channels are on, but the selected channels are set with higher amplitude weights to bias the stimulation field maximum in a selected location.

Multimodal Field Adjustment.

Graphically presenting information about the stimulation field can aid users to better distinguish between, or anticipate, different stimulation field geometries. For example, a highlighted circle on the right or center-right side of the display can cause a user to focus attention on the skin below the right side of the matrix as indicated by the display as shown in FIG. 3b. While useful for a small set of pads, such as 3 pairs of circuits that define 3 columns of a stimulation matrix (e.g., A1-C2, A2-C2, A3-C3), more detailed displays can assist when more complicated stimulation montages are defined as possible permutations such as those shown in FIGS. 6a-6n. In embodiments, the relative weights or stimulation signal intensities of signals output at each stimulation pad are visually represented using a heat map of the stimulation matrix and/or displaying numerical values at the location of each pad that correspond to the strength of stimulation. A color-coded map can be generated by the user interface module 48 to show users the intensity provided at individual pads, or the calculated field intensity of vector fields integrated across the modeled stimulation field calculated by the virtual module 50*a*.

The perception of both stimulation and changes in stimulation can be reinforced by operating the user interface module 48 to provide signals in the auditory and or visual modality with the user device 20*a* or the neurostimulator 12. The SaphLevel and SaphLocate software programs are configured to provide reinforcement signals such as: a) modulated sound and/or light stimuli (e.g., a light modulated a, and synchronized with, the same frequency as stimulation), b) auditory or visual cues timed to a change in the stimulation montage (e.g., as each of 5 settings are selected these are accompanied by tonal cues; c) visual stimuli provided on the housing or a screen of the user device that show the region of stimulation d) sensory cues with a volume or light intensity that are adjusted according to the amplitude/strength of the simulation signal.

Stimulation Montage Weighting Values.

In embodiments, a SaphLocate™ feature includes the use of appropriately selected stimulation channel weightings that permit adjustments in stimulation field geometry to occur which meet a criterion. This may be that changes in location are generally perceived or occur in a smooth manner permitting subjective assessment and comparison of two or more stimulation montages. When comparing different candidate stimulation field geometries, abrupt transitions of perceived intensity may be a problem since these can interfere with a user's assessment of important stimulation related characteristics such as judging presence of evoked paresthesia associated with nerve recruitment.

Characteristics that may be assessed by a user for determining a stimulation montage can include one or more subjective sensations, such as: subjective strength of the stimulation field; amount of unwanted muscle stimulation; comfort of skin sensation under the stimulation pads; quality of stimulation under the stimulation pads (e.g., prickly, pulsing, sharp/dull, etc.); presence/absence of nerve recruitment; strength of nerve recruitment; area of paresthesia; quality of stimulation induced paresthesia (e.g., vibration, tickling); overall comfort during stimulation; absence/presence of pain or discomfort; or other therapy characteristic.

In an embodiment, an object of the invention is to cause a field provided by a first stimulation protocol setting (e.g., using 2 channels) to be perceived as approximately similar in strength to a second setting (e.g., using 4 or more channels), while also allowing the user to perceive a change in stimulation geometry or location, and enable a user to determine which geometry or location is preferred. Even if the fields provided by a first stimulation or a second stimulation montage provide similar target nerve recruitment capabilities, a difference in perceived stimulation comfort or tolerability may determine the preferred montage for use during subsequently provided therapy.

Abrupt jumps (e.g., in perceived intensity) that occur when a user adjusts between different stimulation field settings hinder a user's ability to assess a change in a subjective measure due to a change in the location ("zone") of stimulation or a change in intensity. It is an object of the invention that a 2-channel stimulation field will not be perceived as much less (or more) strong than a 4-channel stimulation field simply because more stimulation pads provide the stimulation signal and evoke more activation of skin receptors or cause jumps in the vector field. Large perceived jumps can interfere with a user's ability to compare the difference of the two montages in recruiting the nerve.

An advantage of using weights to adjust signal characteristics (e.g., amplitude) allow the geometry of the stimulation field to be adjusted across different stimulation pad combinations without transient jumps in intensity, or other discontinuities, that would otherwise make it difficult for the user to compare (or even prevent accurate comparison) between alternative stimulation patterns. While weighting values may often be applied to amplitude, these may also be adjusted for other stimulation parameters such as pulse duration. The weighting values can also be applied to the duration of the stimulation pulses of a channel so that the perceived intensity does not cause large changes between different stimulation montages. When the pulse width doubles, the current density is the same but the charge delivered over time doubles, which may increase the strength or perception of the stimulation.

Another advantage is that when weighting values are used in the stimulation montages used during assessment of candidate montages, improved stimulation may be provided during the subsequent provision of therapy. For example, use of weighting factors in channels that are adjacent to the primary channels (i.e. the channels with the largest intensity) may also enable optimized stimulation patterns to be found, that might not otherwise be found, since supplying energy in adjacent channels may a) supplement the energy provided by the primary signal and provides stronger nerve recruitment, b) supplement the energy provided by the primary signal in order to cause nerve recruitment to occur whereas this would not have occurred if only using the primary channels for stimulation, c) enable recruitment to occur with energy in the primary channel at a lower amplitude (due to vector field summation or other manner of increasing the ability of a stimulation signal of the primary channels to modulate the nerve).

One SaphLocate feature that may be used to adjust stimulation channel weightings relates to a discovery by the inventors that when adjusting the geometry of the stimulation field (e.g., when transitioning from a leftmost to a rightmost stimulation configuration), the perceived strength of the stimulation (or other subjective sensations) could change by a large amount or "jump". Accordingly, SaphLocate uses a lookup table with channel weightings that decrease these perceived jumps between candidate stimulation settings to provide advantages such as enhancing a user's ability to select between different candidate field geometries.

The subjective discontinuity between two stimulation montages can occur when a first stimulation circuit (e.g., a left pair of stimulation pads (C1-A1) is used in combination with second pair of stimulation pads (C2-A2) that forms a second stimulation circuit. When additional stimulation channels are added, the perceived intensity of stimulation may "jump" if the stimulation protocol uses a weighting strategy designed to maintain an equivalent total current (integrated across all anodes or cathodes of the stimulation matrix). A problem here is that if the target nerve recruitment threshold is at 30 mA and the left circuit alone used 40 mA, and when the center circuit is added the channels are both set at 20 mA, then suddenly the subject may not feel any paresthesia. That is because the stimulation current at the nerve is below the target nerve recruitment threshold. Accordingly, the 4-channel embodiment should use a set of amplitude weight values for the channels that deters this type of unwanted result (e.g., use weighting strategies that maintains a stimulation current above a recruitment threshold).

In this example, adjusting the amplitudes of the 2 stimulation signals may compensate for the difference between the pad surface areas associated with 2 circuits, to match the total current provided at surface areas of the pads used by the 1 circuit of stimulation. Accordingly, the weighting value adjustment proportionately reduces channel weighting value by 50% when the surface areas of the stimulation pads doubled.

In the table below, 100% (i.e., weight coefficient of 1.0) indicates a stimulation signal (e.g., 20 mA) is provided without attenuation, while a value of 50% (i.e., coefficient of 0.5) indicates the stimulation signal current will be attenuated by 50% (e.g., 10 mA) for that stimulation circuit. The weights can also be defined for individual channels. In an embodiment, a set of weights is configured to maintain total current as shown in the table below having sample weighting factors used when transitioning from 2 channel to 4 channel stimulation montage. In contrast transitioning from a 100% weighting value for the left channels to 100% at both left and center will maintain current density over a larger area of tissue but will lead to a large increase in perceived stimulation strength. Both scenarios interfere with a user's comparison between the two stimulation montages.

The weighting values adjust intensity of the stimuli such that if a user increases the strength parameter value of the stimulation signal (e.g., from 30 mA to 70 mA, where a possible range is 0-100 mA) then this new strength value will be used to set the amplitude of the signal provided at each stimulus channel of a circuit after the strength value is multiplied by the channel's weighting coefficient, which in this example serves as a "gain adjustment factor".

| | | Location Setting | | | | |
|---|---|---|---|---|---|---|
| Channels | Left | Left-Center | Center | Right-Center | Right | All |
| Left | 100% | 50% | 0% | 0% | 0% | 33% |
| Center | 0% | 50% | 100% | 50% | 0% | 33% |
| Right | 0% | 0% | 0% | 50% | 100% | 33% |

In the above table, the amplitudes of the signals provided using 4 channels (e.g., when a user selects Left-Center or Right-Center) are each reduced to 50% (channel weighting=0.5) to maintain total current delivered by the stimulation matrix relative to the amplitude of the signals provided by any of the 2 channel montages (e.g., Left, Center, Right). Similarly, for 6 channels, each circuit provides an amplitude adjusted by a channel weight value of 33% (which is 33% of the amplitude provided when any one of the 3 circuits of channels are provided alone). Using 33% may be too low of a weighting value since, especially at lower amplitudes, this can cause the stimulation signal amplitude to drop below the sensation or recruitment threshold and/or because of non-linear slope of the perception—intensity curves. It does not permit comparison between the "All" setting with the other montages in the table. A weighting value of closer to 75% at each channel (and range of 50% to 85%) may be more viable.

In addition, when adjusting between stimulation geometries, instead of adjusting weighting values that correspond to amplitude gain, the average duration of the stimulation pulses may be adjusted to compensate for increasing or decreasing the number of stimulation pads that provide one or more stimulation signals. For example, when increasing from 2 to 4 stimulation channels a weighting factor can be applied to a stimulation signal characteristic such as pulse duration, which can be decreased to maintain a similar perceived signal strength. For example, the weighting factor can be adjusted proportionately or otherwise (e.g., a duty cycle of 40% can be decreased to 20%).

As noted, the inventors have found that a strategy of dividing the total current (e.g., by the number of channels or stimulation pads) does not, in fact, yield desired results of increased smoothness. While the table above retains the same total current/charge delivered when moving between stimulation pad configurations, it appears to have the disadvantage of causing large changes in perceived intensity between stimulation montages. This interferes with the ability of subjects to compare between candidate montages and select a preferred montage that provides successful modulation of the SAFN (e.g., strongest or most distal sensation of paresthesia while minimizing collateral stimulation).

In studies performed by the inventors, it was determined that the change in field size due to current being supplied by different numbers of stimulation pads (and changes in the integrated size and shape of stimulated surface area and possibly strength of a vector field), or a correction for that particular change that maintains total current, does not appear to be proportional to the changes in subjective strength of the stimulation signal. Maintaining a constant for total current delivered does not appear to correlate with a smooth perception of intensity between different combinations of channels. In an embodiment, this strategy is avoided when setting weighting coefficients. Instead, these are selected to cause the change in perception of stimulus intensity for different stimulation geometries to be less than a "geometry change threshold maximum value" previously found as acceptable in a sample of subjects.

Without being limited by theory, several factors may contribute to what is experienced by subjects when the field strength and/or geometry is adjusted. These may also explain why using weighting factors that are set to maintain the total current supplied by the matrix across stimulation montages that use different number of stimulation channels is not a successful strategy. One factor may be the issue of cutaneous sensation thresholds. For example, if a subject's cutaneous sensation threshold is 8 mA for a particular electrode set, and the amplitude of a first stimulation circuit is 10 mA, then the stimulation field is above the threshold. If a second set of electrodes are added to the stimulation montage and the weighting factors are adjusted to maintain the net total current (i.e., the signal is reduced to 5 mA per channel), then this will be below the sensation threshold and will not be cutaneously perceived by the subject. Rather weighting factors can be adjusted in relation to skin sensation threshold, target nerve recruitment thresholds, perceived intensity, sensed neural activity or other consideration.

In an embodiment, in contrast to the correction factors that maintain total current delivered across stimulation pads, two characteristics of stimulation weights are provided to decrease risk of jumps in subjective sensations when transitioning between stimulation montages: a) weights of adjacent channels to the primary stimulation channels are set to provide lower amplitude signals rather than being set to zero, and b) non-primary channels, which are also non-adjacent (i.e., may be separated from the primary stimulation circuit by at least one intervening stimulation pad) are set to provide reduced amplitude (e.g., current) stimulation rather than being set to zero. For example, in FIG. 6a the primary stimulation circuit is A1-C1 (i.e., left sided stimulation which provides the highest amplitude stimulation signals), and the non-primary stimulation channels are formed by adjacent anode-cathode pairs A2-C2 and A3-C3 of stimulation matrix 14.

In an embodiment, a Left stimulation field defines a primary stimulation circuit (weight=100%) that is complemented by a lower amount of non-primary stimulation provided by non-primary stimulation channels. For example, weightings are as shown for the A1-C1 (100%), A2-C2 (87.5%), and A3-C3 (75%) channels, respectively. In an alternative embodiment the 3 weightings used for the "Left" stimulation montage are 100%, 80%, and 67% which are revered for the "Right". Alternatively, the weight values may be selected as: 100%, 70%, and 35%; or, 100%, 50% and 20%. Accordingly, in embodiments, all 3 circuits are active in every montage, and movement of the field is caused by changes in weights which provides maximum stimulation in different locations.

| | Stimulation Montage Selected by User | | | | |
|---|---|---|---|---|---|
| Channel | Left | Left-Center | Center | Right-Center | Right |
| Left | 100.00% | 93.75% | 87.50% | 81.25% | 75.00% |
| Center | 87.50% | 93.75% | 100.00% | 93.75% | 87.50% |
| Right | 75.00% | 81.25% | 87.50% | 93.75% | 100.00% |

Another benefit of using non-zero weighting values at stimulation channels that are adjacent to the channels where the maximum stimulation field is provided is that instead of a non-primary stimulation channel going from zero to some value such as 94%, increasing from 50% or 85% to 70% is a smaller increase that allows for smoother transitions (and reduces the risk of the channel being below threshold prior to when it is increased).

In embodiments, if a user is surveyed and indicates that they do not feel distinct changes in the location of the stimulation field, or if the changes are not perceived as occurring smoothly then the weights are adjusted accordingly (e.g., to make the changes more distinct the weightings of different channels would be separated by a larger amount).

Rather than using a look-up table, the weightings for the different stimulation montages can be calculated using equations such as: Left circuit Amplitude=Amp*(BaseAmpW−(Location*SlideFalloff)(& Right Pad Amplitude=Amp*(BaseAmpW−((4-Location)*SlideFalloff)); where "Amp" is the amplitude of the current parameter limited according to a range of the D/A buffer (e.g., 0 to 80 mA); "BaseAmpW" is the weighting value percentage for amplitude in the primary channels (e.g. left=100%), "Location" is assigned a value based upon the montage selected by the user (e.g., 0, 1, 2, 3, 4), and "SlideFalloff" defines the slope value for attenuation at each non-primary channel (e.g., 6.25%). SlideFalloff can obviously be adjusted to be steeper or non-linear (e.g., raising it to an exponent of 1.2)

In an embodiment, a set of stimulation montages are realized as 11 left-right transverse zones with the weighting of the left circuit (C1-A1) set at each of the following values when the stimulation montage ("zone") was set by a user as the following:

When the "Far Left" montage is selected the amplitude of the left circuit of the matrix is attenuated the least and provides the maximum output according to the above equation. Alternatively, none of the weights may fall below a value such as 40% so that the left circuit stimulation remains on.

When a user assesses different montages to determine which may offer improved recruitment, then large changes in stimulation "strength" may interfere with comparing alternative candidate stimulation montages. However, the difference between adjacent montages must also be noticeable. In an embodiment, a set of weighting factors for a set of stimulation montages (e.g., 5, 7, 9, 11) is selected that both enables a user to distinguish between different montages (i.e., enable the transition between alternative stimulation paths to be subjectively perceived as movement of a field), while also being devoid of unwanted changes such as large changes in perceived stimulation intensity associated with changes in field geometry. Weighting values may also be used to avoid these subjective jumps in sensation for other change in stimulation montage such as anode-cathode designation, pulse width, etc.

In embodiments, adjusting the adjacent non-primary stimulation channels by multiplying the output current by weighting values in the range of, for example, 75-90%, rather than zero, (and non-adjacent non-primary channels in the range of 50-75%) enables the strength of adjacent stimulation montages to remain in an intensity range that cause subjects report changes in field geometry as "smooth transitions". This strategy has also been found to provide smooth transitions between montages when the stimulation matrix is applied to either the leg or the arm of users.

Factors Affecting Perceived Intensity.

Changes between perceived levels of stimulation strength may not change linearly with intensity. Excessive jumps of perceived strength (i.e., much higher than the just noticeable difference for change in intensity) may be due to non-linear strength/intensity recruitment properties of cells under individual stimulation channel. A selected stimulation intensity which exceeds certain thresholds can be experienced as medium, strong, or very strong. Another factor is vector stimulation from adjacent stimulation pads, which can cause the perceived intensity to be influenced by concurrent stimulation at the other pad. Regardless of the underlying cause(s) of abrupt changes user's perception of intensity, these unwanted transitions should preferably be avoided. In embodiments, features of the invention permit unwanted perceptual jumps due to these factors to be decreased. An aim is the provision of smoother perception of transitions between different field geometries to enable advantages such as, for example, allowing different stimulation montages to be more easily compared by a user.

SaphLevel Embodiments.

In addition to benefits obtained when comparing different stimulation field geometries, incorporating a weighted stimulation field during treatment stimulation can also provide advantages. In embodiments, SaphLevel uses montages of selected non-zero weights on selected non-primary channels to provide increased comfort, increased nerve recruitment, preferred stimulation sensation, etc.

| Far Left | Left | Mid Left | Center Left | Left of Center | Center | Right of Center | Center Right | Mid Right | Right | Far Right |
|---|---|---|---|---|---|---|---|---|---|---|
| 100% | 90% | 80% | 70% | 60% | 50% | 40% | 30% | 20% | 10% | 10% |

The inventors have found that some users prefer having at least one non-primary stimulation channel concurrently stimulate at a lower intensity that that provided by the primary stimulation circuit. For example, when a first stimulation circuit (e.g., C1-A1) provides stimulation the two non-primary stimulation circuits (e.g., C2-A2 and C3-A3), provide lower stimulation instead being inactive. As was disclosed earlier, an advantage was found in some subjects who reported the stimulation felt "richer", "deeper", or otherwise "more comfortable". Another advantage of providing lower weighted stimulation at adjacent stimulation pads is to cause nerve recruitment to occur with a lower maximum stimulation amplitude required at the primary circuit: accordingly, the stimulation signal of the primary channel is less likely to be near or above the pain threshold. Without being limited by theory, this advantage can occur due to vector summation of the stimulation fields at the location of the nerve or due to recruitment of a larger number of branches of a target nerve such as the SAFN.

In embodiments, the weighting values for the non-primary channels are set to change as the intensity of the signal of the primary stimulation channel (with weight of 100%) is increased. For example, while a "center" montage may use weights of 80%, 100%, 80% for a first intensity range, the weights change to 60%, 100%, 60% (typically for a higher range). This feature is achieved by setting channel weights based on a lookup table with row weights corresponding to defined intensity ranges and channels being defined in each column, or by a simple algorithm using a set of "if/then" rules.

In embodiments, after preferred stimulation field settings are selected using SaphLocate features, the SaphLevel features are used to provide treatment stimulation with a montage that is different than the montage selected by the user using SaphLocate features.

Although many SaphLevel settings will use non-primary channel stimulation, stimulation may be provided only from the primary stimulation channels (e.g., non-primary channel weights are set to zero). This can provide a more focused stimulation field and decreased risk of stimulation triggering unwanted muscle activation or spasm. Alternatively, the SaphLevel algorithm may only set the non-primary or non-adjacent channels to zero contingently. For example, the system operates the user interface module 48 to query a user about calf-muscle stimulation. If the user indicates muscle activation is present, SaphLevel will decrease the weight values of non-primary channels or at least of the channels closest to the calf muscle. In an embodiment, the SaphLevel algorithm uses information about whether the stimulation matrix is applied to the left or right leg (e.g., input by a user) to assign lower weighting values of non-primary stimulation channels that are located near the calf muscle compared to non-primary stimulation channels on the opposite side of the matrix. When the stimulation matrix is applied to the left leg the right side of the stimulation matrix is closer to the calf muscle, while on the right leg, the pads on the left side of the matrix are closer.

In an embodiment, a SaphLevel feature sets channel weights of non-primary channel pads adjacent to the primary stimulation channels to lower values than the primary-channels. This stimulation protocol may reduce some users reported discomfort or pain, and may enable a higher intensity level to be tolerated by a user. If a higher stimulation amplitude can be provided by the primary stimulation channels and tolerated by subjects (possibly due to phenomena such as sensory gating and lateral inhibition), then this increased stimulation signal strength may a) increase the modulation of the target nerve, b) increase the chance for successful target nerve modulation, c) increase the strength of the signal that is relayed centrally from one or more branches of the SAFN d) increase phase coherence of the average evoked neural response. Using an increased stimulation amplitude may increase the size of the evoked signal that is provided to the brain, providing a factor that can contribute to increased "electrical dose", and this may allow a decrease in total stimulation time, lower rate of users who do not achieve treatment success, or an increase in the corresponding therapy benefit or patient compliance.

Perception of the stimulation signal may be influenced by concurrent stimulation (with the same or different intensity levels) provided at multiple locations. Not to be limited by theory, increased perceptual "richness" from a larger stimulation field that is adjusted according to selected weighting coefficients may be caused by several factors including stimulation of additional nerve fibers, gate control, and lateral inhibition. These may influence a user's sensory perception including modulating pain sensation and paresthesia. Real world examples of these physiological phenomena include applying pressure, rubbing, or scratching an arm region near a region where a user is experiencing pain to reduce the sensation (e.g., itching a mosquito bite). Gate control and lateral inhibition models provides a basis for explaining how non-painful stimuli can provide sensory input that interferes with (and/or functionally reduces) painful sensations. Painful, nociceptive stimuli will stimulate primary afferent fibers which send signals to the brain via transmission cells. Increased transmission cellular activity corresponds to increased perceived pain. Conversely, decreased transmission cell activity reduces subjectively perceived pain. Gate control theory suggests a closed "gate" occurs when input to transmission cells, that relay signals to the brain, is blocked or "gated", this reduces the resulting sensation level of pain. This may provide a physiological basis for observed effects of pain perception, reconciles the specificity theories and pattern theories, and incorporates interactions between small (unmyelinated) and thick (myelinated) fibers.

In the gate control model, the non-nociceptive fast (myelinated) fibers can block the nociceptive slow (unmyelinated) fibers: "fast blocks slow". The theory asserts that activation of nerves which do not transmit pain signals, called non-nociceptive fibers, can interfere with signals from pain fibers, thereby inhibiting pain. It is proposed that when both small-diameter (pain-transmitting) and large-diameter (touch-, pressure-, and vibration-transmitting) afferent nerve fibers transmit information to the brain, less pain is felt (via reduced transmission cell activity in the spinal column) when neurotransmission activity in large-diameter fibers overrides the ascending transmission of signals from small-diameter (pain-transmitting) fibers. Accordingly, adding as little as 10% or even up to 100% of the stimulation provided on primary stimulation channels, using weights at non-primary channels, may influence the overall sensation of stimulation and may decrease pain that would otherwise be felt by a user for a selected stimulation amplitude.

In an embodiment, the primary stimulation channels (e.g., central pads c2-a2) serve to provide the largest source of modulation of a target nerve, while the stimulation provided at selected non-primary or adjacent stimulation pads supply an adjunct signal that: a) interferes with; b) distracts from; c) competes with; or, d) otherwise modifies the processing of sensory signals that result in the user perception of the treatment stimulation provided by the primary channels.

Additionally, the adjunct signal can enhance or otherwise change the perception of the primary stimulation signal.

In embodiments, an "adjunct signal" is designed to serve as a "sensory mask" that masks the sensations produced by the signals supplied by the primary stimulation channels. This specification has typically disclosed a signal provided at non-primary stimulation channels as the same signal that is provided as a stimulation signal, albeit at lower intensities. In an alternative embodiment, non-primary stimulation pads provide an adjunct signal that is different than the stimulation signal provided for the purpose of target nerve modulation. For example, the adjunct signal may have different frequency or waveform characteristics than the treatment stimulation signal. Adjunct signals may be designed to alter the user perception of the treatment stimulation signal. Mask signals may be a low intensity, high frequency, carrier signal or may be provided with pads arranged to primarily stimulate the superficial layers of the skin to simply produce competing sensory input. In embodiments, the sensory mask is provided by non-electrical modalities such as, vibration, sound, pressure, magnetic energy, or heat/cold. The sensory mask may be constant or modulated at a selected rate.

In an alternative embodiment, two or more signals are applied from channels of the stimulation matrix and are designed so that their combination (vector summation) at the target nerve produces the desired stimulation waveform while the sensory experience of the stimulation waveform is improved compared to that which would occur using the same stimulation waveform itself at all channels. In other words, adjusting the stimulation montage of the stimulation matrix by activating different arrangements of active channels, or the signals provided by those channels, to control field steering may incorporate principles and strategies related to stimulation signal summation (and may be intended to produce beat or other frequencies at a target).

Considerations and Advantages of Selected Stimulation Matrix Designs.

Figure 7B:
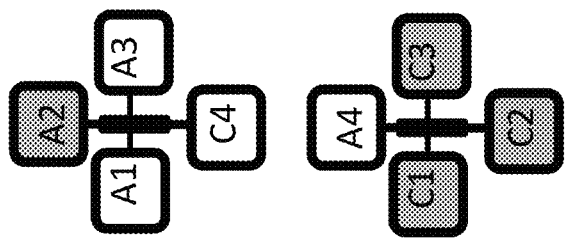
Figure 7A:
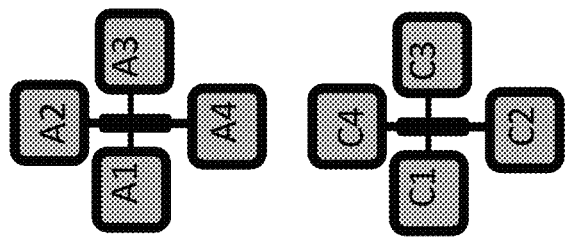

An alternative to a stimulation matrix with triangular pad arrangements is a four-pad "plus" arrangement shown in top half of FIG. 7A. A further embodiment uses two sets of 4 pad arrangement for a total of eight pads. The plus arrangements provide a benefit of long or short channel separations (e.g., C4-A4 and C2-A2) and larger range of vertically displaced/oriented fields, while using only 2 additional stimulation channels. A matrix with preferably 4 to 10, and more preferably 6 to 8, and most preferably 6 stimulation pads arranged in a fixed manner can allow robust stimulate of the SAFN.

SaphLocate Methods with Sensory Criteria.

Providing stimulation with a limited set of stimulation montages can greatly increase the ability of users to obtain robust stimulation of a target nerve. Only single-axis adjustment may be needed when the matrix is used to stimulate a nerve that travels along the limb of a user. Limiting the number of selectable stimulation montages to a set which includes 5-10 montages makes the adjustment of the stimulation protocol manageable. Defining a series of stimulation montages that adjust the location along a single axis such as the left-right access of the stimulation pad further simplifies selection of stimulation protocol by the user. Weighting of the channels of the matrix can allow different stimulation montages to be selected while meeting criteria such as sensory criteria which includes providing a series of adjustments that occur without perceptual jumps in stimulation intensity.

Figures 8A, 8C:
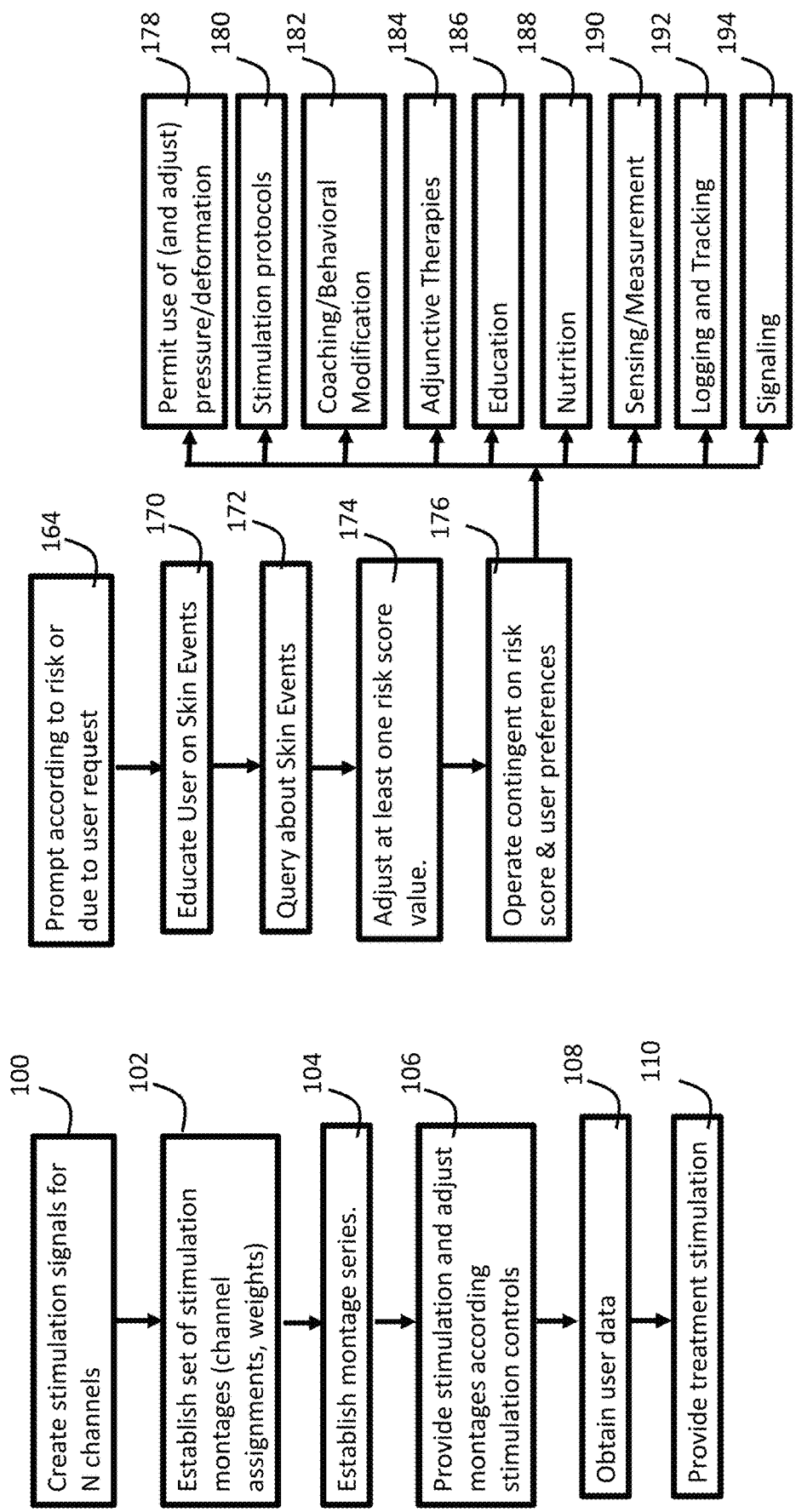
FIG. 8a shows a method for establishing treatment stimulation with a set of stimulation montages.
FIG. 8c shows a method for managing treatment to deter skin events and promote good skin health as may occur according to user preferences and risk scores of a user profile.

FIG. 8A shows a method for providing stimulation protocol assessment prior to, or during, stimulation treatment. In step 100 one or more stimulation signals for a set of N channels are created or selected. When stimulating the SAFN for treatment of OAB, a 20 Hz stimulation signal with biphasic square waves may be the default signal provided at all channels. Step 102 includes establishing a limited set of stimulation montages (i.e., channel assignments, weights, etc.) that can be selected or assessed by a user. The weights of the stimulation montages are adjusted to enable a sensory criterion to be met such as enabling the perceived intensity of stimulation to be approximately similar when the user adjusts the location of the stimulation field using the stimulation field adjustment controls. The set of stimulation montages are selected to provide an orderly transition for a characteristic of the stimulation field, such as changing the region of maximum stimulation amplitude along at least one axis of the stimulation matrix such as from the left side to the right side of the matrix, or from the bottom to top of the matrix. Step 104 includes establishing a montage series which includes a set of montages presented in a defined order. Step 106 includes providing stimulation and using the stimulation controls to obtain user input and responsively adjusting montages according to adjustment rules. For example, if a user selects the left or right control of a directional control then the montage is adjusted by incrementing or decrementing the montage according to a defined series that provides movement of the location of the field from the left to the right side of the stimulation matrix. The stimulation controls may also be defined to adjust characteristics of the stimulation field including the spread or fall-off of the stimulation field in pre-defined manners. In embodiments, a defined shape of the stimulation field is adjusted to move across a stimulation matrix in a left to right or up and down direction. In step 108 user data is obtained such as a user indicating preference for one or more stimulation montages or obtaining sensed data which is assessed to determine if nerve recruitment has occurred. In step 110 treatment stimulation is provided to a user based upon one or more stimulation montages selected by a user. In an embodiment, the stimulation montage selected by a user is used to provide treatment stimulation. Alternatively, the weights of a selected montage are adjusted (e.g., weights of non-primary channels are reduced) and then stimulation is provided to the user during therapy. If more than one stimulation montage has been selected by a user during the assessment procedure than the treatment stimulation may alternate between two or more stimulation montages during the provision of treatment according to parameters of the stimulation protocol (e.g., the treatment stimulation alternates in 5-minute intervals between two stimulation montages).

Guarded Stimulation Configurations.

In embodiments, the stimulation pads can be configured with an anode set to flank a cathode channel laterally, longitudinally, or both to surround and "guard" the cathodic field. This may allow a stronger signal to be used at a cathode while controlling spread of the field in a direction where an anode is placed. An example of anode guarding is shown in FIG. 7B, where cathode C4 is flanked by anodes A1, A3, A4 or FIG. 7c where a cathode is guarded by a set of anodes (A1, A3, A4, and A5). In this manner the longitudinal (along the vertical axis/length of stimulation pad) or transverse (along the horizontal axis/width of stimulation pad) stimulation can be "guarded" in an adjustable or selective manner to decrease risk of calf or other muscle activation. "Guarding" a cathode can also result in driving the current deeper into tissue. Guarding can improve recruitment of the target nerve by constraining the stimulation field, driving it further below the surface of the skin, and selectively avoiding unwanted stimulation of nearby tissue such as a calf muscle (e.g., soleus and gastrocnemius muscles), or biceps brachii, brachioradialis and coracobrachialis muscles when a target nerve is in the arm.

Field Steering: Shaping, Offsetting, and Depth Adjustment.

In embodiments, field steering controls of the system 10a provide for the adjusting of: geometry of the provided stimulation (e.g., the pattern of active channels); the location of a geometry (e.g., selecting different subsets of channels to change the location of a stimulation pattern in a proximal-distal, medial-lateral, or anteroposterior direction); the shape of the stimulation field below the skin surface; and, the depth of the field (e.g., using such features as anode-guarding, high-frequency carrier waveforms, longer duration pulses, or adjusting the distance between activated stimulation pads since further distances can provide a deeper field). In embodiments, the system's user interface module 48 allows a user to independently adjust field shaping with user controls related to adjusting stimulation field geometry, offset, depth, and guarding parameters. For example, user adjustment of a field characteristic is done by making pre-specified adjustments to a stimulation montage or selecting a series of stimulation montages which are organized to provide desired adjustment. When used for stimulation of the saphenous or posterior tibial nerve, adjusting the field's "depth" and driving the field deeper may provide improved nerve targeting while avoiding unwanted modulation of collateral tissue.

The App 21 has screens that provide virtual controls including duplicates of stimulation controls provided on the housing or display of the device 12, such as controls for amplitude and stimulation location (e.g., "+/−" virtual controls of FIG. 10c and FIG. 10d) or treatment (FIG. 9d). The app 21 may have additional screens with controls for adjusting the stimulation field as well (e.g., FIG. 5g).

In an embodiment, a first set of stimulation controls can modulate stimulation parameters related to geometry and location of the field to primarily allow for shaping and movement of the field across different areas of skin under the stimulation matrix. A second set of stimulation controls permits adjustment of field "depth" (e.g., using parameters related to anode guarding, pulse duration, carrier frequency, or selecting circuits with small or large inter-pad spacing). A graphical display may show the shape of a modelled stimulation field including a calculated location for the maximum amplitude of the stimulation field in relation to the remaining field. Visualization of the calculated depth of the field may rely upon numbers, color displays or 3D graphs. If a user modulates a "depth" control a graphical depth indicator or numerical display will reflect the adjustment to the stimulation field. This is accompanied by a change in the stimulation montage (e.g., stimulation pads located further apart are activated to provide a deeper path of stimulation such as using C2-A2 rather than C-A4 of FIG. 7B). Alternatively, the depth and geometry of the field may be represented on a 3D grid that can be rotated by the user, or by using both a shape display and a depth display, or by other display embodiments that allow a user to view and/or adjust (via touch screen) the shape, location, and modeled depth of the stimulation field relative to the skin surface.

In an embodiment, a user interface allows field steering using a representation of the stimulation field on a touch sensitive screen of a smartphone user device 20a. As shown in FIG. 5i, a graphical shape such as a dot, circle, or geometric shape is presented at location corresponding to a field maximum or a field's geometric center. The shape or maximum is adjusted by a user "dragging" an area of the image with a finger. The user provides a gesture to adjust the central point of the stimulation field (centroid) which can be superimposed on a display with a background image such as an anatomical representation of the leg or image of a stimulation matrix. The virtual field representation is superimposed on the image with a corresponding position and distribution. Further, a user gesture such as pinching the shape of the field shown on the screen (e.g., between a thumb and forefinger to "squeeze" the shape of the stimulation field), serves to narrow the field, or adjust its depth (e.g., using anode guarding), according to an adjustment algorithm that is programmed into the user interface module 48 and corresponds to the indicated adjustment. Alternatively, the user interface module 48 may present a display that includes a "shield" icon. Establishing or moving the shield on the screen will bias the field away from a shielded location to restrain a stimulation field from an unwanted area (e.g., by adjusting the corresponding anode guarding characteristic of the stimulation montage).

In an embodiment, field steering or other stimulation characteristic are determined based upon physical attributes of a user that may be obtained as part of patient onboarding due to surveying of a user (see step 108 of FIG. 8b) or medical data that may otherwise be available for a user. For example, characteristics of a stimulation regimen (locations, field steering parameter values, or waveforms) or ranges of parameters values, are adjusted based upon physical attributes such as body mass index (BMI), calf circumference, presence/absence of edema and measurements of edema severity, information from imaging data such as nerve location, subdermal fat/tissue characteristics, or measured tissue impedance. Physical attributes are input to a model or algorithm that selects or adjusts the stimulation regimen to improve nerve recruitment. For example, patients with edema or higher BMI may obtain greater nerve recruitment from a regimen that drives the field deeper into the tissue away from the skin surface (e.g., by anode guarding or stimulation waveforms that incorporate high frequency energy for improved transmission or other benefit).

The system 10a can use predictive analytics, AI, ranking algorithms, and machine learning to analyze and adjust treatment according to data of one or more subjects. These types of analysis can be used to predict treatment outcome based upon user data, to determine users who should see a urologist due to lack of symptom improvement, to determine users who can provide treatment at home independently, or who should be guided by remote medical assistance (i.e., increased level of interaction) to deter non-compliance or quitting. Changes in user data over time may serve as cues that require intervention. For example, it may be found that if a user rating of satisfaction with therapy is below a value (e.g., 7 on a 1-10 scale) that referring the user for a telemedicine session will decrease risk of them stopping the therapy.

The system may use artificial intelligence, machine learning, or other rule-based algorithm to correlate the success of various stimulation parameter settings to outcomes across a population of users. Based upon sensed data, measurements made by a user, or answers provided to survey times, the system may then recommend certain stimulation montages, or other system characteristics, that are more likely to work best for individual users. In an embodiment that serves as a simple example, the system may first query a user about presence/severity of edema, and also the type "pitting" or "non-pitting". If a patient indicates they have pitting edema, the system may suggest the use of a light pressure on the stimulation pads while for non-pitting edema high frequency energy or interferential-stimulation strategies may be suggested or used to increase the depth of transmission of energy through tissue.

Additionally, waveforms may be selected that provide sensations preferred by a user (e.g., a lower sensation of stimulation or pain at the stimulation sites). If a user has high sensitivity to cutaneous stimulation at stimulation sites, then a higher frequency energy, or other waveform characteristic, may be selected to improve user comfort. Alternatively, a matrix with larger stimulation pads may be selected to increase comfort and decrease current density within the cutaneous area near the pads. Additionally, if a user does not like the feel of the stimulation induced paresthesia, a different waveform may be used that decreases or changes the paresthesia sensation, or a mask stimulus is provided.

Impedance Measurement

A current-controlled system would typically mitigate most issues related to differences in impedance. Although current controlled stimulation compensates for impedance of individual channels, if the difference between channels is too large, or if one or more channels of the stimulation matrix has poor impedance then problems can arise including providing improper stimulation. Impedance monitoring may also play an important role when using ganged stimulation or constant voltage stimulation protocols. The EM module 46 monitors impedance sensed by the sensing module 44 and manages device operations if impedance measurements fail impedance criteria by operating according to "improper impedance" rules. Defined operations can include, for example, setting a flag in the control module 40 to cause it to pause stimulation and/or provide a user alert (by controlling the stimulation module 42 and/or user interface module 48).

In an embodiment, the EM module 46 is configured with impedance assessment circuitry and software routines configured to permit stimulation and/or field steering to occur correctly using the stimulation matrix. For constant current stimulation it may adjust the compliance voltage of the stimulation provided at higher impedance stimulation pads within tolerable range based upon changes of impedance that occur during therapy. However, if the difference in impedance for one or more pads relative to other pads exceeds a threshold value, then the actual stimulation field may deviate from the intended field and the device's stimulation circuitry will not be able to compensate. Even when using 2 stimulation pads it may be difficult to determine which one of the two pads is suffering from poor impedance. In embodiments, to detect an impedance problem, the EM module 46 is configured to test sets of stimulation pads according to a sequence defined in a lookup table. For example, for a set of three active pads, the circuitry can sequentially test defined pair combinations such as: pad 1 against pad 3; pad 2 against pad 3; and, pad 1 against pad 2. If the circuit created by pads 1 and 3 has acceptable impedance, then pad 2 is indicated to have a problem. Impedance may also be evaluated for pad combinations including more than 2 pads: pad 1 is assessed against a set of 2 or more pads which in this example are pads 2 and 3. When 6 stimulation pads are used then the average impedance of 5 pads can be compared to the impedance of a sixth pad using a criteria which sets a limit for the difference based upon value such as 1-10 kOhm, or based upon a percentage such as +150% (i.e., the difference between any tested channel of a set stimulation pads can exceed 1-10 kOhm or be over 150% of the impedance measured at other circuits). In an embodiment, when 6 pads are used then the tests can be based upon sequential combinations of 2 pads (e.g., 2 of the 3 pads of the upper or lower triangle or each of 3 defined vertical circuits for the left, center, and right circuits). In the assessment method, a circuit of at least 2 pads must fail an impedance test before an action (e.g., alerting a user, assessing and using an alternate "substitute" stimulation pad, etc.) occurs. Based on this assessment, if any impedance test conducted by the EM module 46 fails a defined impedance criterion, then the system will provide an operation defined in the EM module 46 such as: a) operating the user interface 48 module to provide an indication of the problem to a user, b) selecting and activating an alternative stimulation pad or c) setting the pad to an inactive state. For example, an alert such as a flashing light (or toggling a diode color from green to red), a vibration, or tone may be provided to a user by one or more transducers of the EM module 46 using the neurostimulator 12 or user device 20. Additionally, a text message or graphical depiction of the matrix on a user's leg is presented with color coded impedance values that indicate to a user the status of different pads 16 of the matrix 14. The text message (or push notification) can inform a user of high impedance for a region of the matrix (e.g., the upper right corner) or can instruct a user to "check pad contact on the top right of the matrix". Impedance assessment can occur at the start of a therapy session prior to provision of therapy, during the provision of therapy, and/or periodically (e.g., every 5 minutes). Impedance measurement can include pausing stimulation therapy short periods (e.g., 50-500 msec) or for up to several minutes during non-stimulation "rest" periods are defined as part of the stimulation protocol. Impedance measurement may also occur in a statistical manner that averages a number of measurements over a selected interval, or may require impedance measurements exceed a selected level for a minimum duration before it is assessed to be "unacceptable". If the impedance is not acceptable it may provide an auditory alert periodically, which can increase in volume over time, so that this is not ignored by the user. The control module may pause therapy if impedance measurements are not reduced after a selected number of alert signals (e.g., beeps) are presented to a user. Additionally, if impedance exceeds a selected level then stimulation can stop automatically.

In an embodiment, when a single cathode "C1" is used with three ganged anodes (A2, A3, and A4) then the system first determines if any channel suffers from improper impedance by sequentially testing the C1 against each anode prior to providing ganged stimulation.

Impedance matching may be useful with ganged embodiments. For example, a first ganged embodiment is realized by electrically combining the top 3 stimulator pads and, separately, the bottom 3 stimulator pads, such that all three top electrodes serve as Cathode and all three bottom serve as an anode to form a single stimulation circuit. The current will not flow equally between the 3 stimulator pads of each set, but rather will be a function of at least: a) skin and deeper tissue impedance along the pathway between electrodes; and, b) arrangement of pads/interelectrode spacing. The amount of current that passes between two stimulation pads can be modulated (i.e., decreased) by the stimulation subsystem circuitry which can introduce additional resistance between a particular stimulation pad and a channel of one or more of the stimulus generators (e.g., in a voltage-controlled system). Other methods of impedance matching for ganged stimulation designs may also be used.

In an embodiment, a voltage controlled ganged stimulation protocol such as a single pad in the bottom half of the matrix (e.g., C2) that is referenced to two stimulation pads in the upper half of the matrix (A1 and A3), may have unequal current flow to the upper pads. Impedance can be measured between the two circuits (e.g., (C2-A1 and C2-A3)) to compensate. In an embodiment, a set of resistors varying across a selected range are dynamically included in the circuit to enable approximately similar current flow along the two paths to increase the uniformity of the field bank.

In some voltage-controlled embodiments, the system senses impedance across circuits defined for different combination of stimulation pads. The impedance measurements are used to create a modeled field represented by the heat map display. For example, higher impedance may cause less current to flow between 2 or more of a set of stimulation pads and the current flow is modeled as stronger across adjacent channels having lower impedance. The modelled stimulation field can include model parameter values related to: signal amplitude, electrode shape, size, and arrangement (inter-pad distance, and orientation) of the pads in the matrix (i.e., "matrix pad geometry"). Modelling can also incorporate sensed impedance as measured between different pairs of stimulation pads to set values of tissue resistance or impedance of the skin-hydrogel interface.

Adjustment of Stimulation Signals and Montage Characteristics and User Surveying.

Various factors, such as pandemics, can make telemedicine preferable to in-person doctor visits. The system 10a is designed to allow set-up to be accomplished by a patient working independently or under the guidance of a medical professional. In both cases, the digital ecosystem module 50 manages user training about the stimulation 104 during onboarding. When a user adjusts and selects preferred stimulation field settings such as geometry, location, and intensity, the system obtains user input responses about stimulation evoked sensations.

In an embodiment, during training or therapy the system surveys a user to describe sensations associated with nerve recruitment by presenting choices such as: "Tingling, vibration, tickling, thumping, pinching, biting, other". Survey items may also relate to perceived intensity or comfort, with choices such as: "light, medium, strong, uncomfortable, painful, intolerable". Scale attributes can be combined such as "light tingling", "medium tingling", "strong tingling" etc. Further, the defined training protocol can contingently prompt a user 106 to increase stimulation intensity if user input indicates the sensation is insufficient, e.g., only a "light tingling". Training program may contingently 106 display a message for a user to use an alternate setting such as "A medium or strong tingling that radiates up or down your leg may work better, would you like to try increasing the intensity?" If the user approves a proposed option then the user is provided with a user display having controls that enable the option to occur i.e., adjustment of at least intensity. If the user rejects the option, the program may simply move to the next step of completing the training. If the system is designed to provide stimulation of a nerve target in a human arm, then software settings and labels are adjusted to be appropriate for the arm instead of a leg. For example, when surveying a user about paresthesia the survey item is anatomically appropriate: "extends to the tips of their fingers" is used rather than "to their toes". Similarly, surveying about paresthesia "moving towards the knee" is replaced with a "moving towards the shoulder" option.

The SaphLevel or SaphLocate features incorporated into training or therapy provision may survey about the location of the paresthesia associated with a selected intensity or stimulation field geometry. Choices may include, for example: "directly beneath the stimulation pads", "above the pads towards the knee", "below the pads toward the ankle", "down to the ankle", "into the foot", "all the way to the toes". Alternatively, a map of a body part such as a leg (or lower leg, from the knee to foot) is displayed and the user is instructed to tap the graphical display to indicate one or more regions related to paresthesia (e.g., the lowest point where paresthesia is felt). An "x" may then be plotted at the spot (See FIG. 9e) and the user asked to confirm. If a user indicates that the stimulation is only felt "directly beneath the pads" then the system can contingently prompt a user to further adjust an intensity or montage characteristic such as to produce a paresthesia that spread away from the location under the pads.

In embodiments, during training 104 the user is specifically queried about the presence of calf, or other muscle, stimulation. The surveying may ask about the presence of foot movement or cramping. If a user confirms this unwanted side-effect during onboarding or therapy a defined number of times, then the system may contingently operate 106 to schedule, or prompt a user to schedule, a virtual meeting with a medical professional. Alternative contingent operation 106 includes setting a flag value on this parameter in a log record or patient profile. Alternatively, the system may contingently operate 106 to instruct a user to select a different montage or present users with an "advanced" screen of controls (e.g., FIG. 5j) that guides, or otherwise allows users, to utilize a more detailed set of field steering controls that permits anode guarding or field shaping controls that assist a user to adjust a field shape, location, or orientation away from an unwanted location to avoid the unwanted side effect. In addition to permitting or guiding a user to decrease muscle stimulation using these adjustments, the system can also allow adjustment of the stimulation signal. For example, a default pulse train stimulation waveform is replaced with an alternative such as burst stimulation, or interferometry stimulation signals, or a high frequency carrier (e.g., 500 Hz-100 kHz) which is unmodulated or modulated by an envelope with a nominal frequency (e.g., 1-100 Hz) and pulse width (e.g., 10 us-1 msec).

Curated Neurostimulation Programs: Onboarding.

In embodiments, the onboarding process guides users through the first use of the system 10a. Shorter onboarding sequences can also be defined to occur at the beginning of each therapy session. The NiNA ecosystem provides a curated user onboarding process that includes features such as providing an overview of the therapy, training the users on providing stimulation, surveying users to develop a user profile and set user preferences, and providing educational content. Users are provided instructions on series of topics, are asked to perform operations and activities, and may be surveyed, with user responses logged. Onboarding may include instructing (or asking) a user about which leg they will use during the treatment session; instructing users to adjust a characteristic of stimulation, location, and intensity and survey the user about perceived sensations (for at least one intensity or montage selected from candidates); asking a user to indicate information using images; prompting a user to provide or confirm information by obtaining image data, such as taking a photograph of the device on their leg to track device placement, etc. This process can occur primarily using information presented visually with user interaction of a smartphone 20a or can incorporate interaction with a virtual assistant technology such as an Amazon Echo device 20e that provides instructions and obtains, processes, and stores a user's speech-based responses.

Onboarding operations may also be complemented by image data obtained using an image capture device (of a phone or webcam) which provides data to a software engine that can identify user behaviors through image analysis to automatically identify user activity such as determining the leg for which the wearable has been attached (and the position of the device on the leg), etc. The information obtained by visual and auditory interaction with one or more system devices can then be logged and uploaded to a remote computer 20*f* or to the user device App 21. Onboarding can use screens such as those shown in FIGS. 10*a*-10*k*.

FIG. 10*a* shows a screen 258 for providing features that educate a user and provide an overview of the therapy process.

FIG. 10*b* shows a screen 260 for providing features that train the user 104 on correctly securing the wrap to the leg and adjusting characteristics which may be related to location and pressure.

FIG. 10*c* shows a screen 262 for providing features related to training of the user 104 on how to adjust the stimulation intensity and FIG. 10*e* shows a screen for providing features related to training a user on how to adjust the location of the stimulation field. Either of these steps can include or be followed by surveying the user about the quality, intensity and location of sensations including paresthesia such as seen in screens 264 and 266 depicted in FIG. 10*d* and FIG. 10*e*. Users may be asked to provide a score or ranking of a characteristic related to nerve recruitment or an unwanted side-effect. Failure to obtain nerve recruitment, or presence of an unwanted side-effect, can result in contingent operations such as NiNA coaching the user to move the wrap location, change the pressure, repeat steps for adjusting intensity and location, or changing other stimulation characteristics until success stimulation is obtained. In embodiments, NiNA features are designed to educate, survey and train users about SAFN stimulation along a curated sequence that guides them on therapy-related operations including obtaining successful stimulation. As seen in FIG. 10*e* after adjusting stimulation, the user is asked to indicate one or more regions where stimulation evoked paresthesia is experienced by manually adjusting a "x" to the corresponding location on an image. A user can be surveyed to indicate the most proximal or distal location (or both) where paresthesia is sensed. This information can be ranked, organized, and displayed to assist NiNA and/or the user to determine settings for which successful nerve recruitment occurred.

In embodiments, the digital ecosystem module 50 includes software in its virtual module 50*a* that allows a user to select (e.g., draw upon) one or more regions of an anatomical representation of a user's body part such as a leg to indicate the location(s) corresponding to where the user feels stimulation-evoked sensations such as paresthesia. Additionally, the user may be surveyed on quality (e.g., vibration, tickle, pressure) of stimulation related sensations. It can also survey a user to determine if an unwanted side-effect has occurred. If a user indicates stimulation of an unwanted area or type (e.g., calf muscle stimulation) has occurred, using the anatomical map or otherwise, then defined contingent operations occur. For example, the control module 40 algorithm selects or suggests alternative stimulation settings that may provide improved comfort such as a set of one or more montages with a geometry that provides lower weighted or no stimulation near a non-target area (e.g., shin muscle or calf muscle), or providing notification to a user that muscle co-activation should be avoided.

Additionally, NiNA can provide a curated sequence of alternative stimulation protocols (and associated matrix settings that result in different patterns of stimulation pad activation) that are cycled through by the system. The program cycles through the candidates to determine which produced the largest or most distal region of paresthesia (e.g., tingling in their toes) and/or unwanted side-effects. A user may simply experience the different stimulation montages, or may be surveyed to indicate, through a button press or verbal input, which of a set of stimulation settings did not produce unwanted effects. Sensed information related to at least one of SNAP and EMG data may also be used to assessed to create a score or ranking that is then used to adjust the stimulation montage. The successful settings are stored and can be further evaluated by a user or selected during treatment. Additionally, protocols for which calf or other muscle activation occurred above a defined level can be rejected from further assessment.

In embodiments, the user can rank each stimulation montage according to amount of nerve recruitment and one or more side-effects. The montages with the highest ranks for nerve recruitment and/or lowest scores for side-effects are stored in a look-up table. Accordingly, if a set of protocols did not produce unwanted side-effects, and one of these produced the strongest rank for nerve recruitment, then this protocol would be suggested to a user or saved for further use during a therapy session. In addition to selecting locations where paresthesia is experienced, a user may be asked to provide qualitative, quantitative, or ranked feedback on sensation (e.g., tingling, thumping, tickling, vibrating, etc.). The data about sensory perception and side-effects input by users as part of a training or assessment procedure may be used by NiNA to select a set of stimulation protocol characteristics.

FIG. 10*g* shows a screen 270 for providing features related to setting treatment schedule preferences and FIG. 10*h* shows a screen 272 for setting of a time at which a reminder alert is provided (which can also be different on different days). Additional schedules can be shown to users and set for treatment events such as education, user surveying, remote sessions, etc.

FIG. 10*f* shows a screen 268 of NiNA features related to training, education, and coaching. Selecting items on the screen allows users to obtain on-demand education about nutrition and dietary choices that can improve symptoms (e.g., screen 274 of FIG. 10*i*), behavioral therapies such as Kegel exercises shown in screen 276 (FIG. 10*j*), and education about the disorder being treated and its symptoms depicted as screen 278 (FIG. 10*k*).

In embodiments, the onboarding process 100 relies on a set of user survey rules created using likelihoods determined from a sample of previous users, or based upon results in the medical literature, demographics, medical history, and logic. The survey rules defined in the survey module 50*f* cause user responses to a first set of one or more survey items to contingently lead to later items that have a greater chance of being relevant to a user. For example, in the treatment of OAB, if a user provides a response to a first survey item that indicates nocturia is a symptom, and the subject is >65, then a subsequent survey item may probe if they also suffer from restless leg syndrome (RLS). This survey item is more likely to be appropriate since risk of RLS increases with age and may contribute to frequency/risk of nocturia (or may be due more to RLS than to OAB). In another example, if a user indicates they do not suffer from stress incontinence the survey module 50*f* is modified so that questions about doing exercises focused on stress urinary incontinence (SUI), or about what activities are more likely to cause stress incontinence (e.g., laughing) are not subsequently presented to a user. In another example, if one or more survey items are answered as "not applicable" by many users who share certain characteristics or users who have also answered a prior set of one or more survey items in a particular manner, then that survey item may be omitted from questions presented to subsequent users of the system 10a.

In embodiments, during an onboarding process controlled by onboarding module 50e, users are surveyed 108 about therapy goals. For example, users may choose the most important therapy goal, rank their therapy goals, or be asked to rate the importance of goals such as: reduction in leaks, or pad/diaper use, reduction in number or severity of urges, reduction in nighttime or daytime frequency of voiding, reduction in bladder medication dosage needed for symptom relief, ability to delay longer before voiding occurs, or reduction in anxiety over symptoms. The responses are stored by the user profile module 50g, and the therapy program is then modified based upon these answers. For example, NiNA adjustments based upon the answers provided during onboarding can include educational content presented to a user from the reference materials module 50b, the survey items or user responses that are used to track a user's therapy progress, the scores used to assess user therapy progress 144 (which may also be used to adjust the treatment program such as to modify the duration of treatment or how often it occurs each week, etc.). Part of the progress tracking 144 includes updating and presenting timeline information as treatment continues and users complete (or fail to complete) treatment events and activities, according to log data information, and according to changes in symptoms.

Users who indicate they are awakened by the need to go to the bathroom at night (nocturia), may share some common behaviors or characteristics: a) Fail to decrease drinking near bedtime; b) keep a glass of water near their bed for drinking during the night; c) drink coffee, tea or soda at night; d) wake up after they already have wet the bed and did not feel any urges that awakened them; e) wake up and make it to the toilet without leaking; f) wake up and must urinate so badly they often leak before they arrive at the bathroom. Alternatively, some OAB suffers may typically sleep through the night and only experience symptoms during the day. In embodiments, the onboarding module 50e may survey users to indicate which of the above behaviors/characteristics are relevant and will then adjust therapy, surveys, or scheduled ecosystem events according to user responses.

Figure 8B:
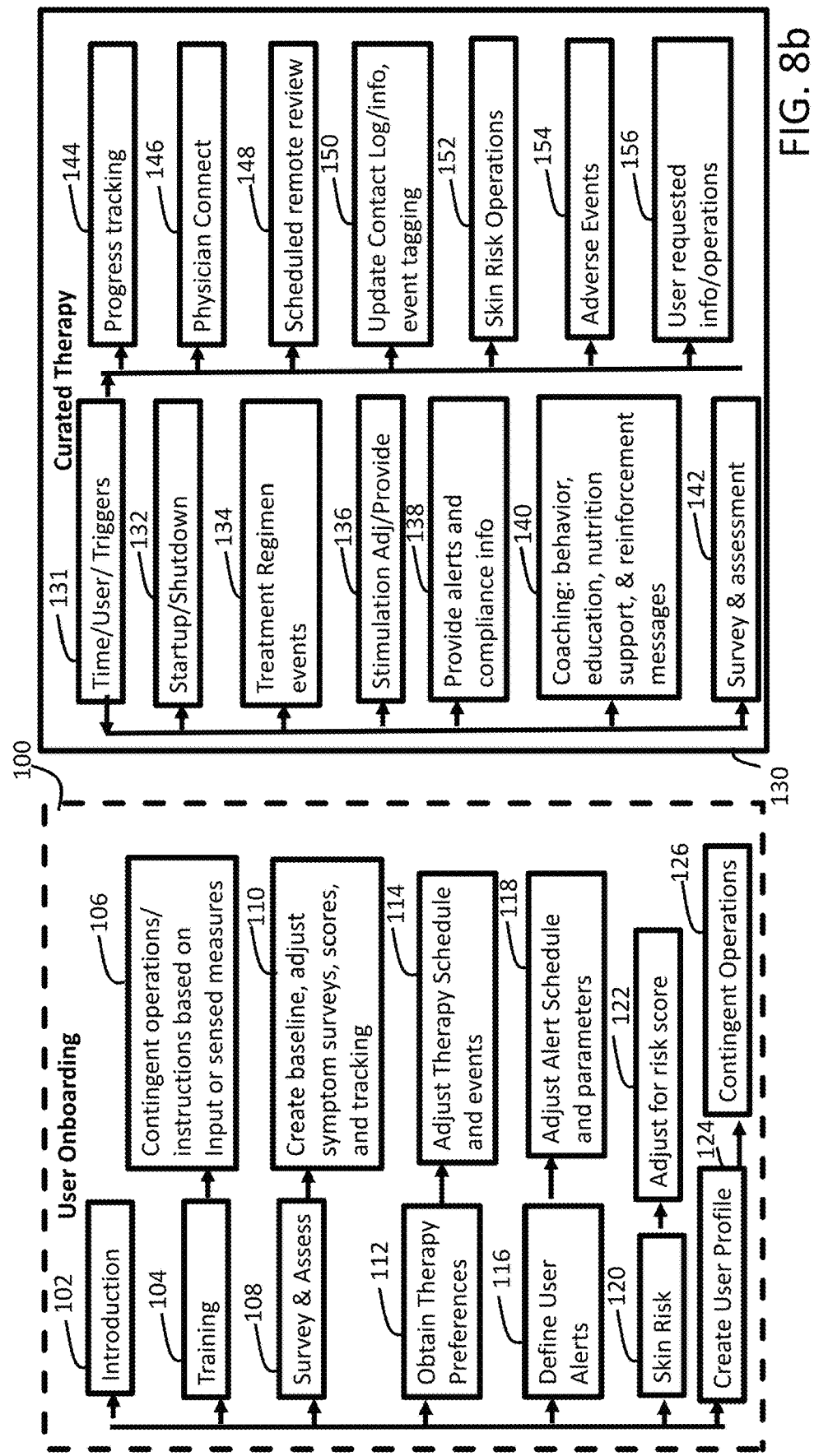
FIG. 8b shows a method of providing onboarding, induction and maintenance according to features defined for a curated treatment regimen.

For example, if users indicate nocturia is not a problem in step 100 of FIG. 8b then the system may no longer ask them any questions about symptoms related to that problem as part of step 104. If a user does not suffer from nocturia then as part of step 104 the system will also adjust the parameters of the coaching module 50h when surveying a user about this symptom or may modify the progress module 47 so that tracking or assessing treatment progress will not include nocturia symptoms when calculating any score used in assessment of progress. Alternatively, for users who provide a positive response for items a-e as part of step 100 the coaching module 50h of the digital ecosystem module 50 will be adjusted. In embodiments, the coaching module 50h will be adjusted so that the system will present videos, articles, statistics or "fun facts" about nocturia as part of step 104 and can set push reminders to occur at a selected time such as "try not to drink within 2 hours before going to sleep". It may also suggest to a user that providing treatment at night maybe preferable than providing treatment in the morning. The system 12 may also ask users additional questions related to frequency or severity of a symptom or behavior, (e.g., how many nights per week or times per night they are awakened by an urge to urinate). Educational content which is tailored to modify user specific behaviors and educate users on individual problems can serve to improve the overall therapy experience in addition to the benefits obtained by nerve stimulation.

In embodiments users are surveyed about stress incontinence in step 100. Users who indicate symptoms of stress incontinence symptoms may be surveyed further either as part of the onboarding process or in a later step that is provided during treatment. When only stress incontinence is identified during onboarding, then in step 104 a user may be informed that the treatment may not be appropriate for them since it is mainly intended for urge or mixed incontinence. As part of Step 104 they may then be asked to schedule an in-person or telemedicine visit to discuss this topic further with a medical professional. Alternatively, the system may be configured to survey the user with additional items that are designed to more accurately assess if a user suffers from mixed incontinence. In this latter case, a user can be informed that both stimulation and Kegel exercises or bladder drills should be included in the therapy program to properly treat their symptoms, and both prompts and education can be scheduled by the coaching module 50h as part of the therapy. Further, indication of mixed incontinence may cause a schedule in the coaching module 50h to be adjusted to provide more frequent remote sessions (or prompts to schedule sessions) with a nurse technician who will have access to the patient profile record where mixed incontinence is noted as a problem which should be treated and assessed during treatment.

In embodiments, during an onboarding procedure provided by the onboarding module 50e or provide later by the survey module 50f, the system 12 surveys users about how bothered they are by various symptoms. This can include scales related to, for example, how severely symptoms affect a user's lifestyle choices or interferes with how they would otherwise live their life. The user's responses related to bother may be compared to a user's scores for survey items about symptom severity. If scores for symptom severity do not correspond to scores for symptom bother, then the system may operate contingently. For example, it may survey users further about why a bother score is divergent from symptom severity. A user may be surveyed to determine if they are not bothered by a symptom due to: a) a belief the symptoms are part of normal aging, b) user habituation to long-term symptoms they have gotten used to, c) user adjustment/adaptation of daily living so symptom present less bother, etc. If symptom severity and bother scores are divergent, then the system can present selected educational material which may be adjusted based upon user responses to these survey items. The system 10a may also adjust progress tracking 114 performed by the progress module so that improvements in bother scores are tracked and presented to a patient instead of scores that are directly related to symptoms. In that manner a user can see progress as measured by improvements in how much a symptom bothers them, even if there are small changes in the symptom severity itself. Bother reduction can also be used as a treatment goal.

In an embodiment, survey responses are evaluated to indicate if a user has a profile which does or does not respond well to stimulation therapy. The system 10a can obtain and assess the user profile data either during onboarding 100 or as part of a website that users enter data into prior to starting therapy. Data for a population of prior users of the therapy is used to identify subpopulations of users who either benefit or tend not to benefit from the stimulation therapy, or who may need a longer induction period. For example, a user may be queried about prior or concurrent treatments (e.g., Botox, medications, other type of electrical therapy such as pelvic floor electrotherapy for stress incontinence, Kegels) and symptoms. Users can also be surveyed about previous or current OAB medication (e.g., oxybutynin, tolterodine, darifenacin, fesoterodine, solifenacin, solfenacin, trospium, mirabegron) as well as dosage. Surveying may also include other medications for conditions such as hypertension, anxiety, depression, headache, migraine, pain, etc. A user can also be surveyed about comorbidities such as diabetes, hyperglycemia, hypertension, metabolic, immunity, inflammation, or other disorders. The patient education and treatment can then be modified according to the user profile data. If certain drugs have been shown to increase risks of exacerbating OAB symptoms, then the user can be informed of this risk and provided with additional education. In embodiments, the system, stimulation protocols and NINA support are configured to provide treatment of any of the conditions and comorbidities disclosed herein rather than being designed to treat OAB. Further, in embodiments these are designed to treat addiction or substance abuse.

In an embodiment, if a user indicates they have been prescribed medication to treat OAB or another condition then the ecosystem surveys a user if they want the system to provide medication reminders as part of coaching 140 in addition to those provided for stimulation treatment. Medication reminders can also require user input upon taking the medication and the system can track compliance for both medication and treatment stimulation. When a drug or other treatment is provided in combination with SAFN stimulation, then this can be tracked, assessed for compliance and provided with reminders.

Onboarding and Therapy Methods.

The steps disclosed for FIGS. 8a, 8b, and 8c, and other methods, stages, and programs disclosed herein, can occur as isolated steps, be repeated, and can incorporate steps shown in other methods. As FIG. 8b illustrates, an embodiment of a curated treatment program that includes NiNA features provided by a digital ecosystem 50 which first onboards users 100 and then guides them during therapy 130 to provide a user friendly neurostimulation therapy experience and improved therapy benefit.

In embodiments, as part of step 100 a mobile software companion application "App" 21 is uploaded to a user device 20a. An Onboarding wizard of the App 21, which constitutes part of onboarding module 50e, provides a guided/structured sequence of operations that serves to onboard a user (e.g., FIGS. 10a-10k). Interactive displays allow a user to set up preferences used by the software programs that provide the therapy. Onboarding welcome operations introduce/explain 102 topics such as the medical disorder and provide an overview of the therapy and treatment timelines (e.g., FIG. 9b, 9c). This can include graphically presenting a user with a timeline of therapy events scheduled in the future including patient surveys, education events, at least one date for transition from induction to maintenance therapy. Onboarding 100 provides instructions and training on the neurostimulation treatment, proper device positioning, how to adjust and determine the correct amplitude and stimulation montage, and reviews additional features of the NiNA ecosystem.

In embodiments, the introduction process 102 includes steps such as: a) operating the app 21 to setup a user account with contact and billing information; b) communicate securely with the neurostimulator 12 to exchange data including ID data for the device 12 and matrix 14; and c) communicate all data related to the onboarding process to user account on a remote computer 20f.

In embodiments, onboarding provides an overview of the therapy 102 (e.g., FIGS. 10a,10b) includes patient accessing libraries of educational content on their disorder and symptoms (e.g., FIG. 10k), various features available as part of the therapy (e.g., FIG. 10d), how to provide treatment in an at home setting (e.g., FIG. 10c-f). Onboarding introduction 102 can include video content (e.g., device set-up and use, how to detect and rate stimulation evoked sensations or activity, how to adjust, assess, and select good stimulation parameters), access to weblinks, review of reference materials, and/or a remote telemedicine session. After instructional videos are shown in step 102, concepts are reinforced and users are trained 104 on aspects of therapy and are guided with step-by-step screens for attaching the device to their body and setting up the system for first time use. The instruction can also include diagrams, animation, instructions presented visually on topics such as how to adjust the stimulation parameters to produce nerve recruitment.

Training 104 can include screens that permit users to adjust the intensity (e.g., FIG. 10d) and location (e.g., FIG. 10f) of the stimulation using NiNALocate protocols and may include obtaining user feedback about stimulation evoked sensations (e.g., FIG. 10e). While muscle activity may be an unwanted side-effect for SAFN stimulation, for other nerves successful nerve recruitment involves evoked muscle activity (e.g., using PTN stimulation) or a decrease in tremor magnitude (e.g., when treatment is provided for a tremor or motor disorder), or other measure related to treatment of a different disorder. In these other treatments, users are be surveyed about both wanted stimulation-evoked changes and unwanted side-effects.

For SAFN stimulation, training step 104, can include instructions and training exercises on a) an overview showing a user providing stimulation; b) how to properly place the matrix on the leg (e.g., FIG. 10c) and adjust the stimulation strength (e.g., FIG. 10d) and location/geometry (e.g., FIG. 10f) of the stimulation field to target the SAFN and provide sufficient nerve recruitment; and, c) how to control the electrical stimulation to achieve a strong but comfortable paresthesia sensation from SAFN stimulation as well as asking the user to describe/confirm the paresthesia (e.g., FIG. 10e), and guiding the user until improved nerve recruitment is obtained. Controlling stimulation protocol parameters during training may also be used to avoid unwanted effects such as decreasing or avoiding: a) concurrent muscle stimulation (e.g., calf, leg, or foot muscle) due to unwanted spread of the electrical field; b) the sensation of pain from the skin under one or more stimulation pads due to non-SAFN cutaneous nerve recruitment; and, c) the need for using higher amplitudes to recruit the SAFN. The training step 104 may also include asking users about their perception of stimulation including: a) qualifying (e.g., tingling, pinching, etc.) the sensation of paresthesia; and, b) quantifying the strength of the sensations (e.g., light, strong, very strong, e.g., FIG. 10e; or rating strength on a scale from 1-10, with 10 being "barely tolerable", etc.) and providing information about location(s) or areas of skin stimulation or paresthesia.

In step 106, contingent operations are defined which occur based upon the feedback on the effects of stimulation.

For treatment using SAFN, if the user does not indicate they feel sufficient paresthesia (possibly indicating lack of nerve recruitment) or have an unwanted symptom then contingent operations are defined to guide a user to correct a problem so that improved therapy may be provided. For example, in step 106 a user is contingently provided 106 with further instructions, such as being asked to make an adjustment and repeat the process until they successfully stimulate the target nerve, changing parameters if they are experiencing unwanted muscle stimulation, switching to the other leg, changing placement on the same leg, or starting a remote session for guidance by a medical professional: however, training and feedback allowing correct device usage and setting of stimulation parameters should often be supported purely programmatically. During training, when evaluating or establishing characteristics of the stimulation protocol that relate to, for example, the stimulation amplitude or field steering the user may be contingently guided by their answers to survey items. For example, the device may survey the user by presenting the question on the screen "Do you feel any stimulation yet" and if the user response "no", then the device may contingently instruct the user: "please increase the intensity".

In step 108 users are surveyed about various topics including the absence/presence and characteristics (e.g., frequency, timing and severity) of symptoms. In embodiments, users are asked about their symptoms, to provide information about their therapy goals, medical and treatment history and other relevant information. In addition to being surveyed about their symptoms they may be asked to review educational information that is selected based upon their reported symptoms, medical history, etc. Further, all user responses are stored within and/or processed to adjust the user profile. The user profile data in turn can be used to adjust treatment parameters and events. For example, a user's therapy goals can be used to adjust educational information that is provided, measures that are tracked over time, survey items presented to assess symptoms or treatment benefits, progress that is tracked and goals that are achieved. If a primary treatment goal is to decrease pad usage then treatment characteristics, such as behavioral exercises, that are selected will be different than those selected if the goal is to decrease nocturia.

In embodiments, onboarding operations contain a logic tree structure and/or algorithms that utilize rules, artificial intelligence, machine learning with or without the use of neural networks, and other adaptive strategies to ask questions and adjust treatment to improve the user-friendly experience. For example, if a patient responds to a survey item 108 by indicating no prior prescription of OAB medication, then a survey list requesting the user indicate OAB meds used previously will be contingently skipped 110 according to a survey logic rule operated by the survey module 50f. As another example, if a user indicates during surveying 108 that the largest reason for seeking therapy is incontinence, then subsequent survey items on that topic are contingently selected 110 to be presented. The survey module of the system will also contingently 110 decrease or omit survey items that obtain user input about symptoms which the user reports as "not a problem" (e.g. a rule is defined to flag associated survey items so these are skipped during therapy). Additionally, if surveying 104 indicates that a symptom is not present, or a "bother score" is low for a particular symptom, then information about that symptom may not be tracked, displayed, used to assess changes in symptom severity, or goal assessment of a patient.

In an embodiment, users input data related to their medical condition using logic tree menus that enable easy logging of a medically relevant event which includes quantifying or qualifying at least 2 relevant characteristics. For example, for a leak event or bladder toileting event the system requires users to input a combination of two or more characteristics such as subjective urgency data and leaked amount. The leak event urgency may first be selected using a menu bar as low, medium, or high urgency. After a user moves their finger vertically to select one of the candidate choices, the user subsequently slides their finger to the right to select the second characteristic of the event. For example, this action invokes a further menu tree which comprises a second set of candidate choices related to the second characteristic, which in this example is an amount. The second set of candidate choices may include small, medium, and large amounts. In order to finalize the logging of the two characteristics of the event, the user can indicate the selection has been made through a gesture such as a screen "tap". This input method requires the user to characterize the event for at least two (or more) dimensions.

In step 110, survey response data is used to create baseline symptom scores. In embodiments, these data are used to contingently adjust which symptoms will be evaluated as therapy continues, when symptoms will be assessed, how these will be scored and tracked, how therapy progress is assessed, and how treatment success is defined. For example, if a user does not report any problem with nocturia then that measure may not be used to evaluate treatment progress.

In step 112, users can provide user preference information for therapy parameters such as therapy event and patient reminder schedules (e.g., FIGS. 11a/11b). Schedules are set for different therapy events including days, times and durations for providing treatment stimulation, user education, surveying about symptoms, and other treatment protocol events.

In step 114, these preferences are used to contingently adjust the therapy schedule parameter values so the system prompts the user at corresponding dates and times (e.g., days each week).

In step 116, the user is surveyed to define the characteristics of any alerts that will be provided according to user preference. Patient alerting includes using sounds, push notifications, calendar entries, e-mail, etc.

In step 118, user provided data and preferences for alerting are used to adjust the alerting protocol parameters which will be used by the system to provide the treatment regimen.

In step 120, the system surveys the user to obtain information related to skin sensitivity and to assess the presence of user characteristics that increase the risk for adverse reactions related to the skin "skin events" (e.g., tearing, bruising, skin irritation).

In step 122, the system then contingently adjusts operational parameters in relation to 1 or more user answers or by a composite skin risk score. The adjustments can include providing or instructing users about user behaviors, or adjusting the therapy protocols, which can decrease risks of therapy related skin events. Step 122 can lead to operations defined for step 176 of FIG. 8c.

In step 124, data obtained from user onboarding operations are used to create a patient profile and to contingently adjust 126 associated therapy regimen characteristics. This includes adjusting operation when providing various system features so these occur according to the information and preferences stored in the patient profile.

"Restore" Induction and "Maintain" Maintenance Programs.

The onboarding wizard provides the first steps in establishing a curated induction-treatment "Restore" program of the system 10a. Treatment provided by the system 10a can be guided, non-guided, or a combination. Even when treatment is guided using the Restore program, the user may also access reference materials or complete surveys in an unscheduled on-demand manner.

If a user indicates they will use the system 10a in a non-curated mode, or if a set of features of the Restore program are set as non-customizable, then during onboarding a user may skip (or is not presented with) adjusting parameter values for features such as days/times used to survey the patient. While typically users are guided through a prespecified onboarding process 100, this may include operations that occur contingently due to user input. Onboarding allows the creation of a patient profile 124 with user data and preferences that are used to adjust parameters of a curated treatment regimen with scheduled events such as treatments, patient education, symptom tracking, etc. The Restore induction program is followed by a "Maintain" therapy regimen of maintenance treatment. Events of the curated therapy regimens are triggered when a predefined date-time matches the datetime value of a real-time clock of the control module 40, due to user commands, due to commands received by a remote user device 20f, or other component of the system 10a.

Conventional clinic-based treatments using percutaneous posterior tibial nerve stimulation (PTNS) typically include a 12-week induction period of weekly stimulation. This is followed by a maintenance period with therapy sessions occurring about once per month. Prior to work done by the inventors, the interval required to provide sufficient induction with daily transcutaneous SAFN stimulation was not known. The Inventors performed clinical studies and results supports a 28-35 day period is a suitable induction interval for treatment of OAB with transcutaneous SAFN stimulation.

More specifically, in a study with >50 OAB patients (~50% refractory; ~50% drug naïve) a daily at-home SAFN stimulation session lasting 30 minutes showed that a OAB therapy benefit was improved if at least a 22 day interval was used, with most having an induction interval below 35 days. Not to be limited by theory, a meta-analysis of several clinical studies recently conducted by the inventors support a 28 day Restore program was sufficient for a majority (e.g., 70%) of patients. While some patients showed improved symptoms by 2 weeks, using an induction interval of 21 days or less was found to have long term disadvantages. For example, a shorter induction interval of 15-21 days compared to >21 days led to a lower rate treatment success and smaller symptom improvement at 90, 180, and 360-day timepoints. Defining the Restore induction treatment program to last between 22 and 35-42 days, and preferably 28-35 days is preferred. In embodiments, 28 days may be contingently extended such as to 35 or 42 days if a minimum defined improvement is not obtained by 28 days or if a patient chooses or allows a 42 day induction period. The extension in the induction period is accompanied by additional pre-defined scheduled events such as user surveying, coaching events, positive reinforcement messaging, and goal tracking.

An example of advantages for a 28 to ~35-day induction period compared to a shorter 15 to <21-day induction period is shown in FIG. 13 (objective OAB measures; subjective measures exceeding a clinically meaningful change). The table shows more consistent benefits at 180 and 360 days for the >21 day induction group. Not to be limited by theory, these data support, for the first time, that a SAFN daily induction interval can be reduced from 12 weeks used with clinic based PTN to ~28 days while providing good efficacy even 1 year later when followed by a maintenance regimen: even if symptom improvement for a user occurs quickly, induction periods <21 days appear to yield lower longer-term therapy benefit.

While these results were derived with daily SAFN stimulation, these are significant for minimum treatment protocols for other disorders when peripheral stimulation is used to promote neuroplastic changes. This may also be relevant for OAB treatment with other peripheral nerves of the leg such as PTNS. The proposed schedules for induction and maintenance are applicable to embodiments.

In embodiments, the induction protocol is preferably defined to occur daily for at least 30 minutes. The protocol may also use 5 or 6 days as a minimum to meet compliance criteria. The protocol can also permit or require more than one session per day (e.g., at morning and at night), or be realized as two shorter treatment sessions of 15 minutes each, or use longer therapy sessions (e.g., 1 hour). When providing more than 30 minutes of stimulation per day the Restore program may be reduced to a shorter interval than 28-days.

In embodiments, the Restore induction, can be contingently extended 136 at least once by 1 to 4 weeks if users have not met one or more minimum symptom benefit criteria after a given interval, or if they are otherwise willing to extend to increase therapy benefit. A longer induction interval can be set in the patient profile information established during onboarding or can be selected at the end of a defined induction interval.

The interval can contingently be adjusted to use a longer stimulation session (e.g., 60-90 minutes), and multiple daily stimulation sessions (e.g., morning, afternoon, and/or evening) during the original or extended treatment interval. At the end of any period defined for the Restore program, a user (who has not obtained a minimum treatment benefit or for other reason) may be asked to choose to, for example: a) increase the average therapy session length (e.g., from 30 to about 45, 60, or 90 minutes); b) increase the number of stimulation sessions per day (e.g., 1, 2 or 3); c) increase both the length and number of treatment sessions below a permitted limit; and/or d) increase the induction period to one of several permitted intervals. Alternatively, the induction protocol may be designed to contingently increase the treatment session length, number, or both based upon user data.

In an embodiment, during onboarding, a patient can choose an induction interval of 28, 35, or 42 days, a treatment interval of 30 or 60 minutes, provided across one or more sessions each day. Very enthusiastic users may select a 42-day interval with up to 60 minutes of stimulation each day. It is likely that longer than 60 minutes would not provide further benefit and could increase the risk of skin events. For most patients, using more than 42 days and 60 minutes of strong but comfortable stimulation appears to be sufficient to provide therapy benefit when stimulating the SAFN in the treatment of OAB.

During the maintenance period scheduled stimulation, or stimulation provided using an on-demand basis by the user, may be designed to occur only 1-3 days each week. In an embodiment, a module such as the onboarding or compliance module will restrict the scheduling or provision of maintenance stimulation, or will at least provide a warning message, according to at least one of several different types of sequential stimulation criteria, such as:
a) hour-based criteria can restrict the number treatment sessions that are allowed to be scheduled or provided within a selected time window such as 12 hours. This type of criteria may also be defined across different calendar days (e.g., a user cannot provide a treatment session at 11 p.m. on Tuesday and then 7 a.m. on Wednesday morning);
b) intraday criteria may restrict the amount of stimulation (e.g., 30 minutes) allowed to be scheduled or provided on a single calendar day;
c) interday criteria may restrict the amount of stimulation that is scheduled or provided on different calendar days.
d) intraweek criteria may require that the user selects or provides stimulation on non-sequential days that have at least one intervening day. Other criteria may require that if the user selects two days for scheduled stimulation that are adjacent (e.g., Monday and Tuesday) that the $3^{rd}$ scheduled treatment is non-adjacent and separated by at least 1-2 days (e.g., it is allowed on Friday); and,
e) interweek criteria requires that days on adjacent weeks must be distributed to meet an interweek criteria such as 3 days cannot be scheduled or occur within a 3-day period for two sequential weeks. For example, a user cannot schedule or provide stimulation on Mon, Sat, and Sun on a first week followed by Monday Tuesday and Wednesday on the following week.

These criteria deter users from providing treatment stimulation according to schedules that "clump" stimulation into clusters rather than distributing these more evenly in time. In an embodiment, if users provide stimulation that violates a sequential stimulation criterion, then the stimulation session is not counted toward meeting a minimum amount of stimulation for a given interval. A contingent operation may be triggered as if the therapy stimulation did not occur (e.g., patient reminders may still be provided contingently to meet a therapy compliance criteria). Additionally, the criteria can be defined to require a certain amount of stimulation occurs within a selected time interval.

In embodiments, the Restore treatment program is configured to provide a schedule of therapy events with a timing that is set according to the defined induction interval such as 28 days. For example, a symptom tracking protocol is used which first provides a baseline survey of a patient during onboarding. Alternatively, 1 or more baseline surveys are presented to the user before, during, or after defined therapy sessions (e.g., during or after the first 1 or 2 treatments of the first week of therapy). The Restore treatment program is then programmed to subsequently survey a user at later times such as at 2, 3 and/or 4 weeks to measure symptom severity. The progress module 47 assesses changes in symptoms by comparing the later survey results to the baseline survey results. Further, the Restore treatment program can report changes calculated by the progress module 47 for at least one of a user's baseline symptoms and symptoms evaluated at the later time (see FIG. 9*a*).

While these other events can occur at fixed times, these may also be adjustable and users can schedule the activities and events related to the therapy regimen. For example, survey items can be set to be presented on a certain day, or on a defined schedule such as every other day or week, etc.

The Restore treatment program of the App 21 can operate a progress module 47 to store one or more treatment goals defined by the system, or user-defined, such as reducing a symptom by a selected amount. At least one treatment goal may be selected by prompting a user to choose the symptom for which the patient most desires to see improvement (e.g., Nocturia), or choosing a goal for a symptom (e.g., reducing the number of nocturia events by 1 or 2). The progress module 47 can present encouragement messages (i.e., provide a positive outcome treatment results) to a patient when a goal meets 1 or more defined thresholds (e.g., "Congratulations your nighttime events have decreased by X %", where 'X %' is set to be at least of a set of defined percentages).

Coaching.

The coaching features of the NiNA digital health platform can be used to improve outcomes, increase user engagement, improve adherence, decrease drop-out or undertreatment, and save time, effort, and cost for medical practitioners. Coaching enables NiNA to guide and remind users so that appropriate user activity occurs. This disclosure has provided many examples of how the Restore and Maintain programs provide coaching such as user training on the therapy and scheduled events that are defined as part of therapy. In embodiments, NiNA provides therapy benefit independent of that derived by the stimulation therapy, or which supplements or supports the neurostimulation therapy. For example, behavioral coaching can provide alerts for scheduled toileting or messages timed to discourage drinking too soon before bed.

Coaching 140 can include providing reminders and nudges and providing information relevant to a patient's treatment, which is an important part of the user experience and can be especially convenient to present during a treatment session. These serve to support the user towards successful treatment and may include, for example, reinforcement via positive language and accolades, reminders for re-charging their device, and informational "snacks" to be digested before, during, or after treatment. There are also reminders provided by the coaching module that notify a user when it is time to resupply/replace their stimulation matrix pads ensuring clean/usable pads that provide effective treatment. Coaching can also cause a user or selected caregivers to be sent notifications about usage, symptom changes, non-compliance, etc. to encourage/monitor usage.

Coaching is provided as part of Restore and Maintain treatment programs to reinforce correct treatment. The treatment program of the system can include behavioral training and prompting as part of coaching 140 that includes use of individualized toileting schedules for scheduled or prompted toileting. In an embodiment, the system simply alerts an individual on a defined schedule to prompt toileting. The system may also alert a caregiver or nursing station as part of a scheduled toileting program. The prompts may also be tied to activities such as time going to bed, or typical time when a resident "wets the bed", so that the toileting occurs prior to a potential episode of incontinence. The toileting program can be related to preventing urinary or fecal incontinence or both. The program can also be tailored to be more frequent in cases where a user has comorbid conditions such as a urinary tract infection or ulcer related to moisture of the pelvic area.

In an embodiment, a data log is maintained that includes all therapy event types (stimulation sessions, scheduled survey questions, behavioral exercises such as Kegels etc.). The compliance characteristics for each event are defined and user activity is logged. For example, a stimulation session may require that a subject provides at least 30 minutes of stimulation using a minimum amplitude level), a survey session may require at least a minimum percentage of survey items were responded to by the user, a behavioral exercise may require the subject conduct the exercise for at least a minimum amount of time 5 minutes. The extent to which a user meets the minimum criteria of an activity determines if the activity is logged as compliant or not. In addition to defining event compliance characteristics, compliance evaluation rules are defined for each therapy event. For example, a compliance evaluation rule may require that 3 sequential stimulation sessions (or 3 stimulation sessions within a two-week period e.g., 3 out of 14) are missed before a non-compliance event is logged or flagged by the system, whereas for a different event the rule may be less lenient and even 1 event being missed triggers action.

When non-compliance occurs then coaching may include proposing a substitute event. For example, a substitute treatment event may be used to meet a compliance criterion when defined by one or more evaluation rules. For example, if a user misses two 30-minute treatment sessions, then the user may be prompted or allowed to meet a treatment event compliance criterion by providing 60 minutes of stimulation (instead of 30), if this is defined as an acceptable substitute treatment event. In an embodiment, the compliance evaluation rules may allow a selected number of substitute treatment events to occur within a defined interval, such as 1 month before a non-compliance action contingently occurs such as scheduling the user for an in-person telephone call with a medical professional.

In an embodiment, at least one of: a) the number of substitute events per defined interval, b) a compliance evaluation rule and/or c) a compliance notification rule is defined as a function of at least one of: the induction period, the maintenance period, whether a patient has shown a minimum improvement or decrement in symptoms, as defined by a doctor, or an alternative defined condition.

In addition to logging, calculating, and displaying trend data related to symptoms, which allows users to track progress, the data and summary statistics related to all therapy events can be displayed to a user to incentivize compliance and increase user engagement in their treatment.

In addition to user-scheduled events, information about a disorder or specific to a user's symptoms can be provided as part of coaching to periodically educate the user. For example, "pelvic floor fun facts" can be personalized for a user. For example, a user's summary statistics can be calculated from logged data including, for example, the average number of bladder voids per day or the average amount of time between bladder voids and this can be presented in the context of what may be seen for the disorder (or the range seen in other users of system).

In addition, to incentivize a user, the system may present messages about compliance or improvement in symptoms such as calculating the number of voids per day each week for a month and presenting a message to user about improvement if such improvement meets a defined threshold. For example, a message may be displayed if urinary urgency is rated lower for a recent 1-week window compared to the average urgency reported by the user for the first week of therapy or for a baseline period of 1 week prior to starting therapy.

In an embodiment, the Restore program presents a user with a set of 3-10 survey items once or twice per week to assess symptoms. Changes in a user's symptoms compared to their baseline symptoms that meet a treatment criterion can trigger positive outcome treatment events such as providing the user with a graph of progress and/or an encouraging message. Additionally, if changes from baseline fail to meet a treatment criterion, then negative outcome treatment events can be triggered such as: a) suggesting a remote meeting with a nurse practitioner, b) extending the Restore period for an additional period, or c) suggestion to a user that the treatment duration be increased to 1 hour a day for a selected interval (serving as booster treatments).

In embodiments, the Restore program can be used to provide, supplement, or substitute the therapy of an implantable device. For example, a wearable device is used to provide induction therapy for a period of >21 days prior to an implantable device being implanted which then provides maintenance therapy that occurs less often (e.g., 2-3 days per week). Alternatively, an implantable neurostimulator may be implanted and the patient allowed to heal before starting a period of induction therapy using a Restore program. Alternatively, after implantation a wearable neurostimulator or a combination of the external and implanted neurostimulators can be used by the Restore program. The schedule when the implantable device provides stimulation can be used to adjust the schedule of stimulation provided by the external device. For example, if the implantable device provides stimulation 2 days a week, the stimulation scheduled provided by the wearable can be adjusted so that stimulation is provided on the remaining days so that daily stimulation is provided during induction. The Restore program is adjusted to account for the stimulation schedule of the implanted device.

The Restore program provides coaching using a drip-feed of information at scheduled times. The drip feed algorithm is "smart" and will contingently show information on a symptom (e.g., nocturia) only if a user indicated presence of that symptom during user onboarding or if they have a symptom score for that symptom which indicates a problem and which exceeds a defined threshold.

In embodiments, the Restore program provides behavioral therapy exercises that have traditionally been delivered in-person by a pelvic floor physical therapist or nurse practitioner. This coaching aspect of system can undergo clinical trials to show independent or additional benefit to the neurostimulation without the ecosystem support and allows the software to be certified as a digital therapeutic, "software as a medical device", or a "software-based treatment" which may be separately prescribed before being activated as a feature.

Digital Ecosystem, Telemedicine, and Remote Management of Therapy.

In embodiments, a curated treatment program includes features provided by a digital ecosystem such as: a) computer assisted coaching 140 of behavioral and educational activities and training; b) computer assisted therapy (e.g. cognitive-behavioral) to assist with, for example, for re-training of unwanted emotional states such as anxiety related to a disorder by steps 148 or 140; c) scheduled or event based presentation of information that is relevant to a disorder or unwanted symptoms by step 140; d) access to a library of reference information by step 156; e) computer assisted patient surveying and symptom assessment by step 142; f) progress tracking by step 144; f) information about behavioral exercises including video routines for guiding the exercises by step 140; g) information on nutrition or supplements that may improve unwanted symptoms of a disorder by steps 140 or 146. The features can be provided according to user request 156 or due to a schedule 131 defined in the treatment program which are invoked as part of step 134 and use patient prompts 138 that remind a user to perform an activity. Reminders are presented to users 138 to improve treatment stimulation compliance according to a predefined, or user defined, treatment schedule or to promote other user operations, behaviors, or activities that can benefit treatment.

The ecosystem parameter values related to the provision of therapy can be approximately fixed, or may be initially adjusted according to patient profile preferences and then be further adjusted according to therapy failure or progress assessed at one or more timepoints.

Onboarding has already been disclosed and is used to create a patient profile which can be used to adjust selected subsequent treatment regimen characteristics according to patient data and preferences. As shown in FIG. 8b, a user's answers to survey questions provided at baseline in response to a user evaluation program as part of onboarding are obtained 100 and assessed (by software routines of the onboarding module 50e) to create a user profile 102 stored in the user profile module 50g. The system then contingently adjusts its operation 104 in relation to the user profile according to a set of user profile rules defined in the user profile module 50g. In embodiments, the user profile rules can cause adjustment of survey items presented by the survey module 50f, symptoms that are tracked and used to calculate treatment progress scores (by the progress module 47) so that these are adjusted based upon, for example: a) patient baseline characteristics of the patient profile (e.g., medical history, disease state/severity, symptom bother assessment, etc.), and/or b) user input about which treatment outcomes are most important, and c) the level of desired interaction with the system that has been indicated by a user. For example, the survey module 50f can present a user with survey items and request the user select whether reminders about stimulation therapy are desired or not. They system can then operate upon the user response data to adjust the frequency of patient education/coaching provided by the coaching module 50h.

Figure 9G:
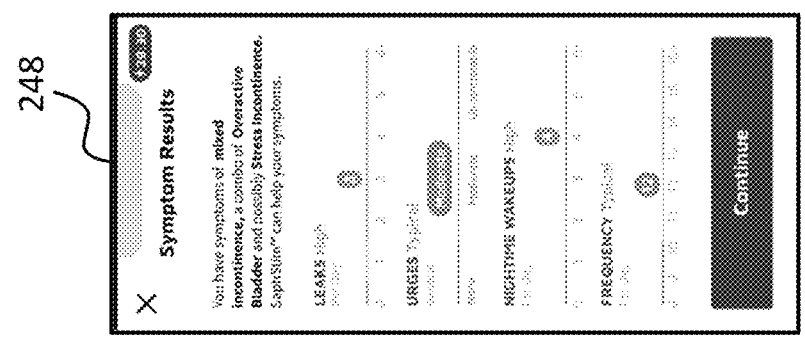
Figure 9H:
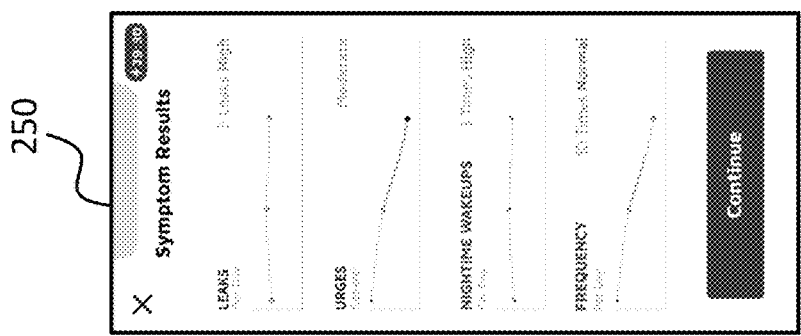
Figure 9I:
Figure 9J:
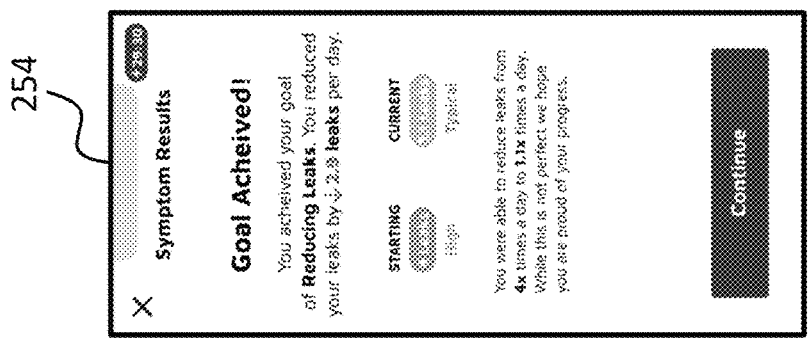
Figure 9K:

FIGS. 9a to 9k show examples displays selected and/or provided by the digital ecosystem module 50 of the system 12 during treatment. An embodiment of the Restore program uses the features provided by these top-level screens to provide curated therapy. Each screen represents a different feature category of the curated therapy. Some example features include the following screens: FIG. 9a showing screen 236 providing setting features that allows users to adjust settings of the program as permitted, FIG. 9b showing screen 238, provides an onboarding feature and provides educational content to a user, trains users on providing the therapy, screen 240 shown in FIG. 9c provides explanation of features of the treatment stages and schedules, the screen 242 shown in FIG. 9d provides control features, including field controls for intensity and matrix location, the screen 244 shown in FIG. 9e provides user input features including anatomical surveys which can confirm correct treatment, the screen 246 shown in FIG. 9f provides features related to monitoring and showing compliance, the screens 248 and 250 shown in FIGS. 9g and 9h provides features related to user input, display and tracking of symptoms, the screen 252 shown in FIG. 9i provides features related to tracking progress, the screen 254 depicted in FIG. 9j provides features of providing positive feedback and goal announcements as part of coaching; and the screen 256 shown in FIG. 9k provides features of informing users about advancing to a new stage of the treatment regimen.

The program can track user compliance in performing scheduled therapy sessions and can provide reminder prompts as part of coaching 140 users to perform a therapy session according to their selected preferences (e.g., reminders can be sent by e-mail, phone texts, and/or by push notifications, as well as provided by auditory or vibration alert signals). During the course of treatment, the program promotes compliance by providing alerts, monitoring, storing/tracking, assessing, and displaying compliance. For example, the program shows users scheduled therapy sessions vs. actual history of therapy sessions completed by the user (e.g., FIG. 9f).

FIG. 9a shows an embodiment of menu screen that is displayed by a user device 20a that allows a user to select different features of the ecosystem. The menu includes items which allow a user to view or interact with the following features: a user profile for letting a user create or "log into" an account which contains user data including user profile information; a) a home screen which provides tiles for accessing different areas of the ecosystem and having information about the treatment such as how many days a week they should stimulate and the current treatment number; b) a treatment screen that enables starting and controlling a treatment session; c) history screens which display information such as days where stimulation was provided or missed as well as treatment compliance information, statistics or scores, timelines or calendars showing days on which treatment was or will be provided or schedules of other events such as completion of user surveys, education, and scheduled days/times for remote sessions with medical professionals; d) a trends screen for showing trends in scores related to symptoms, bother, or goals; e) a "learn" screen that provides a starting point for accessing educational content including a digital library of facts and videos; f) a support screen that allows a user to contact technical or clinal support resources via remote technical/medical assistance, as well as video tutorials, user guides and instructions related to system use; g) a digital store having shopping cart functionality; and, h) a settings section for allowing users to view and adjust settings related to the therapy.

The system may also evaluate users for those with nutritional deficiencies due to improper caloric intake and nutrients and supplements can be suggested by the coaching module or ordered using the App 21, as also done for absorbent pads, replacement stimulation matrices, etc. These can also be provided on a scheduled basis as part of a monthly paid subscription of the NiNA service.

Although the menu of FIG. 9a allows a user to select different features of the ecosystem or provide treatment, in a preferred embodiment, the App 21 software typically guides a user through an onboarding and then provides a guided experience wherein the user interacts with selected portions of the program on a scheduled basis according to a predefined treatment regimen. In an alternative embodiment, the predefined treatment regimen (including a treatment schedule) is adjusted based upon at least one of: user preferences, changes in symptom severity, and user compliance.

One selection of the menu is "Treat" which can take a user to the treatment screen shown in FIG. 9d. Instead of setting the stimulation parameters using the controls, the user can select an option "user prior settings". In embodiments, the control module 40 of the device 12 (or user device 20) permits users to store therapy settings (e.g., stimulation or user notification parameters) according to user preference. Settings and parameter values may be hard-coded or selected and adjusted by the user. Additionally, the system may reuse settings previously selected for stimulation treatment by a user including parameter values for stimulation signal characteristics (e.g., intensity, pulse width, and frequency range), and stimulation montage settings (e.g., defined weight values for combinations of active channels that are defined as anodes and cathodes). For example, if a user opts to use previously stored parameter values of a therapy protocol then when a treatment session starts the control module 40 operates the stimulation module 42 to cause the amplitude of stimulation to slowly increase over an interval such as 5-15 seconds to the amount used in the prior therapy session. The system "ramps", or transitions otherwise, into the same stimulation protocol parameter values used at the end of the prior treatment session including operating the stimulation matrix in a selected manner.

FIG. 9b shows a sample introduction screen provided to a new user as part of an onboarding program introduction 102 defined in the onboarding module 50h. The screen displays an instructional video selected from the reference module 50b that is narrated by a clinician and provides education about a peripheral target such as the SAFN, discusses the mechanisms of action for treatment of a disorder, includes a lesson with instructions on how to apply the device correctly to stimulate the target nerve, and includes other information that introduces a user to the therapy such as how to use the stimulation matrix and modify stimulation parameters.

FIG. 9c shows an example of predefined treatment regimens. These include a curated "Restore" program which provides initial induction stimulation on a more intensive schedule (e.g., daily or longer sessions), and a "Maintain" program which provides a less intensive program of therapy maintenance (e.g., every other day, or 2-3 days a week, or shorter sessions). In an embodiment, both the Restore and Maintain programs are structured to guide a user to provide therapy according to a pre-defined regimen. However, in embodiments a user is permitted to customize the programs according to a set of permissions of allowed adjustments and ranges that characterize scheduled events.

FIG. 9d shows a Treatment ("Treat") screen, with a timer and controls. The bottom of the screen provides a location for providing notifications during a therapy session that prompt a user to engage in various types of treatment events such as viewing educational content or completing survey items. The screen also provides control of a stimulation montage including stimulation strength and location.

FIG. 9e shows a screen where users are surveyed to provide the anatomical location of stimulation evoked paresthesia and may be followed by screens surveying the strength and quality of the paresthesia.

FIG. 9f shows a history screen with treatment calendar having icons that inform about provision of treatment and compliance. The screen may include notifications containing compliance scores, progress updates, reminders, or encouragement (e.g., "Excellent Job"; "You still have a survey to complete") that can be presented at the top of the screen based upon assessment of the status of sets of calendar events in relation to compliance criteria of the treatment regimen.

FIGS. 9g and 9h provides features related to user input and tracking of symptoms at baseline (e.g., obtained during onboarding) and then at later times in the therapy, respectively. The symptoms are scored qualitatively using symptom assessment criteria as "normal", "moderate" or "high" which are defined for ranges of symptom scores.

FIG. 9i provides features that provide tracking progress feedback to a user.

FIG. 9j provides features of providing positive feedback and goal announcements as part of coaching provided during the therapy interval. A treatment goal may be set as default or may be derived during the onboarding process 100 or afterwards in step 142. Providing encouraging notifications as part of coaching can help motivate users as the therapy progresses.

FIG. 9k provides features of informing users about advancing to a new stage of the treatment regimen such as from induction to maintenance.

Anatomical Data and Device Mapping.

In embodiments, training operations of step 104 or coaching operations of step 140 are used with anatomical images. For example, in step 104 the coaching module 50h provides user instruction on how to position the device correctly for intended stimulation of an anatomical region as shown in FIG. 10b. An image may show or superimpose the device correctly positioned and worn on a leg.

In embodiments the training 104 includes obtaining user input about anatomical data and stimulation related sensations. For example, users are surveyed 142 to provide data related to device placement and their assessment of stimulation and whether successful nerve recruitment has occurred. This includes being shown a display of a relevant body part such as a leg and foot in the case of SAFN stimulation, or arm or hand in other application. The user can move a virtual image of the device along the image until it corresponds to the location that the user has decided to wear it or simply draw an "x" where the device is worn. The training module 104 can provide feedback about if this is correct or incorrect. The user may also be surveyed about the location of skin stimulation or paresthesia. User friendliness and training outcome can be improved by selecting or adjusting an anatomical image based upon user demographics, gender, height, weight, body type, or other characteristics of a user that has been input by a user. If a user indicated they are a 65-year-old, black, female then an image of a leg is selected from a library of leg images or line art representations stored in the reference materials module 50b. If the library contains images for 3 age ranges, 2 genders, and 4 races (e.g., Black, White, Asian, Latino), then the image library of the module 50b may comprise 24 images.

Alternatively, during onboarding user surveying 108, the onboarding module 50e can prompt a user to take a picture of their own leg with and without the wearable device attached. The EM module 46 can instruct a user to operate a user device digital camera to obtain an image of the device being worn that is stored in the reference module 50b. At scheduled times during the treatment interval, as part of coaching 140, this image can be presented to a user by the App 21 prior to allowing user to start the stimulation, to increase consistency of device placement. Additionally, the system can survey a user to obtain additional photographs of the device being worn according to a schedule. This may require that a photo be obtained at the start or end of every treatment session. The image is stored in the user log. It can be transmitted with log information to remote computer 20f and reviewed by a medical professional and to determine if device placement is consistent and correct.

Virtual/Augmented Reality Mapping.

In embodiments, the digital ecosystem module 50 includes a virtual module 50a that provides virtual reality (VR) or augmented reality (AR) functionality in combination with camera/video images recorded by a user's smartphone user device 20a under control of the App 21. For example, the module 50a software merges the image captured by the camera/video with an image indicating where a user's saphenous nerve is likely to be (e.g., previously established through imaging data, or other mapping data that has occurred for the user, or based upon population data), to provide for improved nerve targeting. Mapping data can include locations where successful recruitment of the target nerve previously occurred. For example, if a doctor performed assessment of the patient and placed the stimulation matrix 16 at a location, then the associated VR image of that positioning is superimposed as a ghost image upon the real time image recorded by the camera. The user can adjust the actual real life (RL) position of the device until it overlaps with the virtual image. The use of VR helps confirm correct placement of the stimulation matrix when used independently at-home. The VR/RL comparison can be stored or transmitted to a computer 20f at a remote location to allow remote guidance to the patient.

Feedback Using Sensed Data

In embodiments, the system includes a sensing module 44 configured to record and process SNAP and/or EMG data. The sensed data signal may be filtered and provided to display or a speaker to allow a user to hear an evoked activity in contrast to background activity. The recorded signal may be averaged over a selected period such as 30 seconds (e.g., 5-second segments with an average of 6 recordings) prior to being presented to the user. The sensed data can also be presented on a grid which shows a heat signature of the SNAP amplitude (or other measure of evoked potential strength) as a function of where the stimulation signal centroid was located on stimulation matrix.

In an embodiment, sensed data can be used to enable adjustment of a stimulation signal that provides neuromodulation but is below sensation threshold. This may be helpful if treatment is provided while the subject is sleeping. In a method, the stimulation amplitude is increased until the subject confirms sensory perception of recruitment. The amplitude level is then decreased in steps (e.g., 5%) to determine if the stimulation is still sufficient to evoke a neural response.

In embodiments, sensed data may be used to assess or confirm nerve recruitment related to selection of amplitude, location of stimulation (i.e., field geometry), and selection of stimulation montage from a set of defined montages. This may occur in a closed loop manner that automatically adjusts stimulation parameters (amplitude, location) to maintain a sensed response from the nerve that meets at least one detection criterion.

When using SNAP recording and detection to confirm SAFN recruitment (for implantable or wearable devices), at least one of a first pair of electrically conductive pads can be applied above the stimulation matrix (to record antidromic potentials) and a second pair can be placed below (to record orthodromic potentials), or both can be used. When recording both antidromic response and orthodromic responses as objective measures, the two measurements can be compared, or combined, or independently assessed to confirm recruitment. Confirmation of nerve recruitment can require at least one, or both, measures to be detected. Further, the relative delay (nerve conduction velocity) of the two types of measured evoked responses can be compared as part of response assessment.

When sensed data are used to confirm recruitment and set stimulation settings, in either open-loop or closed-loop embodiments, then SaphLevel and SaphLocate features of the invention can be used to maintain "recruitment" of the target nerve. For example, the non-primary channel amplitude weightings can be set above zero and increased to achieve or maintain successful recruitment of the target nerve. Sensed data may also be used by the system in closed loop systems that use control-laws to maintain recruitment amplitude or latency measures within in a selected range.

Physician Locator/Connect.

In embodiments, triggers are defined in the system 10a that prompt a user to connect with a physician for an in-person or virtual visit. In step 126 the system can prompt a user to connect with a physician if the user profile indicates the patient has may be inappropriate for the therapy (e.g., suffers primarily stress incontinence rather than OAB). In embodiments, negative outcome treatment events as may be assessed when assessing treatment progress in step 144 serve as triggers that cause the system 10a to provide a defined contingent operation. The system may transmit a flag value to a remote computer 20f which is used to modify a patient's record, and which can be scheduled for review by a qualified medical professional of a service provider. If merited this may prompt the user to be contacted in a defined manner or may cause a remote telemedicine or in-person visit may be scheduled. Additionally, in embodiments, in step 144 the system may implement a physician locator/connect feature that includes any of the following operations. The locator/connect feature is implemented by the locator/connect module 50k to use the patient's location (assessed by address, zip code or other geolocating method) to provide the user with a list of nearby "EBT-Approved" urologists (or urology practices) that the user can then select. The list may also be based upon additional information stored by, or requested by, the system, such as the user's age and medical/medication history. A patient can select the physician, may be given the physician's contact information, be presented with the option of being connected to the office to schedule an appointment, or can schedule an in-person or video consultation using the systems' software of the locator/connect module 50k. Patients can be connected to a professional contingently based upon having a sufficient number of remaining purchased "credit units". Medical sessions can also occur using texting or chat functionality or cellphone.

Upon acceptance of a user's request for medical consultation, as part of step 144 the locator/connect module can operate to request user permission to send information to a doctor (i.e., a computer 20c in the doctor's office). In an embodiment, the user must actively provide permission for items to be sent to the doctor and provide a signature on the touch sensitive screen of the user device 20a which is presented by the locator/connect module 50k. The information may include: insurance information, billing and address information, relevant medical history, and all information stored by the system 10a on the neurostimulator 12, remote computer 20f, or user device (e.g., user's smartphone 20a operating the App 21). The information can also include, for example, all information obtained during patient onboarding, user profile information, answers to survey items presented to the user, log information including history of stimulation including durations and parameter values, summary of compliance, notes from any prior consultations with medical professionals (which is associated with a user's unique ID number and stored in the cloud), and other information related to the user's medical history. When a consultation session is scheduled, this event is added to the calendar of the system's software or the calendar of the smart-device so that a reminder may be provided.

Negative treatment outcomes assessed during step 144 can also lead to additional events 134 such as education with webinars on lifestyle changes or other medical treatment alternatives, and can lead to the suggestion of incorporating alternative interventions (e.g., provision of software-based therapy) that can be added to neurostimulation therapy (by a user or physician). If a user watches a video on implanted neurostimulators and wants to meat with a physician to discuss further, then the locator/connect module 50k can restrict candidate physicians presented to the user to those that are qualified or otherwise selected to provide that therapy.

In an embodiment, if a physician or practice is selected by a user operating the locator/connect module 50k, then the user is provided with the option of choosing involvement of the physician as part of their treatment plan and can opt to share summary or real-time data on an ongoing basis.

In embodiments, the digital ecosystem provided by module 50, includes functionality for a physician locator including module 50k, which may be triggered by events such as: if a positive response is obtained in step 108 during onboarding to a survey item or set of items designed to identify conditions requiring medical assessment in step 126; as part of step 126 due to a user's medical history or medication information; if during treatment a user's therapy goal is determined to fail in step 144 then the user is prompted with an option to be connected with a nearby physician/clinic; if a user requests an office visit through the App 21 as part of step 146, for a reason known only to a user; If as part of step 148 which includes a scheduled remote review by a medical professional of a user's data (e.g., as defined in the treatment schedule or if this becomes remotely scheduled due to detection of a medical event such as a lack of treatment benefit); if it is prompted in step 148 due to a flag in the user profile due to an expired prescription, or if a doctor has reviewed other information at a remote site 20c and determined a medical referral is warranted.

In embodiments, connection to a local physician in step 146 occurs through a telemedicine application of the telemedicine module 50d that provides software for videoconferencing with a doctor. This can allow for requesting or scheduling an office or telemedicine appointment, the provision of the medical office contact information, or the provision of a remote meeting with a nurse practitioner who may in turn connect the user with an appropriate local physician.

A local physician is identified as a physician located from a database of the system which will look up a local doctor using at least one of the following: the location of the user identified by GPS or zip code; insurance company information supplied by a user; information about a user's primary care provider or urologist which is stored in the system; or other method. Further, the method used and the doctor selected may be adjusted based upon what factor(s) prompted the user to connect with a doctor such as failing a therapy protocol, answers to a survey that suggested a constellation of symptoms which met criteria for a referral to a doctor for further evaluation (e.g., evidence of non-OAB complications, medical conditions, or disorders potentially worthy of assessment).

Contact Logs

In addition to the therapy program 130 updating the log information as part of the startup/shutdown process 132, this can occur in step 150 in relation to connecting with remote medical professionals in step 150. In an embodiment, the system contains computer readable software code in the user interface module 48 which manages telehealth operations of the telemedicine module 50d and operates the log module 50m to create a data log of a user's remote telehealth history. The fields of a contact log allow the tracking of time and content of any user messages which the user may send to a medical professional at a remote medical service. Additionally, the contact log managed by the log module 50m stores data related to the user providing "event tagging" of potential relevant medical events as part of step 150 which is invoked when a user enters information related to an event that they want stored or reviewed (e.g., emergence of urinary retention). The log module 50m can also log time and content of questions submitted to a remote service (and answers received). These may include voice recordings or text messages which are transmitted to a computer 20f of a remote service for review or information stored locally on the system 10a for later upload and review.

Calendar Exports/Milestones Notifications

In embodiments, the digital ecosystem module 40 provided on a user device 20a through an App 21 is designed to integrate with a smartphone calendar program. Accordingly, scheduled therapy events defined in the Renew/maintain program can be presented on the calendar screen (see FIG. 9f) and can cause the App to provide the user with "push" or other notifications under the Alerting module 50j. However, the communication module 45 can communicate export data from inside the App 21 as events or activities with defined reminders to a calendar specified by a user (e.g., exported into a user's Outlook or Google calendar using an ".ics" or ".vcs" file). Historical events and status (e.g. complete/incomplete) and scheduled future events are retained by the App 21 (with logs or other information stored on the device 12 and or remote computer 20f) to form a complete record of events. This includes for example: when stimulation sessions were scheduled and were skipped or occurred; "winning moments" such as when a patient achieved specific therapy goals (e.g., goals assessed over a selected period, "Zero leaks for the last 5 days", "Slept through the night for the previous 3 days", or "Stimulated every day for 14 days, i.e. 100% compliance, etc.)

Similar to integrating log file information for the purposes of calendar exports, the coaching module 50h can apply compliance criteria across the integrated log file information that may be stored on the neurostimulator 12, user device 20a, and/or remote computer 20f. For example, if the user provides 1 or more stimulation sessions using the neurostimulator 12 without the user device 20a then the compliance criteria must be applied to the integrated log file after it has imported usage data from the neurostimulator 12. In embodiments, this is defined to occur at the start or end of a therapy session 132, or otherwise.

Implantable Device.

The invention may be realized using an implantable device rather than, or in addition to, a wearable neurostimulator. The implantable device can have a cylindrical shape like a BION or e-Coin shape or can use paddle leads or other electrode form factors. Alternatively, the form factor may be a slightly concave housing that corresponds to the notch that runs alongside the tibia. It may have only 1 contact for providing stimulation (referenced to the housing) or may have a set of 2 or more contacts, in which case, controls and methods for field steering disclosed for a wearable system are similarly used.

When stimulating the PTN, candidate stimulation locations can be confirmed by visually or otherwise detected motor activity (e.g., flexion of the first toe or fanning of all toes), such as changes in EMG or motor evoked potentials (MEPs). In contrast, candidate locations for SAFN stimulation can require the subject to confirm evoked sensations such as paresthesia or can be confirmed using SNAP detection. For treatment using the SAFN, a user's subjective assessment of implantation sites for one or more electrode contacts) may be hindered if performed after providing local or general anesthesia (e.g., lidocaine or propofol) due to interference with the patient's ability to confirm stimulation induced sensation. A two-stage implantation technique may be required when using subjective assessment. Accordingly, in an embodiment, a first step includes assessing a candidate implantation location and/or a stimulation parameter by: a) transcutaneous stimulation corresponding to candidate implant points along the leg, or b) percutaneous stimulation at candidate locations (which may include depth) such as provided by an insulated needle with a conductive tip (or temporary subcutaneous lead). A device for cutaneous electrical nerve stimulation and "nerve mapping" is the Stimuplex® Pen configured to work with the HNS COMPACT Nerve Stimulator. This type of technology has been shown to provide accurate assessment of nerve recruitment (e.g., Bosenberg A T., et al, Paediatr Anaesth. 2002 June; 12(5): 398-403).

Candidate locations can be assessed by subjective measures, nerve mapping, or the combination using measures related to at least one of: minimum recruitment threshold; maximum comfort/tolerance threshold; pain threshold; a difference such as maximum difference between recruitment and pain threshold; type, degree or region of induced paresthesia; presence/absence/level of co-activation of adjacent nerves or muscle, distance from a blood vessel, etc. Imaging data obtained using, for example, ultrasound, X-Ray, or MRI can also be used to identify candidate implant locations.

When the neurostimulator of the system 10a is realized as an implantable device it may be programmed to transition from an induction to maintenance schedule according to various rules such as: a) automatically after a predetermined interval calculated using an internal counter or clock; b) if a user device 20 communicates an appropriate command either due to user selection or due to a predetermined interval lapsing as calculated by a counter or clock; or c) due to schedules, rules, and strategies described for the wearable device.

Treatment of Medical Disorders and Unwanted States.

In embodiments, system may be applied to treat, prevent, or improve many unwanted conditions, symptoms, and disorders using stimulation of the SAFN or other nerve. These include for example, urinary or fecal incontinence, sexual dysfunction, chronic pelvic pain (CPP) syndrome such as Orchialgia (persistent pain in the scrotum), ovarian pain/fibromyalgia, and interstitial cystitis (IC)/Painful Bladder Syndrome (PBS). Treatment can also be related to vaginal dryness and promotion of post-pregnancy, postpartum vaginal health. In addition to idiopathic OAB or underactive bladder disorders that may occur in the absence of any underlying neurologic, metabolic, or other known causes, treatment may be provided to improve symptoms related to conditions that may mimic or evoke OAB symptoms, such as, urinary tract infection, benign prostatic hyperplasia (BPH), bladder cancer, bladder stones, bladder inflammation, or bladder outlet obstruction or due to procedures such as indwelling urinary catheter induced lower urinary tract infections (LUTS), radiation induced changes of bladder or bowel activity or sensitivity, post-prostatectomy OAB or other interventions of the prostate. Certain medications may lead to OAB symptoms which may be improved by neurostimulation, especially of the SAFN. Treated conditions can also include non-obstructive urinary retention, genitourinary syndrome associated with menopause, enuresis, dysuria, erectile dysfunction, female sexual dysfunction and disorders. Further conditions may include constipation and irritable bowel syndrome (IBS & IBD) and related symptoms. Other peripheral nerves in the legs, arms, body, neck or head (e.g., cranial nerves) may also be suitable targets for treatment of these and other conditions and disorders. In embodiments, the treatment system can be configured to provide both stimulation and digital health support configured to treat disorders such as: Radiation induced: OA Bladder & Bowel; Nocturia; Post Prostatectomy OAB.

The disclosed neurostimulation system may be used in treatment of pain (especially limb pain), reduced limb circulation, unwanted or hypo/hyper muscle activity (e.g., restless leg syndrome) and a host of medical disorders, via modulation of peripheral and/or central mechanisms. The system operation is adjusted accordingly including, for example, treatment, coaching, user surveying, and symptom assessment and tracking of therapy progress.

Not to be limited by theory, although the basis and mechanisms of acupuncture are not very well understood, candidate stimulation sites may be selected based upon locations used in acupuncture or electroacupuncture, and then adjacent nerves can be assessed using various stimulation parameters and treatment schedules to determine if benefit of nerve stimulation can be obtained. Stimulation sites and parameters can also be derived using data from animal models.

In embodiments, the wearable neurostimulation system is used to treat pain such as by blocking, masking, or competing with pain signals from the leg or foot. In an embodiment, the stimulation treatment is used to treat edema, either as an adjunct to providing stimulation for OAB, or as a separate treatment.

Decreasing Risk for Skin Events, Pressure Ulcers, and Injuries (PU/PI)

In embodiments, the wrap secures the stimulation matrix against a user's skin with a low pressure that is sufficient to prevent it from slipping down the leg. This allows the wrap to use stimulation matrix pads with little or no stickiness or "tack". Alternatively, the wrap is configured to provide a range of pressure if a user secures it moderately or tightly. In embodiments, the device, stimulation matrix, wrap, or other component of the system 10a incorporates pressure management and control into its design. For example, a user control enables the user to adjust a spring compression pressure, or tightness of the wrap, which biases one or more pads against a user.

Unlike percutaneous electrode treatments which use skin piercing needles transcutaneous stimulation with pressure can avoid various complications and risks to the user including infection, pain, and the reliance on medical professionals to accomplish treatment. While using pressure with one or more matrix pads may have advantages, it can increase risk of skin problems especially in users with medical disorders or certain skin characteristics. Electrical stimulation can produce skin events (e.g., irritation) which are typically minor and disappear shortly after stimulation, but it is important to identify skin events that may develop into adverse events (AEs) for the user. The NiNA system provides features for managing pressure and decreasing risk of skin events emerging or progressing in severity.

The term "skin event" is an umbrella term that can refer to the terms "pressure injury (PI)", "pressure ulcer (PU)", Medical Device Pressure Injuries (MDPIs) "suspected deep tissue injury" (sDTI), "skin tear", etc. all of which indicate an injury or potential injury to a user's tissue. A sDTI is defined as a purple or maroon localized area of discolored intact skin or blood-filled blister due to damage of underlying soft tissue from pressure and/or shear. NPIAP 2019 guidelines and WOCN 2016 Guidelines for Prevention and Management of Pressure Injuries are incorporated by reference herein, and features of the invention have been designed to address and adhere to these guidelines.

The mechanisms of pressure injury and overview of these guidelines support that, in embodiments, a wearable nerve stimulation system can incorporate moderate pressure levels to its stimulators or sensors using short treatment intervals (e.g., a range of 15 to 30, 60 or 120 minutes) with low risk of causing MDPIs and without transgressing relevant care guidelines.

As shown in FIG. 8b, scheduled treatment events related to assessing risk for AE's 154 such as skin events provide, and can be adjusted based upon, skin risk 164 scores as derived in steps disclosed in FIG. 8c. For example, a risk score is created during onboarding 100 or due to a user providing input which indicates increased risk when surveyed in step 142. Skin risk can also be adjusted based upon user input to the system due to skin risk symptoms noticed by a user. Users can provide information about their symptoms such as by event tagging 150, using an event tagging screen including buttons for logging adverse events such as skin events. An event tagging screen may include options such as redness, irritation, pain, discoloration, post-stimulation skin sensitivity or dryness, open sore, infection, blister, etc. In step 152, event risk operations can include invoking the steps of FIG. 8c. For example, user survey data can increase a skin risk score 174 if users have indicated that they have increase risks such as more delicate skin, have medical history or conditions that increase risk of skin events.

In embodiments, during onboarding or afterwards, users are surveyed about skin risk 120 the presence of conditions that produce greater susceptibility for skin bruising, injury, irritation, tearing, or ulcer. Users are surveyed specifically about their arm, leg or other areas where stimulation will be provided with respect to presence or severity of any the following: Eczema; above average propensity for skin irritation or skin dryness; skin sensitivity; easily bruised; diabetes; lack of sensation; neuropathy; spider veins; varicose veins; skin allergies; sensitivity to hydrogel; or other condition that can increase risk of skin injury or discomfort. If the user indicates any sensitivity or presence of these conditions during onboarding or at any point during therapy, the system can contingently implement operations that allow the condition to be avoided, or surveyed about and tracked. The operations may include shortening a daily 30-minute stimulation treatment session into two 15-minute sessions to provide a break for the skin of the user. The operations may include prompting a user with a treatment reminder which also includes a message to alternate the side of the body used to provide treatment stimulation on sequential treatments. The operations may include fixed or adaptive algorithms that are configured to determine occurrence or persistence thresholds for adverse events which trigger contingent operations. For example, an operation can be defined in response to a user indicating the emergence of bruising under the stimulation matrix in which a user is prompted to notify caregivers and health care professionals, or such notification is automatically triggered for a third party as defined during setup or by user permission parameters.

Pressure Adjustment.

Too much or little pressure may both present problems. System features enable users to adjust the wrap compression level appropriately. Too much pressure will increase risk of skin events. When the wrap is made of an elastic material, the material may be selected to provide a selected range of compression. As part of step 178, to further adjust pressure a user may be instructed to pull the one arm of the wrap through a buckle on the other arm of the wrap until the wrap is the same circumference as their leg, and then to continue to pull until a selected number of markings provided visually on the wrap pass through the buckle. This will produce a corresponding pressure between the stimulation matrix and a user's skin based upon the wrap elasticity. As a result, a desired pressure in an expected range is applied to the matrix (e.g., a range of 0.5 to 1.5 PSI).

Additionally, the wrap may incorporate buckles with incremental grooves (similar to buckles used on ski boots). After the wrap is secured to a user's leg, the user fastens the buckle using a first, second, or third, groove each of which are associated with a prespecified amount of pressure. Additionally, finer adjustments to pressure can be obtained using screws that can be manipulated (wound) to constrict a band realized within or upon the surface of the wrap to decrease the circumference of the wrap. In embodiments, the band may be configured with a manual air pump. In that embodiment, the user squeezes a balloon similar to what occurs when blood pressure it taken using an arm band. Similarly, a meter is incorporated into this solution which allows a user to measure the pressure applied to the band. The wrap may also be configured with adjustable tension controls such as a ratchet strap or elastic belts with buckle holes. The matrix may be provided with springs which reside between the device 10 and one or more pads of the matrix 16.

User Input, Sensed Data, and Assessment.

A PU/I or potential PU/I may be preceded by tissue that is painful, firm, mushy, boggy, warmer or cooler as compared to adjacent tissue. As shown in FIG. 8c, in step 170 users are educated about these skin event characteristics and in step 172 users are surveyed about PU/I presence or severity.

User data obtained during the skin risk assessment 120 of onboarding 100 or during therapy during step 142 can be used to adjust risk scores 122. Users can be asked about risk factors including, for example, diabetes mellitus, peripheral vascular disease, cerebrovascular disease, sepsis, and hypotension (low blood pressure can decrease capillary pressure), or these risk factors can be entered into the system during onboarding by having the system communicate with an EMR system that is associated with the patient. Conditions such as diabetes are relevant to risk of PU/I since this may decrease a user's ability to feel pain related to pressure or pressure injury and who may be slower to provide appropriate intervention.

Data obtained during the onboarding process may cause contingent adjustment 126 of a schedule of system prompts for the user to monitor their skin for potential problems. The system may also set the state of a status flag to "true" for a variable of "at increased risk for skin problem" or otherwise increase a risk score 122. The system may also adjust characteristics of the treatment such as setting limit for the minimum interval between, frequency, or length of a stimulation session. If the flag status is set to true then several actions may occur contingently 126 such as a) causing a visual signal such as a red LED or text message to be displayed at the start of each stimulation treatment to indicate to user or caretaker that the patient is at an increased risk for skin events, b) reminder are provided to decrease risk such as to alternate legs on sequential days or weeks, or to avoid a leg with a sore or, c) the patient can be reminded to apply antibiotic or moisturizing cream after providing stimulation.

Risk scores may also be increased due to surveying 120 that incorporates using survey items from the Norton Scale and Braden Scale (incorporated by reference herein) which are commonly used prediction tools, or survey items based upon those scales. For example, a Norton score of 16 or less, or Braden Scale score of 18 or less, indicates increased risk for PU development and may increase a skin risk score 122 of a user. Use of a validated scale for PU/I risk, or a modification of these scales, is used to adjust the risk score 122 in users at higher risk due their answer to 1 or more survey items.

Additionally, in step 120 users can be surveyed with items relevant to their risks for injury related to pressure, friction or shear. Users can also be surveyed about sensory perception, moisture, activity levels, mobility, nutrition, physical condition, mental state, activity, and mobility. Users can also be surveyed about characteristics such as presence of dry skin, sensitivity, irritation, and skin conditions (e.g., cracks, scarring). A more frequent schedule of skin risk assessment or education may be scheduled if a user or caregiver notes any reason for increased risk (e.g., noting redness after stimulation, skin dryness, sores, or cracking at stimulation site) as part of event tagging 150.

Adjusting Risk Scores and Contingent Intervention and Protocol Adjustments.

If a user inputs information into the system that indicates increased risk then the system may adjust a skin risk score and operate to contingently provide operations that decrease risk of injury, or which can decrease the severity of injury, or which aid in injury recovery. Risk scores can be quantitative and qualitative and can be stored in a look-up table that is operated upon by rules defined in the treatment algorithm. In addition to using skin risk data to adjust an overall skin risk score, contingent operations carried out in steps 126 and 176 can be defined according to values that are set for particular items. For example, if a "dry skin" variable is set to true then a user can be reminded to apply moisturizing cream after treatment, while this would not occur if the "diabetes" variable is set to true.

If a user's score for a PU/I scale exceeds a selected threshold, then a contingent operation occurs such as: the patient is alerted to the increased risk, or interventions or protocol adjustments contingently occur.

While skin events can develop immediately, these can also develop within 2 to 6 hours after insult. Accordingly, the system 10a can be configured to query a user in step 172 about a potential skin event before or after a stimulation session or this can be scheduled to occur several hours or days after the session has ended since users can appear to be free from the signs immediately after an insult. The NiNA system provides features that are appropriate to a user's risk level such as increase instructions and reminders related to pressure injury prevention when subjects are more at risk.

Pressure Mechanisms/Advantages

Use of pressure may decrease risk of skin-related discomfort and stimulation side effects since it can: a) decrease the stimulation level needed to recruit the nerve; b) decrease the spread of energy on the skin surface rather than through the skin, c) decrease impedance similar to that achieved by abrading the skin, and d) decrease the way the stimulation is perceived (e.g. by adding competing sensory information). Empirical measurements have shown that pressure can decrease impedance by as much as 80% using a force of 2N to 4N. Without being limited to theory, applying pressure to cause the stimulator pad to push away tissue and fluid may improve nerve recruitment due to a) a decreased the distance between the target and the stimulation signal source, and b) changing the shape of the stimulation signal field between the two or more stimulation pads of a stimulation circuit (e.g., decreased tissue volume between two pads can increase the signal density). Decreasing pad-to-target distance (displacing the stimulator closer to the target nerve) and the tissue volume between stimulation pads may decrease the signal amplitude required to reach nerve recruitment threshold and decrease unwanted co-activation of adjacent non-target tissue. For example, for a user with low skin event risk 176 if during onboarding upon being surveyed 108 paresthesia is not reported, then a user may be instructed to increase pressure level of a stimulator, the matrix, or the wrap.

If a user's risk score for skin events is below a selected level the system can operate to provide selected features and operations 176 that incorporate the use of pressure during treatment 178. Biasing the location of an electroconductive pad deeper into the skin can improve both nerve recruitment and sensing of evoked physiological activity. As well as decreasing distance between the stimulator and the target, pressure may also serve to decrease impedance which facilitates stimulation and sensing of evoked nerve activity. For example, for a user with low skin event risk 176 when stimulating the posterior tibial nerve, use of pressure 178 can include two opposingly arranged stimulators that press medially and laterally into the skin on the posterior side of the leg to improve nerve recruitment.

Pressure may be used to alter the sensory experience related to stimulation by increasing sensation of paresthesia or decreasing the amount of perceived pain or discomfort associated with a particular stimulation intensity. Not to be limited by theory, one mechanism for this is activation of the nerves that sense pressure in the skin may produce signals that interfere with signals produced by nerves that sense and transmit information experienced as pain.

Pressure can assist when treating patients with having excess tissue between the conductive pads and the target tissue. For example, use of pressure may be adopted if during onboarding, upon being surveyed 108, for users who indicate characteristics that may suggest hurdles for nerve recruitment (e.g., overweight, an elevated BMI, believe they have "thick" skin, or those reporting edema) and who may have trouble with successful stimulation of the anatomical target. Alternatively, adjustment of pressure can occur if during training 104 users are not able to recruit the nerve (e.g., due to anatomical differences in the location of a target nerve which hinders successful nerve recruitment or other factor).

Applying pressure to a stimulator or otherwise causing displacement of a stimulator/sensor towards an anatomical target can enable or improve therapy. Further, providing for features that deform skin 178 using pressure, suction, or tension (e.g., pulling skin outward) to enable stimulators to improve the location for targeting a nerve, can allow greater charge to be directed towards a target and provide advantages. For example, the device or matrix may be designed to pull, or otherwise deform a body region to change its shape or to decrease the distance between a stimulator and a target nerve (e.g., compressing tissue surrounding the posterior tibial nerve from the opposing lateral and medial aspects will decrease the distance between the skin and target nerve).

In embodiments, one or more of the stimulation pads 16 can have a raised surface that is configured to press into the patient's skin and to bias the stimulator towards the target tissue. For example, at least one stimulation pad surface of the stimulation matrix pads can be formed with a raised/offset surface such as a convex surface. Alternatively, the stimulation pad surface may be formed with one or more "dome-like" bumps that serve to direct the source of energy slightly deeper towards the target nerve and decreases the stimulator-to-target distance and amount of intervening tissue. The shape of the bump should be formed to be smooth and shallow enough (e.g., less than 0.10 or 0.25 of an inch) that it does not cause too much pressure or sheer on a user's skin. In an embodiment, the stimulation matrix is configured with one or more stimulation pads with deformations in their surface that enable a portion of the pad to protrude into, or otherwise deform, the patient's skin.

Figures 11, 12:
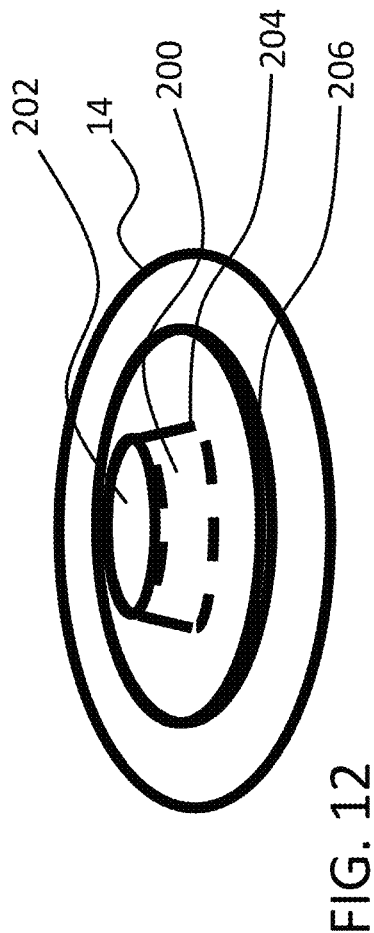
FIG. 11 shows long term study results of benefits after 6 and 12 months of treatment supporting an induction period of over 21 days for OAB treatment using daily stimulation of the SAFN.
FIG. 12 is a schematic drawing showing a projecting flange extending from a supporting ring or push nut adhered to a stimulation pad.

In embodiments, as shown in FIG. 12, the stimulation pad 14 has a projecting flat-rimmed flange 204 similar in shape to an axle hat nut or push nut. The flange 204 includes an annular wall 200 extending from a conductive support ring 206 which is adhered to the stimulation pad 14. The flange 204 extends from a plane of the push nut or support ring 206 to a an upper or top surface 202 of the flange 204. For example, electrode surfaces contain shapes formed like Hillman or Everbilt axle nuts, such as the ⅝ inch circular push nut having a diameter of about 0.5 inches, a flange diameter of 0.2 inches, an annular wall of 0.2 inches connecting the two at 90-degree angle and terminating with a rounded top 202 that is pressed into the user's skin by the tension of the wrap. Alternatively, it may have a diameter of between 0.4 and 0.7 inches, and a flange diameter of between 0.1 and 0.3 inches, and an annual wall of between 60 and 90 degrees with a height of between approximately 0.1 and 0.3 inches. Using this "cap" design and electrode gel the inventors pilot work found perceived paresthesia was stronger, occurred at lower amplitudes of stimulation, and was more easily obtained.

It has been found by the Inventors that applying a pressure of about 1.65 lb. (0.75 kg) with a circular stimulation pad of 1.25 inches, to yield a force of 1.34 PSI can improve nerve recruitment: the test was done with circular electrode pad of 1.25 diameter, and PSI is calculated by dividing 1.65 by (Pi*(1.25/2)^2). In embodiments, between 1 and 2 PSI is applied to each of one or more of the stimulation pads either by default or by user selection. The application of pressure is used to improve at least one of: a) the probability of nerve recruitment, b) the level of nerve modulation, c) the selective activation of the target in the absence of co-activation of adjacent non-target tissue d) the perception of the stimulation on the skin of the user and e) the amplitude of the stimulation signal associated with the pain threshold.

Pressure can also be used to decrease the amplitude of the stimulation field necessary to recruit the nerve (e.g., by decreasing stimulator to target distance), and to increase the sensation of, or area of, paresthesia associated with recruitment of the nerve (e.g., by inducing pressure signals in the nerves that can affect sensory gating or which can cause lateral inhibition). In embodiments, from about or 0.4 to 0.6, or 0.6 to 0.8, or 0.8 to 1 pound of compression is applied to at least one stimulation pad 16 or across all pads of a matrix. In embodiments, the components of the system 10 are designed to enable a user to provide an adjustable amount of pressure within a range of about 0.5 to 3.5 PSI, and more preferably, between ~1.0 to 2.0 PSI (120 mmHg).

Pressure ulcers can develop when persistent pressure obstructs healthy capillary flow, leading to tissue damage and necrosis. Healthy capillary pressure generally ranges from 20 to 40 mm Hg (0.77 PSI), with 32 mm Hg considered the average. When pressure is above this range it can impede blood flow to tissue. Illness severity and comorbidities can reduce pressure required to obstruct capillary blood flow. Accordingly, pressure can be set in relation to a user's blood characteristics.

Managing Pressure and Skin Event Risk

In embodiments, the system incorporates features into the physical design of the device, into the parameters of the treatment protocol, and into the digital ecosystem that mitigate risk of PU/I, promote treatment, and provide supplemental care to align with relevant guidelines. Good skin health can be promoted by default features or that may be adjusted according to one or more risk scores, or changes in risks scores, or users preferences 176 associated with the emergence of a skin event For example, the system lowers risk of injury through features related to:

a) Behavioral modification such as can occur in step 182 promotes user behaviors that decrease risk of injury. For example, patients or caregivers are instructed or prompted to alternate leg or arm used for stimulation to avoid repeatedly using the same treatment site. If a skin event has been detected then the system can prompt a user to use an alternate treatment location until recovery. If a user has indicated dry skin the system can prompt the user to apply moisturizer at the completion of the therapy session. The user or caregivers can also be surveyed about soreness or other skin/muscle discomfort as a scheduled event or due to a decrease in usage so that they visually evaluate the treatment area. If opted by a user, the system can include reminders about applying ointments to skin after therapy.

b) Education such as can occur in step 186 provides information and education to users about skin events (e.g., provide educational notes that explain physical characteristics to notice such as redness that persists after therapy ends). Education can also instruct on how to check for signs of PU/Is.

c) Education such as operating the ecosystem to educate patients and caregivers about strategies to prevent PU/I's and tears, to promote PU/I healing. Education can also include providing information on nutrition, vitamins, supplements, and topical ointments that can assist with prevention and healing of PU/I's. Topics can include medical options such as the use of cytokine growth factors (e.g., recombinant platelet-derived growth factor BB), fibroblast growth factors, and skin equivalents. As well as material from relevant society guidelines. The education material can include information on topical medication ointments that can be provided after stimulation.

d) Education such as instruction for users and caregivers on how to adhere to national society guidelines through use of videos or informational "snacks" which are provided using visual or auditory messages and which may occur during therapy on the screen of a user device (e.g., bottom of FIG. 9d). Information "snacks" are provided on a user device display, as text messages or push notifications on a user device, or by sending e-mails from a remote server 20f.

e) Education such as promoting education on correct application, use, and removal of the stimulation matrix to reduce unnecessary shear and pressure forces on the tissue. Correctly securing the wrap to the leg will decrease these risks. Using more than one size of wrap and stimulation matrix which is selected to be appropriate for user's leg size can decrease risks of uneven pressure or incorrect fit.

f) Treatment protocol design such as can occur in step 180 having a stimulation treatment program with characteristics appropriate for a user's skin risk. For example, providing an alert to pause stimulation treatment and release the matrix pads from a source of pressure for an interval (e.g., 1-5 minutes) before continuing to provide therapy. This can also be realized by providing written instructions or automatic reminders to cause intermittent pausing of stimulation and pressure relief. The device can be removed, or pressure can be relieved, at approximately 5-, 10-, 15-, 20-, or 30-minute intervals instead of providing 30-60 minutes of stimulation continuously. Pressure relief allows the microvasculature to recover and perfusion of the stimulation site. Clinical guidelines vary but recommend pressure relief for at least 15 to 60 seconds at intervals of every 15 to 60 minutes. Accordingly, to decrease MDPRI risk a user can treat for an interval (e.g., 15 minutes), then treatment is halted and pressure is relieved: NiNA will prompt the user to pause and release the wrap tension for 1 minute before providing further stimulation.

g) Treatment protocol design such as adjusting the treatment regimen so that stimulation therapy occurs less often if skin events emerge or persist to allow sufficient recovery time. Since PU/Is may not to heal in a timely manner due to ongoing pressure by devices that are worn chronically or for extended periods. Although the device is only worn for 30-60 minutes and used daily during induction, a less frequent schedule may be helpful.

h) Nutrition such as realized in step 188 with users being reminded that proper nutrition is important (e.g., reminded to consume a minimum amount of daily protein and vitamin) since nutrition is associated with wound prevention and healing.

i) Nutrition and dietary support such as nutritional education, prompts, which are provided (and supplements shipped) that decrease risks posed by impaired neutrophil function, overproduction of reactive oxygen species, free fatty acids and inflammatory responses. These pathophysiologic changes contribute to direct cellular damage, vascular and immune dysfunction.

j) Personalized Pressure adjustment such as realized in step 178 decreasing pressure for patients who are more at risk using calibrated springs or manual/electric pumps to supply a selected ranges of pressure to the wrap. In an embodiment, the wrap is configured with settings or marking that allow the user to set the amount of pressure (e.g., pulling the wrap until a particular marking matches up with a different marking to provide a calibrated amount of tension). Further, wraps can be manufactured to provide high, medium, and low amounts of pressure. For example, adjusting elasticity/stretch characteristics or incorporating adjustable buckles, and other means for adjusting the strength of securing.

k) Personalized Pressure adjustment. Additionally, pressure can be modulated to be dynamically adjusted above and below a patient's blood pressure measurement which can be assessed by the system prior to therapy, or a blood pressure level that is estimated, or according to other risks or attributes of a user such as age, or data/measurements which can be made using sensors of the system or by independent testing which is related to SpO2 (Blood Oxygen Saturation level), pulse rate measurement, blood perfusion index and combination metrics which include, for example, both pulse and perfusion. Measures can include Plethysmograph and Perfusion Index Hydration, bioimpedance, average heart rate, and metabolism.

An individual's risk can be assessed as part of a "baseline assessment" provided by a doctor. The baseline assessment can also include making patient anatomy measurements (leg circumference; body mass index; severity or type of edema; presence of injury or vascular condition; varicose veins) and providing system components (wrap characteristics such as size, elasticity, or pressure; stimulation matrix size; pad stiffness or design including components that press into the user's skin) that are appropriate for the patient.

l) Bioimpedance assessment such as can occur in step 190, and includes assessing bioimpedance which may be used to provide body composition analysis that decomposes a user's body into four components or measures associated with, for example, fat, muscle mass, minerals, and body water. A suggested pressure setting, range of pressure, and stimulation protocols used during treatment can be adjusted based, in part, upon one or more of these measurements. Various sensors and stimulators (e.g., vibration, temperature, moisture, and ultrasound transducers and transceivers) may be incorporated into the stimulation matrix, the strap, or other system component.

m) Monitoring and Management such as can occur in step 182 including prompting and obtaining confirmation that a user periodically checks and provides input to the system which confirms the user has checked for potential injury. If the patient reports any discoloration, changing in sensitivity, or presence of pain then the patient can be referred to a medical doctor, a remote session is initiated, or the system prompts the user to use the other leg.

n) Monitoring and Management such as configuring the software to remind a user to check for sore, redness periodically before the system is worn, or on a future date since PU/I's can develop hours, days or weeks after insult.

o) Monitoring and Management such as adjusting the treatment program to survey more frequently or asking a user if the system can monitor more closely when a patient has more comorbidities or is in worse health (physical or mental). If the user allows this, then the user can then be provided with more frequent surveying or remote telemedicine support which includes visual observation of the treatment site by a medical professional.

p) Skin health tracking such as may occur in step 192 and include instructing a patient to take photographs that are logged and which can be sent for review to ensure absence of injury. In an embodiment, the system uses video or camera-based software to collect, assess, store, and submit image data of a user's leg using image logging. The data allows a user, professional, or custom software to monitor skin health status at the stimulation sites and enable real-time monitoring and early detection of changes to deter progression of new injuries. The image data may be assessed via remote monitoring of image data that occurs periodically, upon user request, or as prompted by software that evaluates image data. In an embodiment, the user can take a picture which is stored by the device 20a and/or transmitted to a remote computer 20f for visual review by a medical professional. The image data can include log data that enables comparison of current image data to prior image data, such as to images obtained 1, 2, 4, and 7 days prior. Software of the system can guide a user so that images are obtained with methodology for restricting the distance, angle, and lighting of images within acceptable ranges to augment consistency. The system can include an accessory that positions a user smartphone device 20a in the same position relative to a limb during image acquisition (e.g., a physical frame that is placed against the leg).

In an embodiment, surveying 142 is configured to obtain and manage a photographic log of the log module 50m to identify and track a potential device-related skin problem. For example, surveying 142 includes periodically prompting a user to take a photograph of a body part where stimulation is provided (e.g., once a week). The image can be analyzed by software of the App 21 designed to identify, measure, or track physical characteristics of bruises, irritation, or pressure sores. The surveying 142 module can be configured to adjust the schedule of photographic log entries, or questions about skin problems, based upon a user indicating skin risk as part of step 120 or based upon a user indicating skin risk as part of being surveyed 142 at scheduled times.

In embodiments, the Adverse Event (AE) module 50n may prompt a user at the end of every treatment session or periodically about whether they may have experienced any stimulation related problem. If a user answer indicates a potential problem then the user is surveyed further such as being provided with a picklist including, for example pain, sensitivity, redness, soreness, dryness, tear, bruising etc. If a user indicates a bruise or redness has appeared then this "risk event" can cause the AE module 50n to adjust the a parameter value of the coaching model in order to cause it to prompt a user to take a picture of the body part every day until the event is no longer indicated by the user as present. The tracking provided by the AE module 50n allows a user, or medical professional to track a risk event over time. By taking a picture of a bruise over multiple days the progression of the risk event can be compared to see if it is worsening, stable, or improving. If the status of a candidate risk event (e.g., a minor skin sore) worsens then the user can be referred for a medical review which may occur as an office visit or by telemedicine video call through a telemedicine module 50d of the digital ecosystem.

The photographic log activity can be adjusted by the log module 50m according to user survey data obtained during onboarding when a user first uses the system 10a. For example, a user can be asked about characteristics related to increased risk for skin tears or if they bruise easily, are diabetic, and/or have various dispositions such as low blood that can lead to an increased risk of adverse skin events such as pressure ulcers. Low blood pressure (e.g., low diastolic or systolic blood pressure such as diastolic <49 mm Hg) may decrease the pressure of microcirculation near and under the stimulation pads due to pressure applied during treatment, and increase risk for bruising or pressure ulcers with repeated use of a wearable stimulator.

q) Signaling such as may occur in step 194 when used in a care environment like an assisted living facility, conditions which are associated with increased risk can be flagged by a caregiver, or nurse. For example, impaired sensory perception due to a medical disorder such as neuropathy, an impaired ability for the patient to communicate discomfort, for example, language barriers, cognitive impairment, or other condition. This flag may cause a visual indicator of increased risk for PU/I to appear on a nursing station, on a user device 20a, or elsewhere so that appropriate care is provided to a patient. This monitoring can be extended to risk of skin tear and selection of electrode pads with less tack.

r) Signaling such as providing signaling for at-risk patients is accomplished, for example, using a red LED on the device, an alert on the user device, or notification presented to care providers by the ecosystem software which may communicate with devices of people or health systems which are providing care. The signaling may notify caregiver staff that certain care is important such as alternating legs, checking for bruising or skin problems, providing pressure relief breaks during treatment, or providing post-treatment care such as leg message or heat/cold therapy.

s) Adjustment of device components, such as may occur in step 178 if the patient profile is adjusted so that they are shipped proper system components such as stimulation matrix replacements devoid of features to increase pressure or use of conduction surface with a protuberant edge; or a wrap model is selected that supplies less pressure; or a lower pressure setting is used in adjustable pressure accessories that is provided with the system. A stimulation matrix or band that applies less pressure can be selected according to a user's skin risk.

t) Provision of adjunct therapies such as may occur in step 184 and as disclosed below. Providing adjunctive therapy, before, during, or after stimulation may deter PU/I risk.

Adjunctive Therapy to Decrease Risk of, or Treat, MDPIs.

Adjunctive therapies can promote PU/I prevention and treatment. The appropriate adjunctive treatment may be related to PU/I characteristics such as stage, severity, size. In embodiments, adjunctive therapy may include, for example, electrical, thermal, and negative-pressure therapy. This can be prompted or provided by the system before, during, or after electrical stimulation to treat a disorder such as OAB.

a) Adjunctive electrical stimulation can deter or promote healing of PU/Is such as stimulating using selected frequencies which have been found to promote healing. Adjunct electrical stimulation treatment protocols are provided to, for example, increase capillary density and perfusion, promote the response of fibroblast, neutrophil macrophage collagen, and DNA synthesis, and, increase the number of receptor sites for specific growth factors. The stimulation pads used to provide adjunct electrical stimulation may be the same or different than those of the stimulation matrix which are used to provide treatment of a disorder (e.g., pelvic floor disorder). For example, in an embodiment pulse frequency is set to the 100 pulses/second range and the voltage is set (e.g., 50 to 150 volts) sufficient to deliver a current that produces a moderately strong but comfortable tingling sensation under the pads or a just-visible muscle contraction. In embodiments, the polarity of the electrodes placed on or straddling the PU/I can be adjusted depending on the wound's clinical needs. For example, to promote autolysis, the stimulation protocol may use positive polarity to attract negatively charged neutrophils and macrophages. Alternatively, to encourage granulation tissue development, the protocol may use negative polarity to attract positively charged fibroblasts. To stimulate wound resurfacing, positive polarity may be selected to attract negatively charged epidermal cells. The schedule of adjunctive electrical treatment can be 1-2 hours a day, 5 to 7 days a week, for a long as needed.

b) Heat therapy (normotherapy): heat is used to increase blood flow and promote fibroblasts, increase metabolic demands of tissue to increase microcirculation, and modulate other factors associated with PU/I healing. The system includes an accessory for providing heat to skin. This may include thermal energy caused by sound, vibration, light/LED-induced heating of skin or fabrics or substances designed to retain or provide heat/cooling to skin. It is likely that modulation of heat after the application of pressure/stimulation would be most beneficial.

c) Microcirculation therapy: stimulation such as vibration, sonic, or ultrasonic energy is provided to increase microcirculation. Treatment may include short (e.g., 10-sec) bursts of vibration at a selected frequency (e.g., 20-50 Hz) and amplitude (e.g., 1-2 mm) followed by a pause (e.g., 5 to 10 sec) to increase skin blood flow. In an embodiment, the wrap is provided with a vibration transducer and the control module is provided with stimulation protocols for adjunctive therapy, or the system includes an accessory device to provide the adjunctive therapy.

d) Negative pressure wound therapy such as can be s provided by the system using an accessory with a pump to supply vacuum over an area of a PU/I.

Additional Health States and Measures.

When the system is used to provide treatment of a pelvic floor disorder, or other disorder, that requires ongoing repeated use of the device on a daily, weekly, or monthly basis, then, monitoring of changes in blood flow in the limb versus baseline measurements can allow monitoring of additional health states and conditions of a user. In embodiments, the system can be used for adjunctive monitoring of vascular disease and neuropathy before, during, or after providing stimulation for the treatment of overactive bladder. For example, the neurostimulator sensing module 34 can adopted to monitor peripheral blood flow in the limb using a sensor such as an integrated piezoelectric sensor array and/or ultrasound measurements.

In an embodiment, cardiovascular measures such as heart rate variability, blood pressure, heart rate, and oxygen saturation may be incorporated to provide adjunct monitoring of health states and conditions that are different than the primary condition for which stimulation treatment is being provided. Additionally, these measures can be used to assess the user's response to stimulation treatment for disorder such as a pelvic floor disorder.

Other measures may be obtained using a ring-like accessory into the system such as those obtained by the Oura ring (https://ouraring.com/), incorporated by reference herein, related to cardiovascular measures, heart rate variability, sleep quality and duration, etc.

In an embodiment, monitoring of an additional health state or condition includes peripheral neuropathy monitored, for example, by detecting changes in nerve conduction velocities measured in response to a stimulation signal and sensed by a system component.

All embodiments may deviate from that described and are not meant to be limiting of the spirit of the invention. Various modifications, adaptations, and alternative designs are of course possible considering the above teachings. Therefore, it should be understood that within the scope of the appended claims the invention may be practiced otherwise than as specifically described herein. Various combinations or sub-combinations of the specific features and aspects of the embodiments disclosed above may be made and still fall within one or more of the inventions. Further, the disclosure herein of any feature, aspect, method, step, characteristic, quality, attribute, element, or the like in connection with an embodiment can be used in all other embodiments set forth herein. Any prior art reference or article cited in the disclosure is incorporated by reference herein for all purposes.

Features and aspects of the disclosed embodiments can be combined with or substituted for one another to form varying modes of the disclosed inventions. The scope of the present inventions herein disclosed should not be limited by the disclosed embodiments described above. Moreover, while the invention is susceptible to various modifications, and alternative forms, specific examples thereof have been shown in the drawings and are herein described in detail. It should be understood, that the invention is not to be limited to the forms or methods disclosed, but to the contrary, the invention is to cover all modifications, equivalents, and alternatives falling within the spirit and scope of the various embodiments described and the appended claims.

Any methods disclosed herein need not be performed in the order recited. The methods disclosed herein include certain actions taken by a user or the software; however, they can also include any third-party instruction of those actions, either expressly or by implication. For example, actions such as "placing the matrix" include "instructing on the placement". The ranges disclosed herein also encompass any and all overlap, sub-ranges, and combinations thereof. Language such as "up to," "at least," "greater than," "less than," "between," and the like includes the number recited. All titles and section headings are for readability purposes and are not intended to limit the invention in any manner.

In embodiments, not all of the steps of a method shown in the figures must occur, or occur in the same order as shown in the figure. Additionally, method steps shown in the figures can occur in isolation or be combined with methods shown in other steps.

What is claimed is:

1. A transcutaneous stimulation system comprising:
   a stimulation module having at least one electrical stimulus generator for transmitting electrical-signals through a plurality of electrical generator channels;
   a control module electrically coupled to said at least one electrical stimulus generator for activating or deactivating each of said electrical generator channels in accordance with a predetermined stimulation protocol having a set of at least two stimulation montages with a weighting value defined for each of a set of activated pads,
   a wearable stimulation matrix defining a plurality of pairs of electrical stimulation pads activated transcutaneously which are adapted to be positioned in a releasably fixed and predefined arrangement on an external surface of a user's skin, each of said pairs of electrical stimulation pads having a cathodic pad and an anodic pad electrically coupled to a respective cathodic and anodic electrical generator channel, each of said electrical stimulation pads being in (1) an active state having a weighting value when a respective electrical generator channel is activated, and (2) an inactive state when a respective electrical generator channel is deactivated;
   a first stimulation montage defined for the pads of the stimulation matrix where each of said electrical stimulation pads is in said active state with a first weighting value in accordance with said predetermined stimulation protocol or said inactive state;
   at least a second stimulation montage defined for the pads of the stimulation matrix where at least one of said electrical stimulation pads is in an inactive state or an active state that has a second weighting value that is different than the first weighting value when said at least one stimulation pad is in said active state with the first weighting value in said first stimulation montage; and,
   a user interface device for permitting user input that is used to cause transitioning said stimulation matrix from said first stimulation montage to said at least second stimulation montage in accordance with a defined set of montages defined by said predetermined stimulation protocol during a treatment of the user.

2. The transcutaneous stimulation system as recited in claim 1 where said plurality of electrical generators has at least four electrical generator channels.

3. The transcutaneous stimulation system as recited in claim 1 where said stimulation matrix has at least four electrical stimulation pads.

4. The transcutaneous stimulation system as recited in claim 3 where said electrical stimulation pads of said stimulation matrix are displaced each from the other in a predefined geometrical pattern.

5. The transcutaneous stimulation system as recited in claim 4 where said geometrical pattern of said electrical stimulation pads define a triangular envelope.

6. The transcutaneous stimulation system as recited in claim 1 including a stimulation protocol of said stimulation module defining a set of predefined stimulation montages for said stimulation matrix where each of said predefined stimulation montages has individualized electrical stimulation pads with predetermined active state with a weighting value defined for each of the set of activated pads or inactive states.

7. The transcutaneous stimulation system as recited in claim 1 including electrical generator settings of the first and second stimulation montages being adjustable for enabling said transitioning between said first and said second stimulation montages to be performed that meets a perceptual criteria.

8. The transcutaneous stimulation system as recited in claim 7 wherein the perceptual criteria is designed so that the transitions between the at least first and second montage is defined to be above the just noticeable difference found using a group of users so that a user is more likely to notice the transitions.

9. The transcutaneous stimulation system as recited in claim 7 wherein the perceptual criteria is designed so that the transitions between the at least first and second montage is defined to enable the transitions to occur without causing perceived jumps in intensity to be above a level that is determined to be distracting for a group of users so that a user is more likely to be capable of noticing changes in recruitment evoked paresthesia.

10. The transcutaneous stimulation system as recited in claim 1 wherein the weighting value defined for each channel is used to adjust at least one of: an amplitude of a stimulation signal provided by an electrical generator stimulation channel associated with a pad, and the pulse width of stimulation pulses of a stimulation signal provided by an electrical generator stimulation channel associated with a pad.

11. The system as recited in claim 1 wherein amplitudes of the electrical generator signals set in the at least said second stimulation matrix montage are set in relation to the (a) electrical signal amplitudes in the first stimulation montage, and, (b) the difference in the number of stimulation pads in the active or inactive states.

12. The system as recited in claim 11 wherein said first stimulation montage includes two active state stimulation pads and the second stimulation montage includes four active state stimulation pads where the amplitude of the electrical generator signal for at least a portion of the channels of said second stimulation montage is greater than at least 50% of the amplitude in said first stimulation montage.

13. The system as recited in claim 11 wherein said first stimulation montage includes two active electrical active stimulation pads and said second stimulation montage includes four active electrical active stimulation pads with the electrical generator signal for at least a portion of the channels of the second stimulation montage being within the range of 60%-90% of the electrical generator signal of the first stimulation montage.

14. The system of claim 1 wherein said first stimulation montage has six electrical stimulation pads in said active states coupled respectively to said electrical generator channels with each of said electrical generator channels having a weighted amplitude signal in the range of 70%-100% of a predefined electrical signal in five of said stimulation montages for providing predetermined amounts of stimulation between opposingly positioned electrical stimulation pads.

15. The system of claim 1 wherein the set of stimulation montages includes a selected set of montages that has previously been shown in a group of patients to typically enable perception of movement of an electrical field from one side of said stimulation matrix to an opposing side of said stimulation matrix in a transition between said first stimulation montage to said at least said second stimulation montage when said stimulation montages are sequentially selected.

16. The system of claim 1 wherein the set of stimulation montages includes between 3 and 7 stimulation montages.

17. The system of claim 1 wherein the set of stimulation montages includes 5 stimulation montages.

18. The system of claim 1 wherein the set of stimulation montages further includes an "all" montage in which the weights of all channels are approximately the same.

19. The system of claim 1 wherein the stimulation matrix and montages are adapted to operate as a component of a wearable device that is positioned on the medial side of the leg of the user to provide transcutaneous stimulation of a saphenous nerve of the user by providing targeted stimulation to a medial region of a leg of the user.

20. The system of claim 1 wherein the set of stimulation montages includes a selected series of montages to cause a maximum of an electrical field strength to move from a first to a second side of the stimulation matrix as stimulation montages are sequentially selected.

21. The system of claim 19 wherein the wearable device is secured to the leg of the user by a stretchable wrap.

22. The system of claim 1 wherein the stimulation matrix and montages are adapted to provide transcutaneous stimulation of a saphenous nerve of the user using a set of vertically oriented pairs of stimulation pads and montages that permit a stimulation field to move from a left side location of the stimulation matrix to a right side location of the stimulation matrix to provide targeted stimulation to a medial region of a leg of the user.

* * * * *